US011633189B2

(12) United States Patent
Clarke et al.

(10) Patent No.: US 11,633,189 B2
(45) Date of Patent: *Apr. 25, 2023

(54) SYSTEMS AND METHODS FOR ENCLOSING AN ANATOMICAL OPENING

(71) Applicant: PULSAR VASCULAR, INC., Los Gatos, CA (US)

(72) Inventors: Gilbert Clarke, Seattle, WA (US); Brent Gerberding, San Jose, CA (US); Robert M. Abrams, Los Gatos, CA (US); Masoud Molaei, Mountain View, CA (US)

(73) Assignee: PULSAR VASCULAR, INC., Los Gatos, CA (US)

(*) Notice: Subject to any disclaimer, the term of this patent is extended or adjusted under 35 U.S.C. 154(b) by 786 days.

This patent is subject to a terminal disclaimer.

(21) Appl. No.: 16/458,939

(22) Filed: Jul. 1, 2019

(65) Prior Publication Data
US 2019/0336134 A1 Nov. 7, 2019

Related U.S. Application Data

(63) Continuation of application No. 15/010,466, filed on Jan. 29, 2016, now Pat. No. 10,335,153, which is a
(Continued)

(51) Int. Cl.
*A61B 17/12* (2006.01)
*A61B 17/00* (2006.01)

(52) U.S. Cl.
CPC .... *A61B 17/12113* (2013.01); *A61B 17/1214* (2013.01); *A61B 17/1219* (2013.01);
(Continued)

(58) Field of Classification Search
CPC ........ A61B 17/12113; A61B 17/12118; A61B 17/12109; A61B 17/1214;
(Continued)

(56) References Cited

U.S. PATENT DOCUMENTS 3,868,956 A 3/1975 Alfidi
4,164,045 A 8/1979 Bokros et al.
(Continued)

FOREIGN PATENT DOCUMENTS

AU 2006304660 4/2007
CN 1384726 12/2002
(Continued)

OTHER PUBLICATIONS

Cordis NeuroVascular, Inc.; "Masstransit Microcatheter," Product Brochure; No. 153-8383-3; Miami Lakes, FL, USA (2003).
(Continued)

*Primary Examiner* — Katherine H Schwiker
(74) *Attorney, Agent, or Firm* — Troutman Pepper Hamilton Sanders LLP

(57) ABSTRACT

Implantable therapeutic devices and methods for endovascular placement of devices at a target site, such an opening at a neck of an aneurysm, are disclosed. Selected embodiments of the present technology have closures that at least partially occlude the neck of an aneurysm to stabilize embolic or coagulative treatment of the aneurysm.

19 Claims, 30 Drawing Sheets

Related U.S. Application Data continuation of application No. 13/695,184, filed as application No. PCT/US2010/047908 on Sep. 3, 2010, now Pat. No. 9,277,924.

(60) Provisional application No. 61/313,096, filed on Mar. 11, 2010, provisional application No. 61/240,180, filed on Sep. 4, 2009.

(52) U.S. Cl.
CPC .. *A61B 17/12022* (2013.01); *A61B 17/12118* (2013.01); *A61B 17/12145* (2013.01); *A61B 17/12172* (2013.01); *A61B 2017/00632* (2013.01); *A61B 2017/00867* (2013.01); *A61B 2017/12054* (2013.01)

(58) Field of Classification Search
CPC ........ A61B 17/12145; A61B 17/12168; A61B 17/12172; A61B 17/12022; A61B 17/12027; A61B 17/12031; A61B 17/12036; A61B 17/12131; A61B 17/1215; A61B 17/12163; A61B 17/12177

See application file for complete search history.

(56) References Cited

U.S. PATENT DOCUMENTS

| | | |
|---|---|---|
| 4,248,234 A | 2/1981 | Assenza et al. |
| 4,645,495 A | 2/1987 | Vaillancourt |
| 4,651,751 A | 3/1987 | Swendson et al. |
| 4,665,906 A | 5/1987 | Jervis |
| 4,706,671 A | 11/1987 | Weinrib |
| 4,710,192 A | 12/1987 | Liotta |
| 4,739,768 A | 4/1988 | Engelson |
| 4,820,298 A | 4/1989 | Leveen et al. |
| 4,873,978 A | 10/1989 | Ginsburg |
| 4,909,787 A | 3/1990 | Danforth |
| 4,994,069 A | 2/1991 | Ritchart et al. |
| 5,011,488 A | 4/1991 | Ginsburg |
| 5,074,869 A | 12/1991 | Daicoff |
| 5,122,136 A | 6/1992 | Gugliemi et al. |
| 5,226,911 A | 7/1993 | Chen et al. |
| 5,250,071 A | 10/1993 | Palermo |
| 5,261,916 A | 11/1993 | Engelson |
| 5,263,964 A | 11/1993 | Purdy |
| 5,263,974 A | 11/1993 | Matsutani |
| 5,271,414 A | 12/1993 | Partika et al. |
| 5,304,195 A | 4/1994 | Twyford, Jr. et al. |
| 5,334,168 A | 8/1994 | Hemmer |
| 5,342,386 A | 8/1994 | Trotta |
| 5,350,397 A | 9/1994 | Palermo et al. |
| 5,354,295 A | 10/1994 | Gugliemi et al. |
| 5,527,338 A | 6/1996 | Purdy |
| 5,531,685 A | 7/1996 | Hemmer et al. |
| 5,578,074 A | 11/1996 | Mirigian |
| 5,624,449 A | 4/1997 | Pham et al. |
| 5,643,254 A | 7/1997 | Scheldrup et al. |
| 5,665,106 A | 9/1997 | Hammerslag |
| 5,669,931 A | 9/1997 | Kuplecki et al. |
| 5,693,067 A | 12/1997 | Purdy |
| 5,733,294 A | 3/1998 | Forber et al. |
| 5,733,329 A | 3/1998 | Wallace et al. |
| 5,749,890 A | 5/1998 | Shaknovich |
| 5,749,894 A | 5/1998 | Engelson |
| 5,759,194 A | 6/1998 | Hammerslag |
| 5,766,192 A | 6/1998 | Zacca |
| 5,769,884 A | 6/1998 | Solovay |
| 5,797,953 A | 8/1998 | Tekulve |
| 5,814,062 A | 9/1998 | Sepetka et al. |
| 5,843,103 A | 12/1998 | Wulfman |
| D407,818 S | 4/1999 | Mariant et al. |
| 5,895,391 A | 4/1999 | Farnholtz |
| 5,895,410 A | 4/1999 | Forber et al. |
| 5,910,145 A | 6/1999 | Fischell et al. |
| 5,911,737 A | 6/1999 | Lee et al. |
| 5,916,235 A | 6/1999 | Guido |
| 5,925,060 A | 7/1999 | Forber |
| 5,925,062 A | 7/1999 | Purdy |
| 5,925,683 A | 7/1999 | Park |
| 5,928,260 A | 7/1999 | Chin et al. |
| 5,933,329 A | 8/1999 | Tijanoc et al. |
| 5,935,114 A | 8/1999 | Jang et al. |
| 5,935,148 A | 8/1999 | Villar et al. |
| 5,951,599 A | 9/1999 | McCrory |
| 5,968,068 A | 10/1999 | Dehdashtian et al. |
| 5,980,514 A | 11/1999 | Kupiecki et al. |
| 5,980,554 A | 11/1999 | Lenker et al. |
| 5,984,944 A | 11/1999 | Forber |
| 6,007,544 A | 12/1999 | Kim |
| 6,013,055 A | 1/2000 | Bampos et al. |
| 6,022,341 A | 2/2000 | Lentz |
| 6,036,720 A | 3/2000 | Abrams et al. |
| 6,063,070 A | 5/2000 | Eder |
| 6,063,104 A | 5/2000 | Villar et al. |
| 6,071,263 A | 6/2000 | Kirkman |
| 6,077,291 A | 6/2000 | Das |
| 6,081,263 A | 6/2000 | LeGall et al. |
| 6,090,125 A | 7/2000 | Horton |
| 6,093,199 A | 7/2000 | Brown et al. |
| 6,096,021 A | 8/2000 | Helm et al. |
| 6,096,034 A | 8/2000 | Kuplecki et al. |
| 6,102,917 A | 8/2000 | Maitland et al. |
| 6,110,191 A | 8/2000 | Dehdashtian et al. |
| 6,117,157 A | 9/2000 | Tekulve |
| 6,139,564 A | 10/2000 | Tech |
| 6,146,339 A | 11/2000 | Biagtan et al. |
| 6,152,944 A | 11/2000 | Holman et al. |
| 6,168,615 B1 | 1/2001 | Ken et al. |
| 6,168,622 B1 | 1/2001 | Mazzocchi |
| 6,174,322 B1 | 1/2001 | Schneidt |
| 6,183,495 B1 | 2/2001 | Lenker et al. |
| 6,193,708 B1 | 2/2001 | Ken et al. |
| RE37,117 E | 3/2001 | Palermo |
| 6,221,066 B1 | 4/2001 | Ferrera et al. |
| 6,221,086 B1 | 4/2001 | Forber |
| 6,224,610 B1 | 5/2001 | Ferrera |
| 6,228,052 B1 | 5/2001 | Phondorf |
| 6,261,305 B1 | 7/2001 | Marotta et al. |
| 6,293,960 B1 | 9/2001 | Ken |
| 6,296,622 B1 | 10/2001 | Kurz et al. |
| 6,309,367 B1 | 10/2001 | Boock |
| 6,325,807 B1 | 12/2001 | Que |
| 6,344,041 B1 | 2/2002 | Kupiecki et al. |
| 6,344,048 B1 | 2/2002 | Chin et al. |
| 6,361,558 B1 | 3/2002 | Hieshima et al. |
| 6,375,668 B1 | 4/2002 | Gifford et al. |
| 6,383,174 B1 | 5/2002 | Eder |
| 6,398,791 B1 | 6/2002 | Que |
| 6,478,773 B1 | 11/2002 | Gandhi et al. |
| 6,491,711 B1 | 12/2002 | Durcan |
| 6,517,515 B1 | 2/2003 | Eidenschink |
| 6,530,935 B2 | 3/2003 | Wensel et al. |
| 6,533,905 B2 | 3/2003 | Johnson et al. |
| 6,554,794 B1 | 4/2003 | Mueller et al. |
| 6,589,256 B2 | 7/2003 | Forber |
| 6,592,605 B2 | 7/2003 | Lenker et al. |
| 6,613,074 B1 | 9/2003 | Mitelberg et al. |
| 6,616,681 B2 | 9/2003 | Hanson et al. |
| 6,626,889 B1 | 9/2003 | Simpson et al. |
| 6,626,928 B1 | 9/2003 | Raymond et al. |
| 6,638,268 B2 | 10/2003 | Niazi |
| 6,652,556 B1 | 11/2003 | VanTassel et al. |
| 6,663,607 B2 | 12/2003 | Slaikeu et al. |
| 6,663,648 B1 | 12/2003 | Trotta |
| 6,669,795 B2 | 12/2003 | Johnson et al. |
| 6,672,338 B1 | 1/2004 | Esashi |
| 6,679,836 B2 | 1/2004 | Couvillon, Jr. |
| 6,679,903 B2 | 1/2004 | Kurz |
| 6,689,141 B2 | 2/2004 | Ferrera et al. |
| 6,694,979 B2 | 2/2004 | Deem et al. |
| 6,723,112 B2 | 4/2004 | Ho et al. |
| 6,730,119 B1 | 5/2004 | Smalling |

(56) References Cited

U.S. PATENT DOCUMENTS

| | | |
|---|---|---|
| 6,740,073 B1 | 5/2004 | Saville |
| 6,740,277 B2 | 5/2004 | Howell et al. |
| 6,746,468 B1 | 6/2004 | Sepetka |
| 6,780,196 B2 | 8/2004 | Chin et al. |
| 6,790,218 B2 | 9/2004 | Jayaraman |
| 6,802,851 B2 | 10/2004 | Jones et al. |
| 6,811,560 B2 | 11/2004 | Jones et al. |
| 6,824,553 B1 | 11/2004 | Samson et al. |
| 6,835,185 B2 | 12/2004 | Ramzipoor et al. |
| 6,837,870 B2 | 1/2005 | Duchamp |
| 6,843,802 B1 | 1/2005 | Villalobos et al. |
| 6,855,153 B2 | 2/2005 | Saadat |
| 6,863,678 B2 | 3/2005 | Lee et al. |
| 6,890,218 B2 | 5/2005 | Patwardhan et al. |
| 6,911,037 B2 | 6/2005 | Gainor et al. |
| 6,936,055 B1 | 8/2005 | Ken et al. |
| 6,939,055 B2 | 9/2005 | Durrant et al. |
| 6,986,774 B2 | 1/2006 | Middleman et al. |
| 6,994,092 B2 | 2/2006 | van der Burg et al. |
| 7,011,094 B2 | 3/2006 | Rapacki et al. |
| 7,033,374 B2 | 4/2006 | Schaefer et al. |
| 7,033,387 B2 | 4/2006 | Zadno-Azizi et al. |
| 7,122,043 B2 | 10/2006 | Greenhalgh et al. |
| 7,147,659 B2 | 12/2006 | Jones |
| 7,156,871 B2 | 1/2007 | Jones et al. |
| 7,169,177 B2 | 1/2007 | Obara |
| 7,229,461 B2 | 6/2007 | Chin et al. |
| 7,232,461 B2 | 6/2007 | Ramer |
| 7,267,679 B2 | 9/2007 | McGuckin, Jr. et al. |
| 7,306,622 B2 | 12/2007 | Jones et al. |
| 7,322,960 B2 | 1/2008 | Yamamoto et al. |
| 7,343,856 B2 | 3/2008 | Blöhdorn |
| 7,387,629 B2 | 6/2008 | Vanney et al. |
| 7,410,482 B2 | 8/2008 | Murphy et al. |
| 7,569,066 B2 | 8/2009 | Gerberding et al. |
| 7,608,088 B2 | 10/2009 | Jones et al. |
| 7,662,168 B2 | 2/2010 | McGuckin, Jr. et al. |
| 7,857,825 B2 | 12/2010 | Moran et al. |
| 7,892,254 B2 | 2/2011 | Klint et al. |
| 8,016,853 B2 | 9/2011 | Griffen et al. |
| 8,075,585 B2 | 12/2011 | Lee et al. |
| 8,187,315 B1 | 5/2012 | Clauson et al. |
| 8,262,692 B2 | 9/2012 | Rudakov |
| 8,388,650 B2 | 3/2013 | Gerberding et al. |
| 8,444,667 B2 | 5/2013 | Poster |
| 8,470,013 B2 | 6/2013 | Duggal et al. |
| 8,540,763 B2 | 9/2013 | Jones et al. |
| 8,545,530 B2 | 10/2013 | Eskridge et al. |
| 8,551,132 B2 | 10/2013 | Eskridge et al. |
| 8,556,953 B2 | 10/2013 | Berez et al. |
| 8,715,312 B2 | 5/2014 | Burke et al. |
| 8,715,338 B2 | 5/2014 | Frid |
| 8,728,141 B2 | 5/2014 | Riina et al. |
| 8,747,430 B2 | 6/2014 | Porter |
| 8,771,341 B2 | 7/2014 | Strauss et al. |
| 8,915,950 B2 | 12/2014 | Cam et al. |
| 8,926,680 B2 | 1/2015 | Ferrera et al. |
| 8,956,399 B2 | 2/2015 | Cam et al. |
| 8,979,893 B2 | 3/2015 | Gerberding et al. |
| 9,060,886 B2 | 6/2015 | Molaei et al. |
| 9,107,670 B2 | 8/2015 | Hannes et al. |
| 9,119,625 B2 | 9/2015 | Bachman et al. |
| 9,179,918 B2 | 11/2015 | Levy et al. |
| 9,186,267 B2 | 11/2015 | Losordo et al. |
| 9,192,388 B2 | 11/2015 | Cam et al. |
| 9,211,124 B2 | 12/2015 | Campbell et al. |
| 9,259,229 B2 | 2/2016 | Abrams et al. |
| 9,277,924 B2 | 3/2016 | Clarke et al. |
| 2002/0026232 A1 | 2/2002 | Marotta et al. |
| 2002/0165569 A1 | 11/2002 | Ramzipoor |
| 2003/0033003 A1 | 2/2003 | Harrison et al. |
| 2003/0055440 A1 | 3/2003 | Jones et al. |
| 2003/0057156 A1 | 3/2003 | Peterson et al. |
| 2003/0139802 A1 | 7/2003 | Wulfman et al. |
| 2003/0181922 A1 | 9/2003 | Alferness |
| 2003/0181942 A1 | 9/2003 | Sutton et al. |
| 2003/0195385 A1 | 10/2003 | DeVore |
| 2003/0195553 A1 | 10/2003 | Wallace et al. |
| 2003/0212412 A1 | 11/2003 | Dillard et al. |
| 2004/0044391 A1 | 3/2004 | Porter |
| 2004/0068314 A1 | 4/2004 | Jones et al. |
| 2004/0087998 A1 | 5/2004 | Lee et al. |
| 2004/0111112 A1* | 6/2004 | Hoffmann .......... A61B 17/1219 623/1.15 |
| 2004/0158311 A1 | 8/2004 | Berhow et al. |
| 2004/0167597 A1 | 8/2004 | Costantino et al. |
| 2004/0167602 A1 | 8/2004 | Fischell et al. |
| 2004/0172056 A1 | 9/2004 | Guterman et al. |
| 2004/0193246 A1 | 9/2004 | Ferrera |
| 2004/0210248 A1 | 10/2004 | Gordon et al. |
| 2004/0210298 A1 | 10/2004 | Rabkin et al. |
| 2005/0021023 A1 | 1/2005 | Guglielmi et al. |
| 2005/0025797 A1 | 2/2005 | Wang et al. |
| 2005/0033349 A1 | 2/2005 | Jones et al. |
| 2005/0033409 A1 | 2/2005 | Burke et al. |
| 2005/0096728 A1 | 5/2005 | Ramer |
| 2005/0107823 A1 | 5/2005 | Leone et al. |
| 2005/0177224 A1 | 8/2005 | Fogarty et al. |
| 2006/0004436 A1 | 1/2006 | Amarant et al. |
| 2006/0030929 A1 | 2/2006 | Musbach |
| 2006/0052862 A1 | 3/2006 | Kanamaru et al. |
| 2006/0058837 A1 | 3/2006 | Bose et al. |
| 2006/0064151 A1 | 3/2006 | Guterman et al. |
| 2006/0106418 A1 | 5/2006 | Seibold et al. |
| 2006/0200234 A1 | 9/2006 | Hines |
| 2006/0206199 A1 | 9/2006 | Churchwell et al. |
| 2006/0247680 A1 | 11/2006 | Amplatz et al. |
| 2006/0259131 A1 | 11/2006 | Molaei et al. |
| 2006/0264905 A1 | 11/2006 | Eskridge et al. |
| 2006/0264907 A1 | 11/2006 | Eskridge et al. |
| 2006/0276826 A1 | 12/2006 | Mitelberg |
| 2007/0067015 A1 | 3/2007 | Jones et al. |
| 2007/0083257 A1 | 4/2007 | Pal et al. |
| 2007/0088387 A1 | 4/2007 | Eskridge et al. |
| 2007/0106311 A1 | 5/2007 | Wallace et al. |
| 2007/0191884 A1 | 8/2007 | Eskridge et al. |
| 2007/0198075 A1 | 8/2007 | Levy |
| 2007/0203567 A1 | 8/2007 | Levy |
| 2007/0270902 A1 | 11/2007 | Slazas et al. |
| 2008/0004653 A1 | 1/2008 | Sherman et al. |
| 2008/0004692 A1 | 1/2008 | Henson et al. |
| 2008/0039930 A1 | 2/2008 | Jones et al. |
| 2008/0147100 A1 | 6/2008 | Wallace |
| 2008/0183143 A1 | 7/2008 | Palasis et al. |
| 2008/0221600 A1 | 9/2008 | Dieck et al. |
| 2008/0269774 A1 | 10/2008 | Garcia et al. |
| 2008/0319533 A1 | 12/2008 | Lehe |
| 2009/0069880 A1 | 3/2009 | Vonderwalde et al. |
| 2009/0125053 A1 | 5/2009 | Ferrera et al. |
| 2009/0306678 A1 | 12/2009 | Hardert et al. |
| 2010/0023105 A1 | 1/2010 | Levy et al. |
| 2010/0063531 A1 | 3/2010 | Rudakov et al. |
| 2010/0094335 A1 | 4/2010 | Gerberding et al. |
| 2011/0022149 A1 | 1/2011 | Cox et al. |
| 2011/0270373 A1 | 11/2011 | Sampognaro et al. |
| 2012/0143237 A1 | 6/2012 | Cam et al. |
| 2012/0143317 A1 | 6/2012 | Cam et al. |
| 2012/0245674 A1 | 9/2012 | Molaei et al. |
| 2012/0290067 A1 | 11/2012 | Cam et al. |
| 2012/0296361 A1 | 11/2012 | Cam et al. |
| 2013/0090682 A1 | 4/2013 | Bachman et al. |
| 2013/0204290 A1 | 8/2013 | Clarke et al. |
| 2013/0268046 A1 | 10/2013 | Gerberding et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304109 A1 | 11/2013 | Abrams et al. |
| 2014/0052233 A1 | 2/2014 | Cox et al. |
| 2014/0053420 A1 | 2/2014 | Hannes et al. |
| 2014/0121752 A1 | 5/2014 | Losordo et al. |
| 2014/0128901 A1 | 5/2014 | Kang et al. |
| 2014/0142603 A1 | 5/2014 | Eskridge et al. |

(56) References Cited

U.S. PATENT DOCUMENTS

| | | |
|---|---|---|
| 2014/0180377 A1 | 6/2014 | Bose et al. |
| 2014/0236216 A1 | 8/2014 | Gerberding |
| 2015/0039015 A1 | 2/2015 | Gerberding |
| 2015/0142025 A1 | 5/2015 | Brandeis |
| 2015/0142042 A1 | 5/2015 | Cox |
| 2015/0142043 A1 | 5/2015 | Furey |
| 2015/0157329 A1 | 6/2015 | Rudakov et al. |
| 2015/0157331 A1 | 6/2015 | Levy et al. |
| 2015/0164512 A1 | 6/2015 | Chin et al. |
| 2015/0164665 A1 | 6/2015 | Cam et al. |
| 2015/0182361 A1 | 7/2015 | Ferrera et al. |
| 2015/0196305 A1 | 7/2015 | Meyer et al. |
| 2015/0216534 A1 | 8/2015 | Riina et al. |
| 2015/0216687 A1 | 8/2015 | Gerberding et al. |
| 2015/0245932 A1 | 9/2015 | Molaei et al. |
| 2015/0250623 A1 | 9/2015 | Monstadt et al. |
| 2015/0282962 A1 | 10/2015 | Strauss et al. |
| 2015/0327867 A1 | 11/2015 | Bachman et al. |
| 2015/0342612 A1 | 12/2015 | Wu et al. |
| 2016/0015395 A1 | 1/2016 | Molaei et al. |
| 2016/0015396 A1 | 1/2016 | Cox et al. |
| 2016/0030050 A1 | 2/2016 | Franano et al. |
| 2016/0038153 A1 | 2/2016 | Losordo et al. |

FOREIGN PATENT DOCUMENTS

| | | | |
|---|---|---|---|
| CN | 1399530 | 2/2003 | |
| CN | 1399531 A | 2/2003 | |
| CN | 101426454 A | 5/2009 | |
| CN | 101479006 A | 7/2009 | |
| CN | 101489492 | 7/2009 | |
| CN | 102202585 | 9/2011 | |
| CN | 103230290 | 8/2013 | |
| CN | 103381101 | 11/2013 | |
| CN | 103582460 | 2/2014 | |
| CN | 103607964 | 2/2014 | |
| DE | 102008028308 A1 * | 4/2009 | ....... A61B 17/12022 |
| DE | 102008028308 A1 | 4/2009 | |
| EP | 0820726 | 1/1998 | |
| EP | 00996372 | 5/2000 | |
| EP | 1269935 | 1/2003 | |
| EP | 1527753 | 4/2005 | |
| EP | 1951129 | 4/2007 | |
| EP | 2326259 | 6/2011 | |
| EP | 2713904 | 4/2014 | |
| EP | 2713905 | 4/2014 | |
| HK | 1134421 | 4/2010 | |
| JP | 2001286478 A | 10/2001 | |
| JP | 2002516705 A | 6/2002 | |
| JP | 2003512129 A | 4/2003 | |
| JP | 2005522266 A | 7/2005 | |
| JP | 2009512515 | 3/2009 | |
| JP | 2013226419 | 11/2013 | |
| KR | 20080081899 | 9/2008 | |
| WO | WO9724978 | 7/1997 | |
| WO | WO9726939 | 7/1997 | |
| WO | WO9731672 | 9/1997 | |
| WO | WO9823227 | 6/1998 | |
| WO | WO9850102 | 11/1998 | |
| WO | WO9905977 | 2/1999 | |
| WO | WO9907294 | 2/1999 | |
| WO | WO9915225 | 4/1999 | |
| WO | WO9907294 | 6/1999 | |
| WO | 0007524 A1 | 2/2000 | |
| WO | WO0013593 | 3/2000 | |
| WO | WO0130266 | 5/2001 | |
| WO | WO-0193782 A1 * | 12/2001 | ....... A61B 17/12022 |
| WO | WO-2001093782 | 12/2001 | |
| WO | WO-0200139 A1 * | 1/2002 | ....... A61B 17/12022 |
| WO | WO-2002000139 | 1/2002 | |
| WO | WO0213899 | 2/2002 | |
| WO | WO02071977 | 9/2002 | |
| WO | WO02078777 | 10/2002 | |
| WO | WO02087690 | 11/2002 | |
| WO | WO03059176 | 7/2003 | |
| WO | WO03075793 | 9/2003 | |
| WO | WO04019790 | 3/2004 | |
| WO | WO04026149 | 4/2004 | |
| WO | WO04105599 | 12/2004 | |
| WO | WO05033409 | 4/2005 | |
| WO | WOO 5082279 | 9/2005 | |
| WO | 2006034166 A2 | 3/2006 | |
| WO | WO2006119422 | 9/2007 | |
| WO | 2008027293 A2 | 3/2008 | |
| WO | WO2008151204 | 12/2008 | |
| WO | WO2007047851 | 3/2009 | |
| WO | WO2010028314 | 3/2010 | |
| WO | WO2011029063 | 3/2011 | |
| WO | WO2012167137 | 6/2012 | |
| WO | WO2012167150 | 12/2012 | |
| WO | WO2012167156 | 12/2012 | |
| WO | WO2013052920 | 4/2013 | |
| WO | WO2013169380 | 11/2013 | |
| WO | WO-2014029835 A1 | 2/2014 | |
| WO | WO-2015179377 A1 | 11/2015 | |

OTHER PUBLICATIONS

Cordis NeuroVascular, Inc.; "Prolwer Select Plus Microcatheter," Product Brochure; No. 154-9877-1; Miami Lakes, FL, USA (2003).

Cordis NeuroVascular, Inc.; "Prowler Select LP Microcatheter," Product Brochure; No. 155-5585; Miami Lakes, FL, USA (2004).

Cordis NeuroVascular, Inc.; "Rapid Transit Microcatheter," Product Brochure; No. 152-7369-2; Miami Lakes, FL, USA (2003).

Extended European Search Report, European Application No. 06826291.4, dated Nov. 19, 2009, 7 pages.

Gupta et al. SMST-2003: Proc. Intl. Conf. Shape Memory Superelastic Technol.; Pacific Grove, CA; p. 639; 2003.

International Search Report and Written Opinion for Application No. PCT/US2010/047908, dated May 25, 2011.

International Search Report and Written Opinion for International Application No. PCT/US2009/056133, dated Oct. 26, 2009, 11 pages.

International Search Report and Written Opinion for International Application No. PCT/US2010/047908, dated Mar. 15, 2012, 11 pages.

International Search Report and Written Opinion for International Application No. PCT/US2012/040552, dated Aug. 28, 2012, 14 pages.

International Search Report and Written Opinion for International Application PCT/US2012/040536, dated Oct. 15, 2012, 17 pages.

International Search Report and Written Opinion for International Application PCT/US2012/040558, dated Oct. 8, 2012, 17 pages.

International Search Report and Written Opinion for International Application PCT/US2012/059133, dated Mar. 11, 2013, 15 pages.

International Search Report and Written Opinion for International Application PCT/US2013/031793, dated Jun. 26, 2013, 14 pages.

International Search Report for International Application No. PCT/US06/40907, dated May 1, 2008, 2 pages.

MICRUS COPR.; "Concourse 14 Microcatheter" Product Brochure; Sunnyvale ,CA, USA.

Polytetraflouroethylene Implants, DermNet NZ, Nov. 11, 2005, http://dermetnz.org/polytetrafluoroethylene.html.

Singapore Examination Report for Singapore Application No. 200802811-0, dated Jul. 12, 2009, 7 pages.

Chinese Office Action issued in corresponding Chinese Application No. 2015102710739. cited in parent U.S. Appl. No. 15/010,466.

Extended European Search Report dated May 25, 2018 during the prosecution of European Patent Application No. 17197720.0. cited in parent U.S. Appl. No. 15/010,466.

Extended European Search Report dated Feb. 27, 2018 during the prosecution of European Patent Application No. EP17197714. cited in parent U.S. Appl. No. 15/010,466.

Extended European Search Report dated Feb. 5, 2018 during the prosecution of European Patent Application No. 17197725.9. cited in parent U.S. Appl. No. 15/010,466.

* cited by examiner

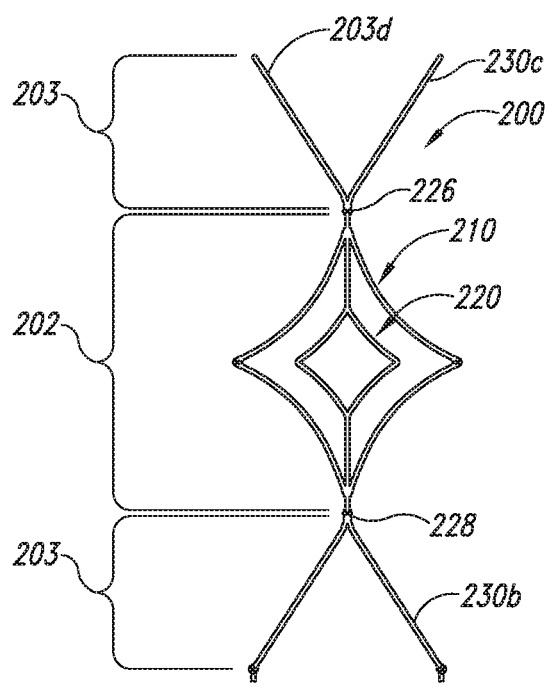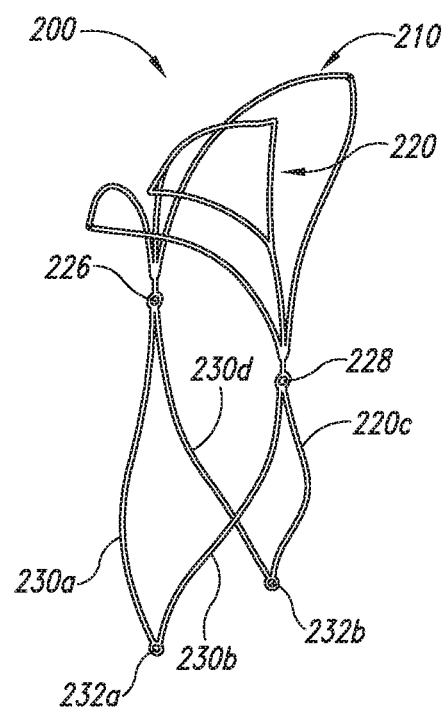
*Fig. 2A*  *Fig. 2B*
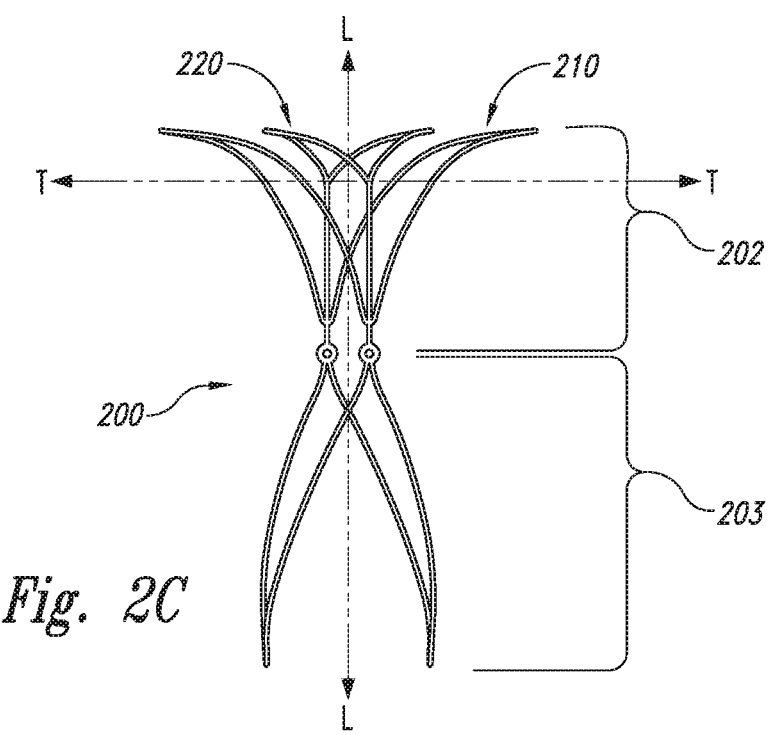
*Fig. 2C*

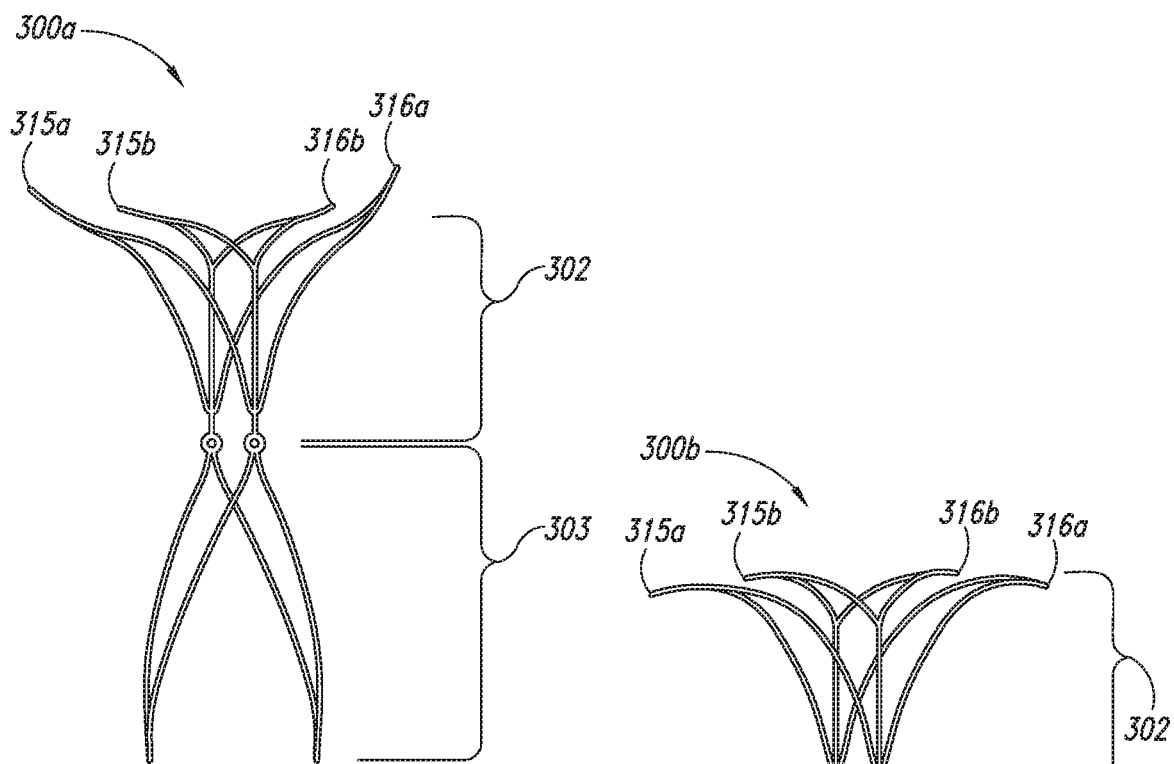
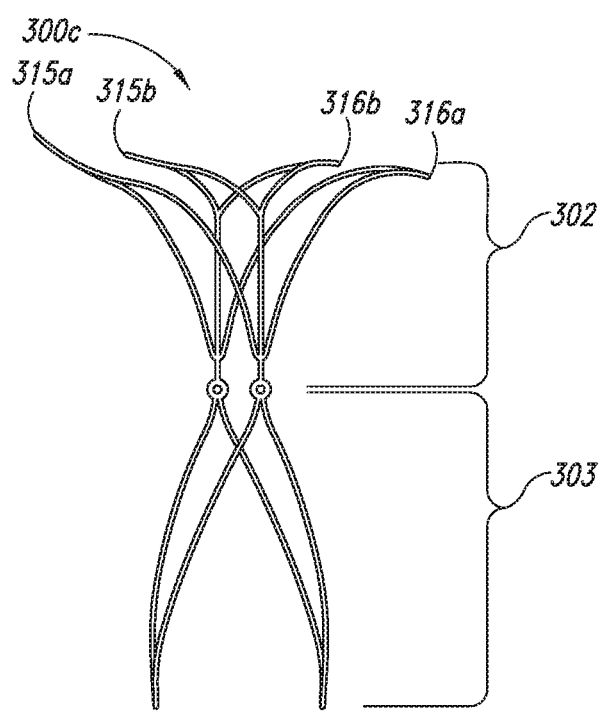

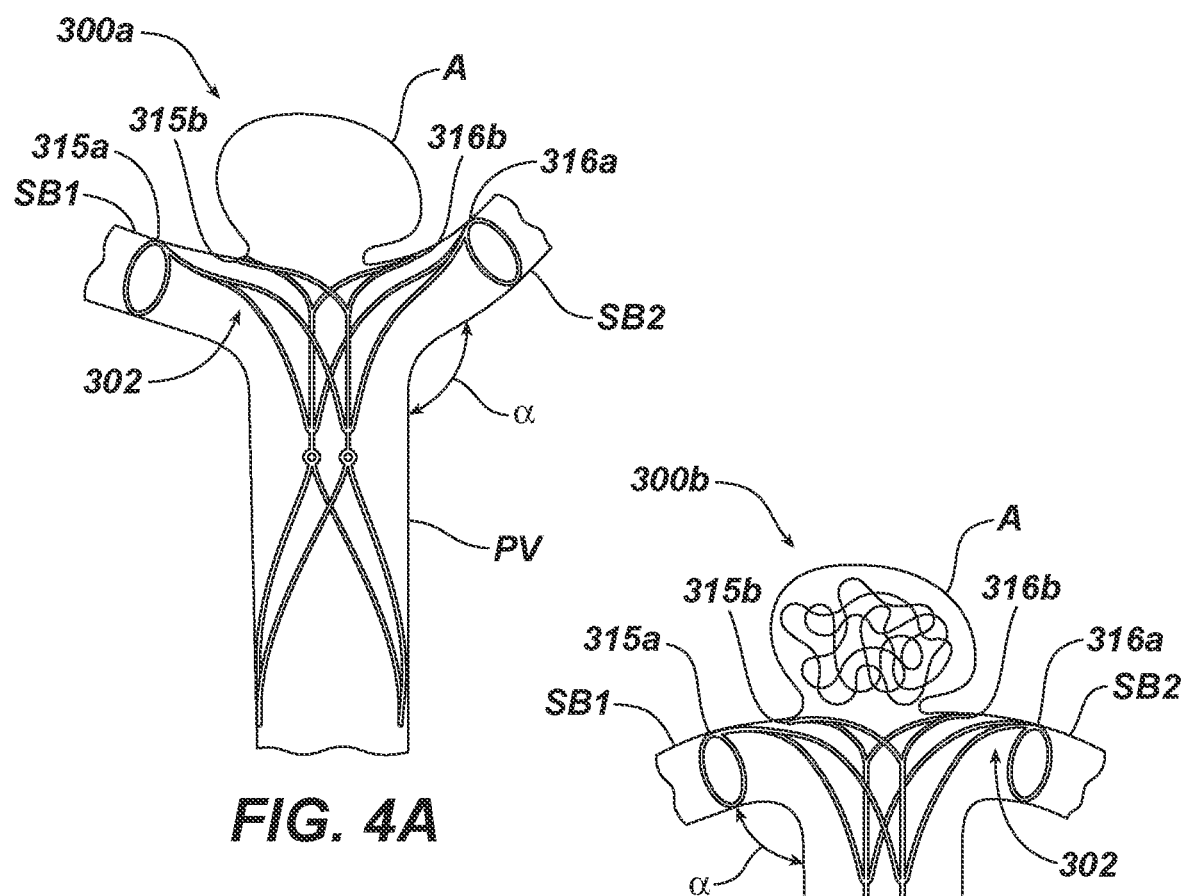
FIG. 4A
FIG. 4B
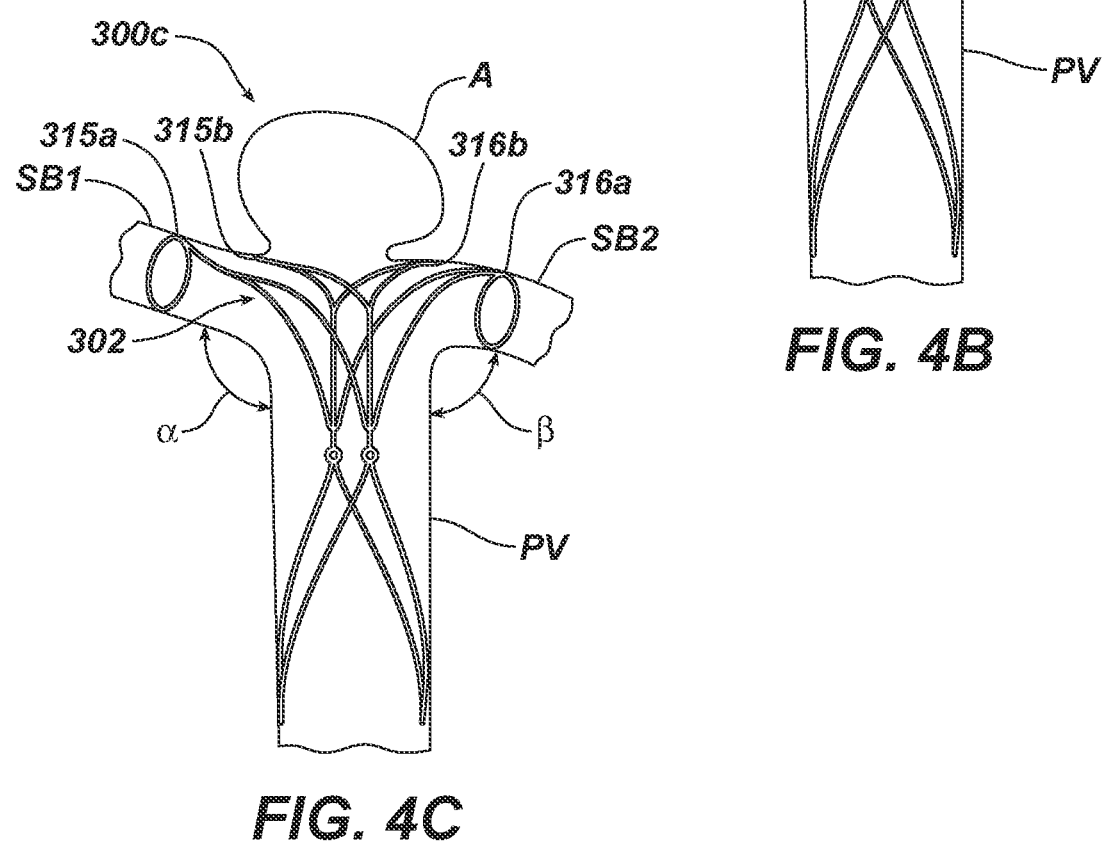
FIG. 4C

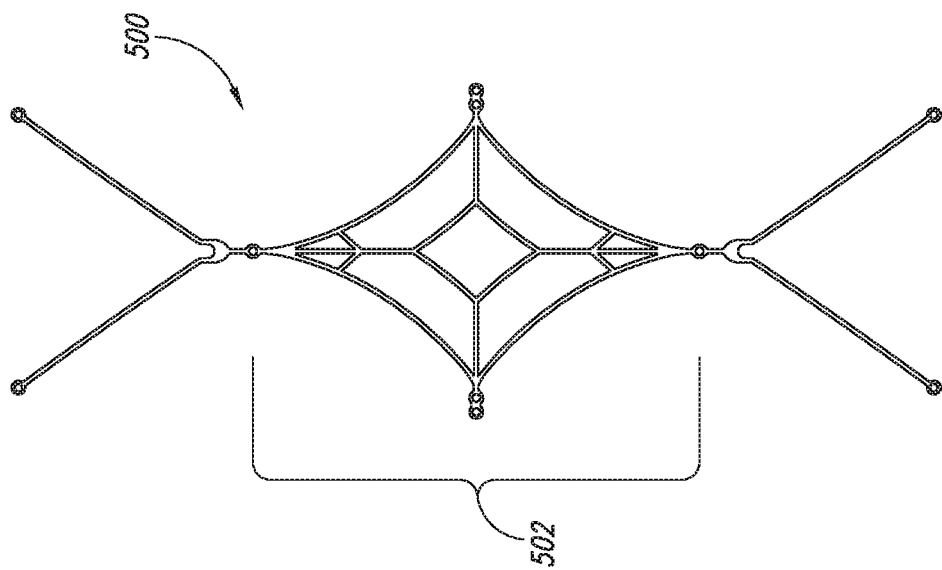
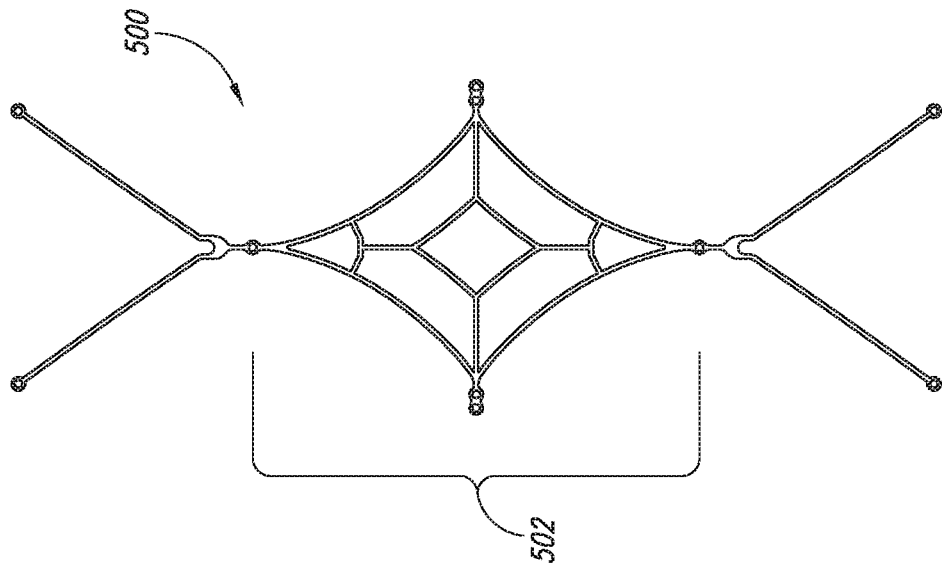
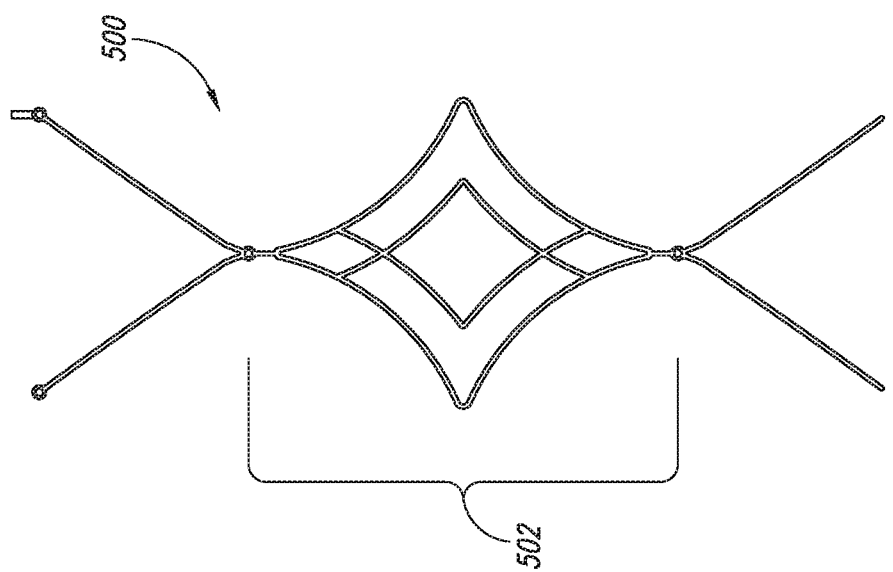

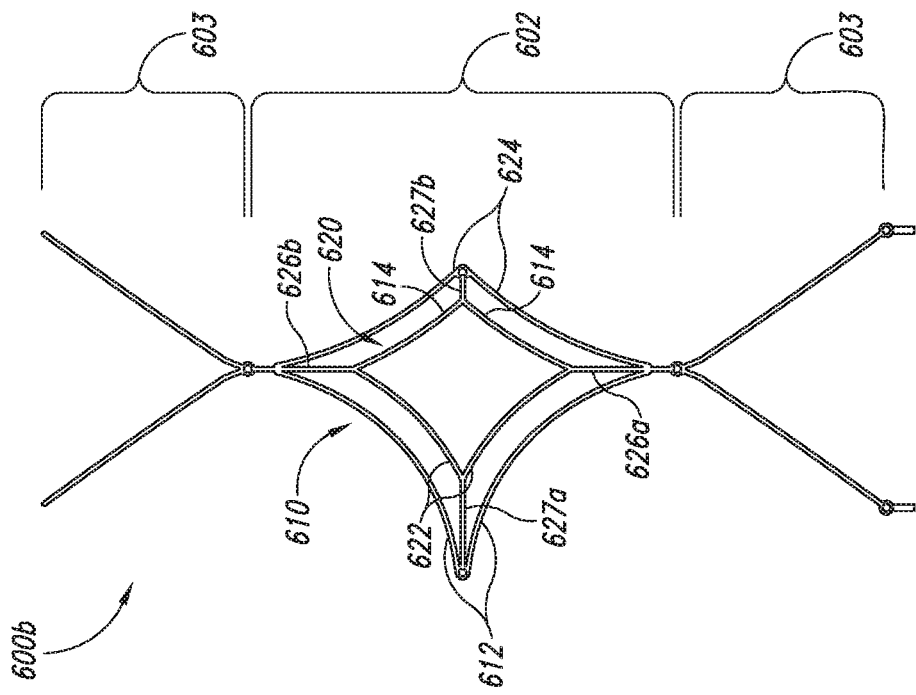
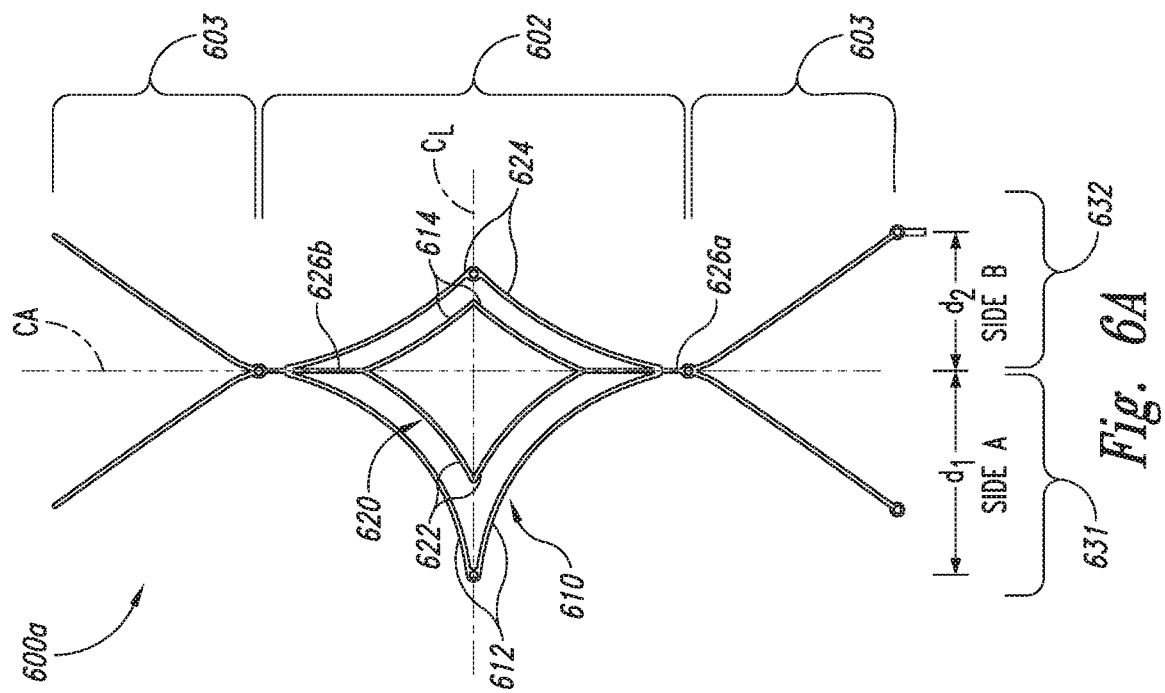

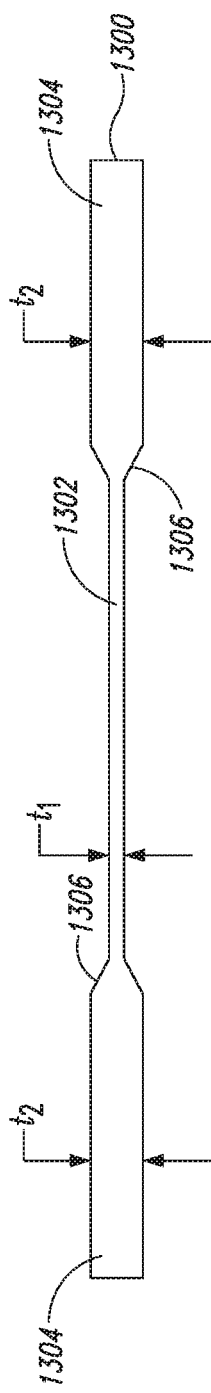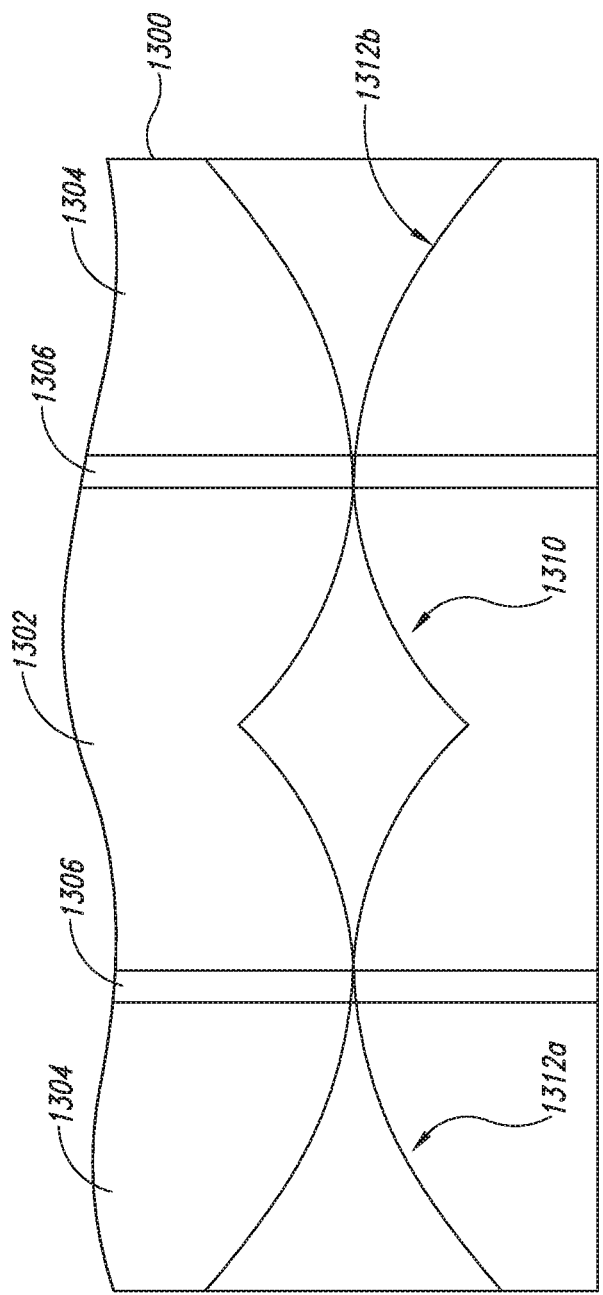
Fig. 13A
Fig. 13B

SYSTEMS AND METHODS FOR ENCLOSING AN ANATOMICAL OPENING

CROSS-REFERENCE TO RELATED APPLICATIONS

This application is a continuation of U.S. patent application Ser. No. 15/010,466 and filed Jan. 29, 2016, now U.S. Pat. No. 10,335,153, which is a continuation of U.S. patent application Ser. No. 13/695,184, 371(c) date accorded Apr. 22, 2013, now U.S. Pat. No. 9,277,924, which is a U.S. National Stage of International Application No. PCT/US2010/047908, filed Sep. 3, 2010, which claims priority to and the benefit of U.S. Provisional Patent Application No. 61/240,180, filed Sep. 4, 2009, and U.S. Provisional Patent Application No. 61/313,096, filed Mar. 11, 2010, all of which are incorporated by reference herein in their entireties.

TECHNICAL FIELD

The present technology relates to implantable therapeutic devices and methods for endovascular placement of devices at a target site, such an opening at a neck of an aneurysm. Selected embodiments of the present technology have closures that at least partially occlude the neck of an aneurysm to stabilize embolic or coagulative treatment of the aneurysm and methods of treating patients with aneurysms.

BACKGROUND

Many of the currently available surgical approaches for closing openings and repairing defects in anatomical lumens and tissues (e.g., blood vessels), septal defects, and other types of anatomical irregularities and defects are highly invasive. Surgical methods for clipping brain aneurysms, for example, require opening the skull, cutting or removing overlying brain tissue, clipping and repairing the aneurysm from outside the blood vessel, and then reassembling tissue and closing the skull. Surgical techniques for repairing septal defects are also highly invasive. The risks related to anesthesia, bleeding, and infection associated with these types of procedures are high, and tissue that is affected during the procedure may or may not survive and continue functioning.

Minimally invasive surgical techniques have been developed to place occlusive devices within or across an opening or cavity in the body, such as in the vasculature, spinal column, fallopian tubes, bile ducts, bronchial and other air passageways, and the like. In general, an implantable device is guided along a delivery catheter and through a distal opening of the catheter using a pusher or delivery wire to deploy the device at a target site in the vasculature. Once the occlusive device has been deployed at the target site, it is detached from the pusher mechanism without disturbing placement of the occlusive device or damaging surrounding structures.

Minimally invasive techniques are also highly desirable for treating aneurysms. In general, the minimally invasive therapeutic objective is to prevent material that collects or forms in the cavity from entering the bloodstream and to prevent blood from entering and collecting in the aneurysm. This is often accomplished by introducing various materials and devices into the aneurysm. One class of embolic agents includes injectable fluids or suspensions, such as microfibrillar collagen, various polymeric beads, and polyvinyl alcohol foam. Polymeric agents may also be cross-linked to extend their stability at the vascular site. These agents are typically deposited at a target site in the vasculature using a catheter to form a solid space-filling mass. Although some of these agents provide for excellent short-term occlusion, many are thought to allow vessel recanalization due to their absorption into the blood. Other materials, such as hog hair and suspensions of metal particles, have also been proposed and used to promote occlusion of aneurysms. Polymer resins, such as cyanoacrylates, are also employed as injectable vaso-occlusive materials. These resins are typically mixed with a radiopaque contrast material or are made radiopaque by the addition of a tantalum powder. Accurate and timely placement of these mixtures is crucial and very difficult because it is difficult or impossible to control them once they have been placed in the blood flow.

Implantable vaso-occlusive metallic structures are also well known and commonly used. Many conventional vaso-occlusive devices have helical coils constructed from a shape memory material or noble metal that forms desired coil configuration upon exiting the distal end of a delivery catheter. The function of the coil is to fill the space formed by an anatomical defect and to facilitate the formation of an embolus with the associated allied tissue. Multiple coils of the same or different structures may be implanted serially in a single aneurysm or other vessel defect during a procedure. Implantable framework structures are also used in an attempt to stabilize the wall of the aneurysm or defect prior to insertion of filling material such as coils.

Techniques for delivering conventional metallic vaso-occlusivedevices to a target site generally involve a delivery catheter and a detachment mechanism that detaches the devices, such as a coil, from a delivery mechanism after placement at the target site. For example, a microcatheter can be initially steered through the delivery catheter into or adjacent to the entrance of an aneurysm either with or without a steerable guidewire. If a guidewire is used, it is then withdrawn from the microcatheter lumen and replaced by the implantable vaso-occlusive coil. The vaso-occlusive coil is advanced through and out of the microcatheter and thus deposited within the aneurysm or other vessel abnormality. It is crucial to accurately implant such vaso-occlusive devices within the internal volume of a cavity and to maintain the device within the internal volume of the aneurysm. Migration or projection of a vaso-occlusive device from the cavity may interfere with blood flow or nearby physiological structures and poses a serious health risk.

In addition to the difficulties of delivering implantable occlusion devices, some types of aneurysms are challenging to treat because of structural features of the aneurysm or because of particularities of the site. Wide-neck aneurysms, for example, are known to present particular difficulty in the placement and retention of vaso-occlusive coils. Aneurysms at sites of vascular bifurcation are another example where the anatomical structure poses challenges to methods and devices that are effective in treating the typical sidewall aneurysms.

In view of such challenges, implanting conventional embolic coils, other structures, or materials in the internal space of an aneurysm has not been an entirely satisfactory surgical approach. The placement procedure may be arduous and lengthy because it often requires implanting multiple devices, such as coils, serially in the internal space of the aneurysm. Higher risks of complication from such sources as anesthesia, bleeding, thromboembolic events, procedural stroke, and infection are associated with such longer procedures. Moreover, because placement of structures in the internal space of an aneurysm does not generally completely occlude the opening, recanalization of the original aneurysm may occur, and debris and occlusive material may escape from within the aneurysm to create a risk of stroke or vessel blockage. Blood may also flow into the aneurysm and other blood vessel irregularities after the placement of embolic devices, which may increase the risks of complication and further enlargement of the aneurysm.

Despite the numerous conventional devices and systems available for implanting embolic materials in an aneurysm and for occluding physiological defects using minimally invasive techniques, these procedures remain risky and rarely restore the physiological structure to its normal, healthy condition. It is also challenging to position conventional implantable devices during deployment, prevent shifting or migration of such devices after deployment, and preserve blood flow in neighboring vessels following after deployment.

BRIEF DESCRIPTION OF THE DRAWINGS

FIGS. 2A-2C are views of an aneurysm device configured in accordance with still another embodiment of the technology.

FIGS. 3A-3C are views of aneurysm devices configured in accordance with other embodiments of the technology.

FIGS. 4A-4C are views of the aneurysm devices of FIGS. 3A-3C implanted at aneurysms.

FIGS. 5A-5H are views of aneurysm devices configured in accordance with other embodiments of the technology.

FIGS. 6A and 6B are views of asymmetric aneurysm devices configured in accordance with other embodiments of the technology in a flat configuration.

FIGS. 13A and 13B are views of a sheet of material from which aneurysm devices in accordance with the technology can be fabricated.

DETAILED DESCRIPTION

A. Overview/Summary

Figure 1A:
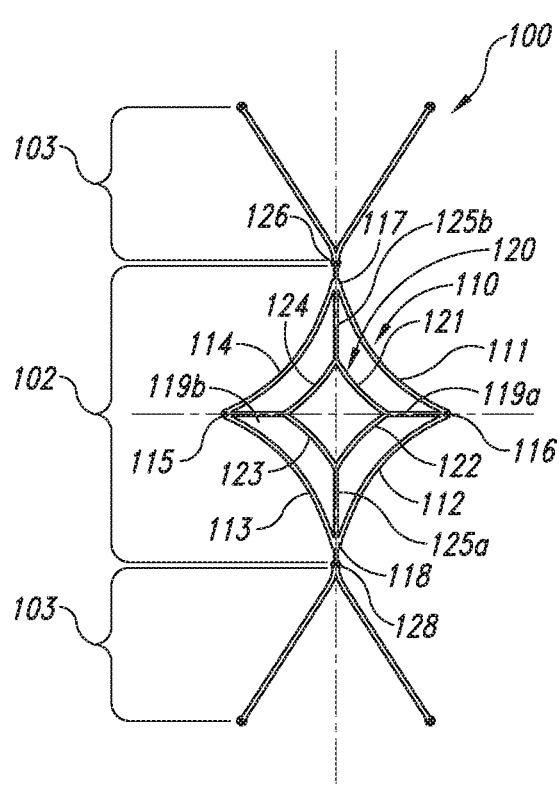
FIGS. 1A-1D are views of an aneurysm device configured in accordance with an embodiment of the technology.

The presently described technology provides an aneurysm closure device comprising a closure structure and a supplemental stabilizer. The closure structure can have a curved portion configured to extend along a first vessel, such as a side branch of a bifurcated vessel that extends along a lateral axis. The curved portion can have an arch with a proximal-facing surface curved about the lateral axis along the first vessel and a distal-facing surface configured to extend across at least a portion of a neck of an aneurysm at the first vessel. The curved portion of the closure structure can be further configured to exert a radially outward force against the first vessel. The supplemental stabilizer extends from the closure structure along a longitudinal axis transverse to the lateral axis of the first vessel. The supplemental stabilizer is configured to exert an outward force against a second vessel, such as a parent vessel, that extends transversely to the first vessel.

One application of the present technology is treating brain aneurysms that occur at complex sites or that have a wide neck. These sites are difficult to occlude or treat with conventional embolic coils. An example of a target site for which the technology is particularly well suited includes aneurysms near the terminus of the basilar artery where two posterior cerebellar arteries originate and diverge at a very wide-angle. Another useful implantation site includes aneurysms along the length of the middle cerebral artery, which bifurcates at several points. The identification of these particular target sites is not intended to be limiting; rather, many embodiments of the technology may be used to treat a variety of aneurysm sites or other pathological or traumatic anatomical openings.

The closure structure of the aneurysm device, which may comprise an occlusive or partially occlusive structure, establishes a boundary between the internal cavity of the aneurysm and the main stream of vascular flow. Such closure structures may, for example, be a frame, scaffold, or other structure that retains embolic coils or other coagulative material within the aneurysm. Some embodiments of the closure structure may further include a barrier, such as a membrane, a mesh, strands of a polymeric material (e.g., parylene), a one-way valve structure, or other types of covers, arranged over at least a portion of the frame. In embodiments with a membrane covering, the closure structure may be porous to liquid, but block movement of particulate or macroscopic material. However, even such a porous structure may slow the flow of blood sufficiently such that coagulative conditions are created within the aneurysm. In other embodiments, as described in detail below, the closure structure may be partially or fully covered with a membrane that significantly affects the flow of blood into the aneurysm. Such embodiments may act as a vascular flow diverter in addition to enclosing or otherwise occluding the aneurysm.

The relative advantages of the framework being bare (uncovered)versus the framework having a cover depend on the location and anatomy and clinical status of the aneurysm and the preferred clinical approach to its treatment. In general, when treatment of the aneurysm includes a relatively uncomplicated plan to insert embolic coils into the aneurysm to stabilize it, a bare enclosure framework is appropriate. However, when diversion of vascular flow into the aneurysm is particularly important, a cover or a partial cover over the framework may be advantageous. That being said, anatomical features' shape and size vary greatly with respect to brain aneurysms. Past treatment failures or recanalization may present an instance for use of a covered device to prevent future recurrence. Further, in areas rich in perforating arteries that could be potentially blocked by a cover, a bare device could be the more appropriate clinical option. Both types of embodiments, without a cover and with a cover, will be described in detail below.

In other aspects, the technology provides an implantable device assembly, as described further below, that includes the closure structure and a delivery wire to which the device is connected. In still another aspect, the presently described technology provides a system that includes a deliverable device assembly and a controller that delivers electrical energy to the assembly to detach the device from the delivery wire. Other aspects of the technology are directed to methods for delivering the device to the target site and for detaching the device from a delivery wire.

One embodiment of the described technology is a device that has a distal framework portion having a distal-facing aspect configured to enclose the targeted aneurysm, and a proximal-facing aspect configured to arch unobtrusively over lumina of the downstream arteries. The device also has a proximal support framework that is connected to the distal framework portion. The proximal support framework is configured to be implanted and reside in the parent artery, and it can be aligned against the luminal walls without intrusion into the lumen itself. The proximal support framework is biased to press outward against a luminal wall of the artery to provide stability against lateral slippage in either direction within the arteries that bifurcate from the terminus of the parent artery. A particular structural feature of the device is that the biasing force that stabilizes the proximal support framework actually originates within the distal framework portion of the device. This and other features of embodiments of the inventive device and method are described in further detail below.

Embodiments of the devices of the present technology may be customized for specific target site configurations. In one embodiment of the technology, for example, images of the target deployment site, the aneurysm, and the neighboring vessels may be used to determine the desired size, configuration, and shape set for implantable devices of the present technology. A suitable device template may be selected from a kit or library of template devices, either in their planar form or fully assembled form, such devices varying systematically in specifics of size and form of the distal framework portion and proximal support framework. In some embodiments, the specifics of size and form may be sufficiently specific to suit the intended target site. In other embodiments, based on data related to the intended target site, the device template may then be formed, curved, and shaped to conform to the anatomy of that site. Mother embodiments of the technology, individual components such as one of various distal framework portions and one of various proximal framework portions may be fabricated individually in a customized manner to conform to a target site, and then assembled together to form a customized device.

Several embodiments of the technology are methods and systems directed to reducing the length and complexity of minimally invasive procedures for supporting and occluding openings and repairing a lumen or tissue defect, and to restoring a physiological structure, such as a blood vessel, to its normal, healthy condition. In another aspect, selected embodiments of methods and systems of the present technology provide implantable devices for supporting and/or at least partially occluding and/or at least partially diverting flow away from an opening or cavity, such as an aneurysm, that are safely and conveniently deployable using minimally invasive techniques. Additional features of selected embodiments of the technology may reduce shifting and migration following placement and avoid restricting blood flow in neighboring vessels. In yet another aspect, selected embodiments of methods and systems of the present technology are directed to retaining materials inside a physiological opening or cavity, such as embolic materials within an aneurysm.

Specific details of several embodiments of the technology are described below with reference to FIGS. 1A-24B. Although many of the embodiments are described below with respect to devices that at least partially occlude brain aneurysms, other applications and other embodiments are within the scope of the technology. For example, several other embodiments of the technology can have different configurations, components, or procedures than those described in this section. A person of ordinary skill in the art, therefore, will accordingly understand that the technology may have other embodiments with additional elements, or the technology may have other embodiments without several of the features shown and described below with reference to FIGS. 1A-24B.

B. Axes and Orientation of the Device

Figure 1B:
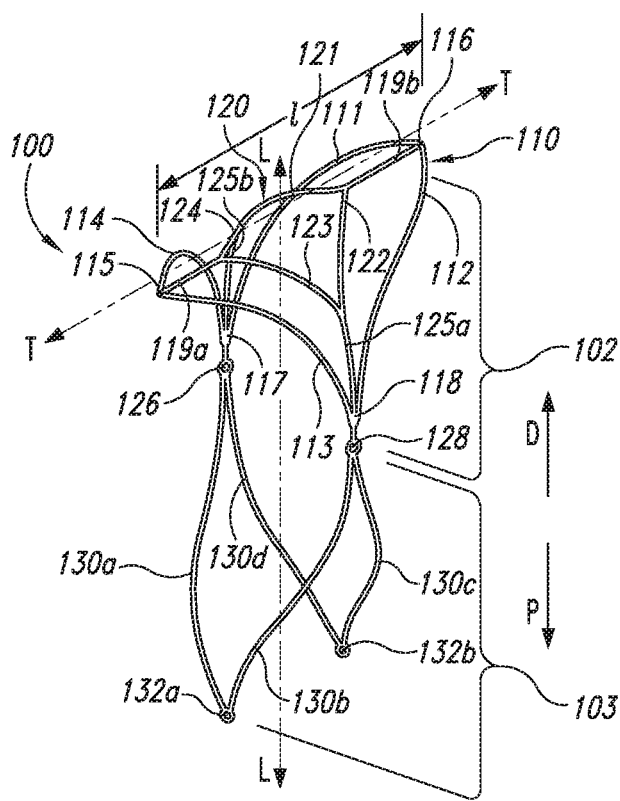

With regard to the use of "distal" and "proximal" within this application, an example of which is shown in FIG. 1B, distal (arrow D)refers to the direction or portion of the device generally further along the vasculature relative to blood flow from the heart, and proximal(arrow P) refers to the direction or portion of the device that is not as far along the vasculature relative to the distal portion. Inasmuch as the endovascular approach to the targeted implantation site is from the same direction as arterial flow, the proximal portion of the device is upstream within the vasculature, and the distal portion is downstream relative to the proximal portion. The terms distal and proximal also relate to the relative position of the portions of the device as the device is arranged on a delivery device such that "proximal" refers to the position closer to the operator of the device, and "distal" refers to the position that is more distant from the operator of the device.

With regard to the use of "longitudinal" in reference to device axes and orientation, an example of which is shown in FIGS. 1A-1D, the longitudinal axis L-L of the device is aligned with the lengthwise dimension of a supplemental stabilizer (e.g., the central longitudinal axis of the proximal framework support portion of the device). When the device is implanted at a target site, the longitudinal axis of the device and the supplemental stabilizer are aligned with the longitudinal dimension of a first vessel (e.g., parent vessel) within which the supplemental stabilizer is configured to reside.

With regard to the use of "lateral" in reference to device axes and orientation, an example of which is shown in FIGS. 1A-1D, the device also has a lateral axis T-T that is orthogonal or otherwise transverse to the longitudinal axis L-L. The lateral axis is a term particularly appropriate for the orientation of the lateral aspect "l" (FIG. 1B) of the closure structure (e.g., distal framework portion) that has structural elements that extend into at least one of the second vessels (e.g., side branches of bifurcating vessels). The second vessels are downstream from the first vessel, and the second vessels extend generally transverse (e.g., at a non-zero angle) with respect to the first vessel. Bifurcating arteries, for example, diverge at varying angles from their site of common origin; some angles can be very wide (e.g., nearly at right angles to the parent artery), or in other instances the angle between the bifurcating arteries may be fairly acute. Embodiments of the technology may be applied to sites where bifurcating arteries diverge widely or acutely. For practical descriptive purposes in this application, several examples of bifurcating vessels will be shown and described as extending laterally generally orthogonal with respect to the parent vessel. The closure structure can also have a longitudinal aspect "g" (FIG. 1C) generally aligned with the longitudinal axis L-L of the device as a whole and of the supplemental stabilizer. As will be described below, the closure structure has elements that extend longitudinally and proximally to connect to the proximal support framework.

C. Selected Embodiments of the Technology

Figure 1C:
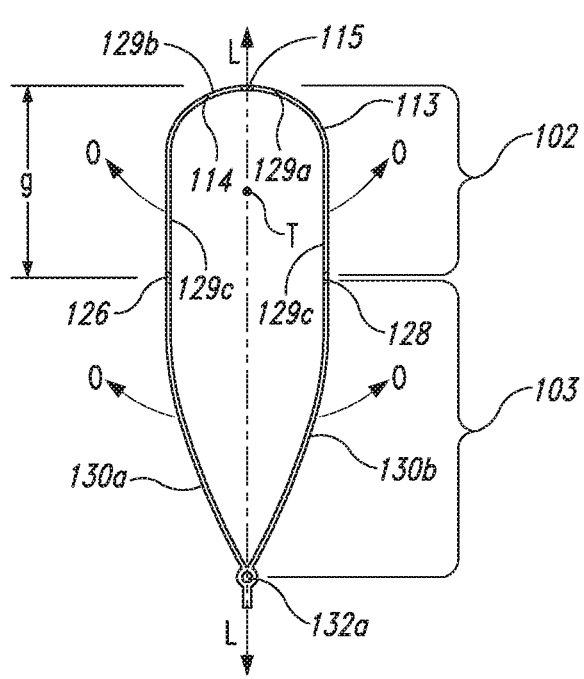
Figure 1D:
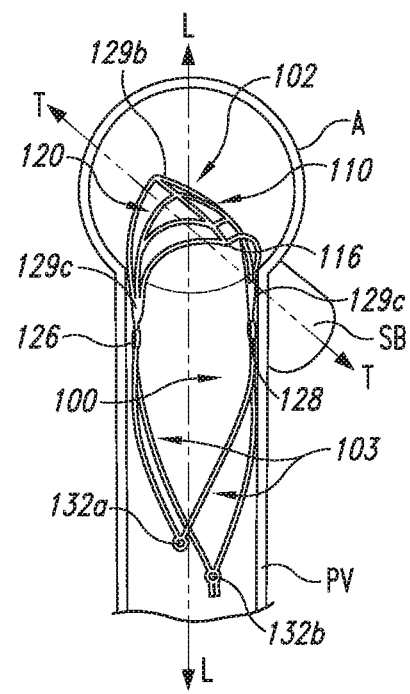

FIGS. 1A-1D illustrate an embodiment of an implantable aneurysm device 100 configured in accordance with the present technology. FIG. 1A is a top plan view of the aneurysm device 100 in a substantially flat, pre-assembled configuration, FIG. 1B is an isometric view of the aneurysm device 100, FIG. 1C is a side view of the aneurysm device 100, and FIG. 1D is an isometric view of the aneurysm device 100 shown in a cutaway portion of the anatomy. Referring to FIG. 1A, the aneurysm device 100 can comprise a closure structure 102 and a supplemental stabilizer or support 103 extending from the closure structure 102. The closure structure 102 can be a frame, scaffold, or other structure that at least partially occludes the neck of an aneurysm to prevent embolic coils or other coagulative material within the aneurysm from escaping into the bloodstream. The supplemental stabilizer 103 is shown in an unassembled stage in FIG. 1B. Once assembled, the proximally extending sides of the closure structure 102 and the supplemental stabilizer 103 hold the curved portion of the closure structure 102 at the neck of the aneurysm.

In the embodiment shown in FIGS. 1A-1D, the closure structure 102 comprises a rhombus-like framework or scaffold including a perimeter support 110 and an inner support 120. The perimeter support 110 can include struts 111, 112, 113, and 114 joined together at corners 115, 116, 117, and 118. The corners 115 and 116 can be lateral corners defining a lateral aspect of the closure structure 102 that extends along the lateral axis T-T, and the corners 117 and 118 can be longitudinal corners that define the proximal end of the closure structure 102. The inner support 120 can similarly include struts 121, 122, 123, and 124 The inner support 120 of the embodiment of the aneurysm device 100 illustrated in FIG. 1A is connected to the perimeter support 110 by lateral connector struts 119*a* and 119*b* and longitudinal connector struts 125*a* and 125*b*. The embodiment of the closure structure 102 illustrated in FIG. 1A is generally symmetrical with respect to the centerlines of both the longitudinal and lateral axes, but in other embodiments the closure structure 102 may have an asymmetrical configuration with respect to either or both of the longitudinal and lateral axes (e.g., see FIGS. 6A-8D).

Although the corners 115, 116, 117, and 118 are illustrated as being pointed, other embodiments of the corners may have a more rounded profile, a more complex curve, or other angular configurations. The perimeter support 110, inner support 120, lateral connector struts 119*a-b*, and longitudinal connector struts 125*a-b* may be formed integrally with one another from a sheet of material, or separate struts may be formed and bonded together at the corners.

In the embodiment illustrated in FIG. 1A, the aneurysm device 100 is constructed from a substantially flat substrate by cutting, etching, stamping, or otherwise forming the framework of the closure structure 102 and the unassembled supplemental stabilizer 103. The closure structure 102 and the supplemental stabilizer 103 can be constructed from a flat sheet of material having substantially uniform thickness, but in other embodiments different regions of the sheeted material can have different thicknesses corresponding to the desired thickness for portions of the closure structure 102 and/or the supplemental stabilizer 103. As explained in more detail below with respect to FIGS. 13A and 13B, for example, the thickness of the closure structure 102 can be thinner in areas near the lateral axis T-T compared to other regions of the closure structure 102 and the supplemental stabilizer 103.

Referring to FIGS. 1B and 1C, the closure structure 102 can be folded or bent into a curve along the lateral axis T-T such that the portions of the closure structure 102 associated with corners 117 and 118 define paired longitudinally aligned structures on either side and generally substantially orthogonal to the lateral axis T-T. The paired longitudinally aligned structures can be substantially parallel to each other and define anchors that hold the closure structure 102 in place. The closure structure 102 forms a vertex that is resiliently bent by a total of about 180.degree. and is biased outward (arrows O in FIG. 1C). The outward bias of the closure structure 102 is due to the materials that form the closure structure, such as resilient metals or alloys including Nitinol and other shape memory metals. The outward biasing force O is conveyed to the supplemental stabilizer 103 from the closure structure 102 such that the supplemental stabilizer 103 presses outward against the lumen of a parent vessel that extends at an angle relative to the lengthwise dimension of the closure structure 102. This structural arrangement and planar-defined outwardly directed biasing force is different from the structural arrangement and outwardly directed force generated by a conventional stent. More specifically, stents generate a radially outward-directed force from the central longitudinal axis of the stent (e.g., a hoop force) as opposed to the lateral axis of the device that resides at an angle to the parent vessel.

FIGS. 1B and 1C also illustrate an embodiment of the supplemental stabilizer 103. In this embodiment, the supplemental stabilizer extends proximally from a first junction 126 and a second junction 128. The supplemental stabilizer 103 can include struts 130*a-d*. More specifically, struts 130*a* and 130b can be connected together at a proximal joint 132a, and struts 130c and 130d can be connected together at a second proximal joint 132b.

The closure structure 102 can define a distal framework portion, and the supplemental stabilizer 103 can define a proximal framework portion. Each of these portions can have first and second pairs of struts. With regard to the first and second pairs of struts of the distal framework portion, a distal end of each strut of the first pair is joined to a distal end of a strut of the second pair at a lateral apex, and distal-facing aspects of the first and second pairs of struts collectively form an outline configured to substantially conform to the neck of an aneurysm. As shown in FIG. 1B, the struts 111-114 and 121-124 of the inner and perimeter supports can curve inwardly toward the longitudinal axis L-L of the aneurysm device 100. The outline of the supports 110 and 120 is typically that of a quadrilateral form. In some embodiments, the supports 110 and 120 can have a rhombus-like configuration or diamond shape. The supports 110 and 120 can be symmetrical (e.g., the same length along orthogonal axes) or asymmetrical in which one side of the rhombus-like structure can have an axis longer than the other side. Although many closure structures 102 described below have quadrilateral forms, the closure structures 102 are not limited to these shapes in that the distal-facing aspect of the distal framework portion may have other shapes, such as polygons or polygonal curvilinear shapes. In several embodiments, the rhombus-like supports 110 and 120 are concentric with a center at the longitudinal axis L-L of the aneurysm device 100. The lateral apices of the closure structure 102 are disposed at opposing ends of the lateral axis of the distal framework portion. The two portions of the distal framework portion opposite each other across the longitudinal axis may define lateral leaves of the distal framework portion. The proximal ends of the first pair of struts converge approximately to form the first junction 126, and the proximal ends of each second pair of struts converge approximately to form the second junction 128.

FIGS. 1B and 1C, more specifically, are respectively an isometric view and a side view of the aneurysm device 100 in a deployed configuration. In the deployed configuration, the closure structure 102 has a distally projecting arch defined by a curved section of the distal framework portion that curves around the lateral axis T-T. The supplemental stabilizer 103 extends proximally from the closure structure 102 at an angle relative to the lateral axis T-T. Referring to FIG. 1C, a proximal-facing aspect 129a of the arch of the closure structure 102 extends over the lumina of the bifurcating arteries. A distal-facing aspect 129b of the arch of the closure structure 102 generally presses against the luminal surfaces of the bifurcating arteries. The closure structure 102 can have sides 129c that extend down into the parent artery and press outwardly against the luminal surface thereof. The proximal-facing aspect 129a of the arch is generally and substantially transverse (e.g., perpendicular or other non-zero angles) to the longitudinal axis L-L. The arch expands unobtrusively over the lumina of the bifurcating arteries without forming an incursion into the vascular flow path. More particularly, the arch is not an enclosed opening or hole; rather, it is an entirely open structure facing in the proximal direction along the longitudinal axis L-L.

FIG. 1D is an isometric view of the aneurysm device 100 implanted at a target site of an aneurysm A located along side branch vessels SB(only one shown in FIG. 1D) that extend transverse to a parent vessel PV. The distal-facing aspect 129a of the closure structure 102 is configured to substantially align with or otherwise conform to the neck of the aneurysm A by forming a curved surface that compatibly aligns with or engages the neck and the surrounding wall of the side branch vessels SB. In some embodiments, the distal-facing aspect 129a has a complex curve, such as a hyperbolic paraboloid (e.g., a generally saddle-shaped form) .As described above, the closure structure 102 typically includes a quadrilateral distal aspect having a rhombus-like shape that extends at least partially across the neck of the aneurysm A. Two of the apices of the quadrilateral frame are at opposite ends of the lateral axis T-T such that the lateral aspect "1" of the closure structure 102 extends along the longitudinal dimension of the side branch vessels SB. The other two apices of the quadrilateral frame extend parallel to each other along the longitudinal axis L-L within the parent vessel PV. As described in more detail below, the closure structure 102 can have a saddle-shape in which the two sets of opposing apices are curved in opposite directions.

Referring to FIG. 1D, the two apices defined by the corners 117 and 118 at the sides 129c of the closure structure 102 can terminate at first and second junctions 126 and 128. The two apices defined by the corners 117 and 118 are at opposite ends of the sides 129c of the curve and extend proximally within the parent vessel and form an anchoring mechanism in which the lateral sides 129c exert an outward force O (FIG. 1C) against the lumen of the parent vessel PV. The two apices defined by the corners 115 and 116 at the ends of the lateral aspect "1" of the closure structure 102 extending along the lateral axis T-T in the side branching vessels are generally curved distally so they press upward against the distal aspect of the lumina of the side branching vessels. The disposition of the transverse apices 115 and 116 of the closure structure 102 and the side branching vessels, their orientation, length, and symmetry may vary among different embodiments as described in more detail below.

The orientation as well as the length of the lateral aspect of the closure structure 102 that extends along the lateral axis T-T can have forms other than those of a hyperbolic paraboloid. For example, the lateral apices may be deflected downward (proximally), or in other embodiments one lateral apex may be deflected proximally while the other is deflected distally. All such variations are included in the embodiments and will be understood to be designed to conform to the particular dimensions and anatomical features of the targeted aneurysm site.

One embodiment of an aneurysm enclosure device configured in accordance with the present technology includes a framework in its planar configuration prior to being folded and having longitudinal ends joined to form an assembled configuration such as that described above. This planar and pre-folded embodiment of an aneurysm enclosure framework includes a central framework portion (to become the distal framework in the assembled configuration) and two support framework portions (to become, collectively, the proximal support framework in the assembled configuration). In this planar embodiment, a central framework portion and two support framework portions (a first and a second) are connected to opposite sides of the central framework portion, the central and support framework portions aligned along a longitudinal axis.

The central framework portion includes at least one set of central struts forming at least one quadrilateral form, with two lateral junctions joining the struts at apices of a lateral axis, and first and second longitudinal junctions joining the struts at two longitudinal apices. The lateral axis of the planar configuration will become the central axis of the distal-facing aspect of the distal framework portion of the assembled configuration. The two longitudinal apices of the central framework will become the proximal apices of the distal framework of the assembled configuration. The first and second longitudinal junctions are sites that also serve to join the central framework, respectively, to the first and second support framework portions.

Returning to the quadrilateral form created by the central struts and the two lateral junctions and the two longitudinal junctions, in some embodiments, the form may be described as generally having a rhombus shape or diamond shape in that the lateral axis can be longer than the longitudinal axis. However, the relative length of the longitudinal axis and of the lateral axis varies among embodiments of the technology, according to the specifics of the aneurysm site for which the device is intended. Further, while the longitudinal halves of the central framework portion (on either side of the lateral axis) are generally symmetrical, the lateral halves of the central framework portion (on either side of the longitudinal axis) may be symmetrical or asymmetrical. In the latter case the quadrilateral has a form like a kite, in which the longitudinal axis of the kite is likened to the lateral axis of distal framework. Variations in lateral symmetry may be tailored to the specifics of the aneurysm site for which the device is intended.

Each of the two proximal support framework portions, a first portion and a second portion, has a pair of support struts, thus there is a first pair and a second pair of support struts. Each proximal support strut has an internal end and a peripheral end. The struts of the first pair are connected together at their internal ends to the first longitudinal junction, the struts of the second pair are connected together at their internal ends to the second longitudinal junction, and each set of support struts spreads outward from their respective longitudinal junction at an angle that ranges between about 30 degrees and about 90 degrees.

These outwardly extending strut ends are a particular feature related to the configuration of the device and the transition from a planar configuration to an assembled configuration. To form the assembled configuration of the device, the free external or longitudinal ends of the struts of the support framework are joined together. More particularly, the planar framework has two lateral halves (divided by the longitudinal axis), thus each of the two external framework portions has one strut extending on each lateral half. The struts on each of the opposite support framework portions that are on the same lateral half of the device are those that are joined together to create the folded configuration. Joining of strut ends may be by any conventional method, e.g., welding, soldering, or bonding.

Returning now to features of a basic embodiment of the implantable device, a proximal-facing aspect of the distal framework forms a curved surface, more particularly, an arch or an arched profile that spans over the lumina of the bifurcating arteries. The distal-facing aspect or back of the proximal-facing surface generally aligns against the luminal surfaces of the bifurcating arteries, the sides of the arch extending down into the parent artery and aligned against the luminal surface thereof. The proximal face of the arch is generally and substantially transverse (perpendicular or orthogonal) to the lateral axis of the proximal framework. The arch spans unobtrusively over the lumina of the bifurcating arteries, forming no incursion into the vascular flow path. More particularly, the arch is not an enclosed opening or hole, it is a structure entirely open in the proximal direction.

As will be described further below, the enclosure can be a distal framework portion made from an originally planar metal sheet that is etched or cut into a framework that is folded or bent into a curve along its lateral axis by about 180 degrees, such that the paired longitudinally aligned structures (on either side of the lateral axis and orthogonal to it) become substantially parallel to each other. As such, the central lateral axis of the distal framework forms a vertex, resiliently bent by a total of about 180 degrees, and which is thus biased to return to its originally planar form. Resilience of this vertex is due to the materials that form the framework, typically resilient metals or alloys, such as Nitinol, as described further below. It is this biased force, defined by planes that include the linear vertex represented by the lateral axis of the distal portion of the framework, which is conveyed to the proximal support framework from the distal framework to which it is connected that causes the proximal support framework to press outward against the lumen of the parent artery. Notably, this structural arrangement and planar-defined outwardly-directed force mechanism is different from the structural arrangement and outwardly-directed force that would be provided by a stent, which if disposed within the parent artery, would generate a radially outward directed force from the central longitudinal axis of the stent.

The distal framework, as mentioned above, also includes a distal-facing aspect that is configured to substantially align with or conform to the neck of the target aneurysm by assuming a curved surface that compatibly aligns with or engages the neck and surrounding locale of the aneurysm. In some embodiments, the surface represented by the distal face of the framework assumes a complex curve, such as, by way of example, a hyperbolic paraboloid or generally saddle-shaped form. The distal framework typically includes a quadrilateral distal aspect having a rhombus-like shape or diamond shaped form in some embodiments. Two of the apices of the quadrilateral frame are at opposite ends of the lateral axis (as described above), and two apices are at opposite ends of the longitudinal axis (as described above). The saddle-shape is one in which the two sets of opposing apices are curved in opposite directions from an original plane prior to deformation into the saddle shape.

The two apices at opposite ends of the longitudinal axis are typically curved proximally, forming an anchoring mechanism having lateral sides or faces, which are generally directed into and urged against the lumen of the parent artery. And the two apices at opposite ends of the lateral axis are generally curved distally, so they press upward against a distal aspect of the lumina of the side branching arteries. The disposition of these lateral apices, their orientation, length, and symmetry, may vary among embodiments, as described further below.

The orientation (as well as length) of the lateral portions of the distal frame can vary and assume forms other than those of a hyperbolic paraboloid. In some embodiments, the lateral apices may be deflected downward (proximally), and in some embodiments, one lateral apex may be deflected proximally, and the other distally. All of these variations are included as embodiments, such variations available in order to conform to the particular dimensions and configuration of targeted aneurysm sites.

Figures 1E, 1F:
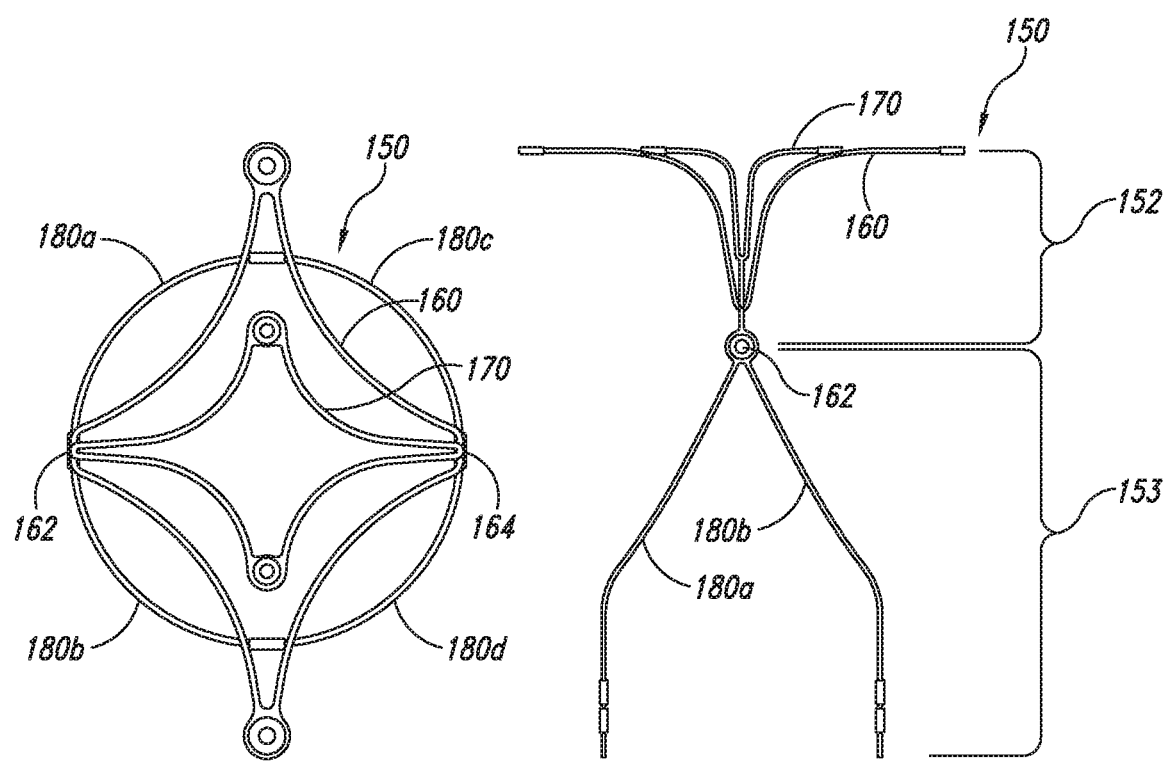
FIGS. 1E-1H are views of an aneurysm device configured in accordance with another embodiment of the technology.
Figures 1G, 1H:
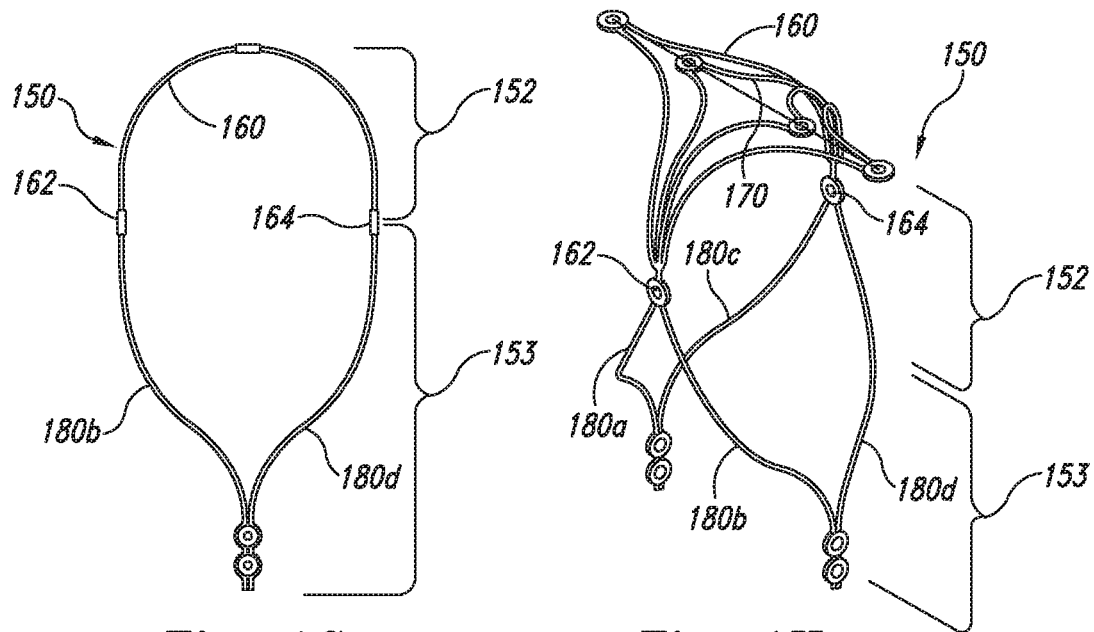

FIGS. 1E-1H illustrate another embodiment of an aneurysm device 150 of the present technology. In particular, FIG. 1E shows a top view of the device 150, FIGS. 1F and 1G are front and side views, respectively, of the device 150, and FIG. 1H is an isometric view of the aneurysm device 150 in an assembled configuration. The aneurysm device 150 can include a number of features similar to the aneurysm device 100 described above with respect to FIGS. 1A-1D. For example, the aneurysm device 150 comprises a closure structure 152 and a supplemental stabilizer or support 153 extending from the closure structure 152. The closure structure 152 includes a perimeter support 160 and an inner support 170 As best seen in FIG. 1E, the supports 160 and 170 can have a rhombus-like (e.g., diamond-shaped) shape or configuration. The perimeter support 160 and inner support 170 can be joined at junctions 162 and 164. The perimeter and inner supports 160 and 170 can have struts similar to those described above regarding FIGS. 1A-1D. However, the aneurysm device 150 does not have lateral or longitudinal connector struts between the inner and perimeter structures 160 and 170.

The aneurysm device 150 can also have struts 180a-d projecting proximally from the junctions 162 and 164. In the configuration shown in FIGS. 1E-1H, struts 180a-b are connected at junction 162 and struts 180c-d are connected at junction 164 to form the supplemental stabilizer 153 with proximal anchoring segments. The struts 180 of the implantable device 150 shown in FIGS. 1E-1H are similar to the device 100 shown in FIGS. 1A-1D but, as best seen in FIG. 1G, the struts 180 have a different radius of curvature than the struts 130 of the device 100.

Figure 2E:
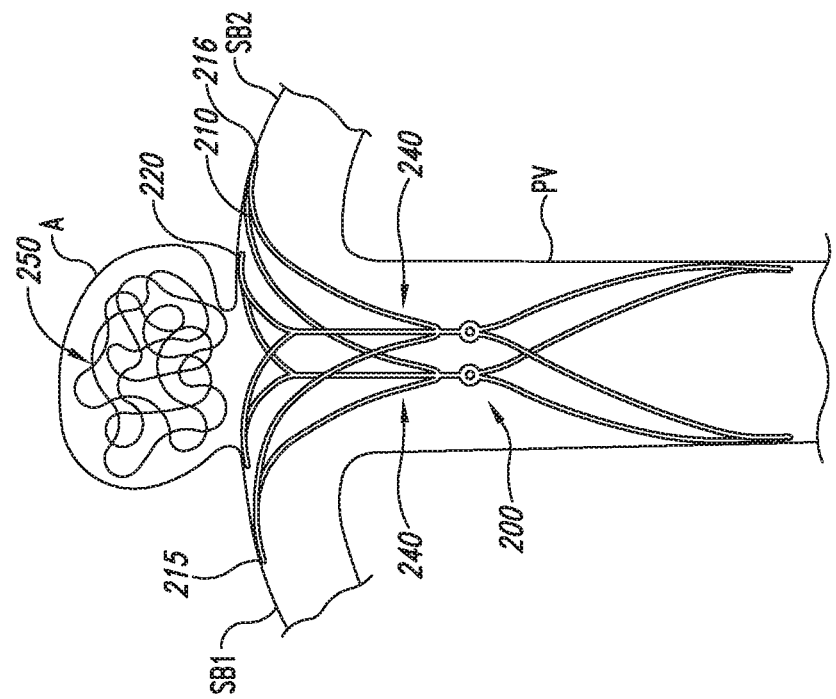
FIGS. 2D and 2E are views of the aneurysm device of FIGS. 2A-2C implanted at different aneurysms.
Figure 2D:
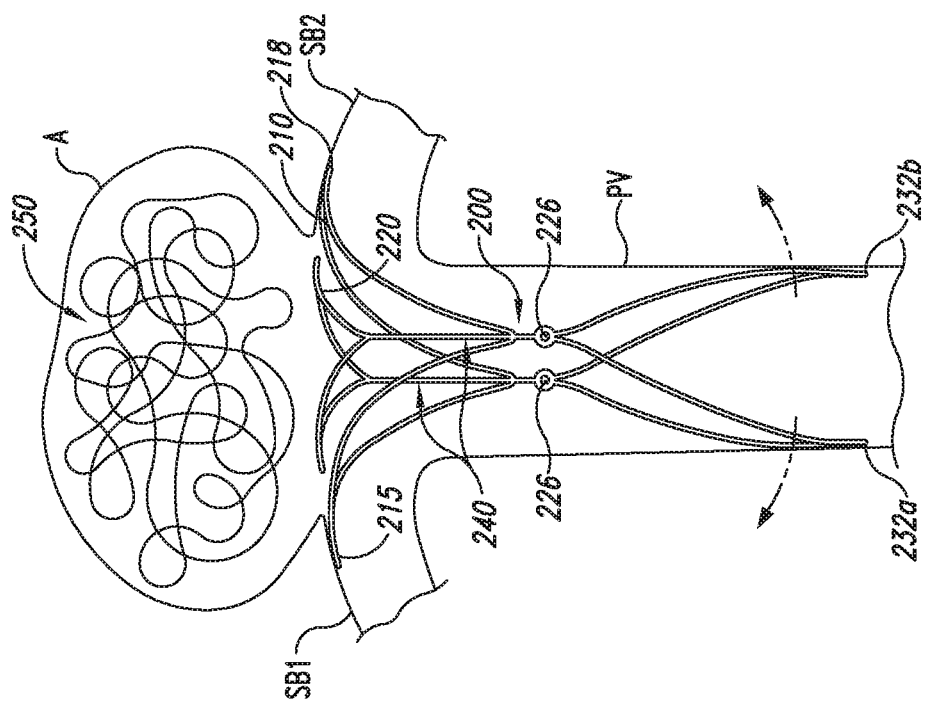

FIGS. 2A-2E schematically illustrate another embodiment of an aneurysm device 200 of the present technology. FIG. 2A shows a plan view of the aneurysm device 200 in a substantially flat, pre-assembled condition; FIGS. 2B and 2C show the aneurysm device 200 in different perspective side views; and FIGS. 2D and 2E show the aneurysm device 200 deployed across the neck of an aneurysm A. The aneurysm device 200 comprises a closure structure 202 having a perimeter support 210 and an inner support 220. The supports 210 and 220 can have a rhombus-like shape (e.g., diamond-shaped) configuration in a pre-assembled, flat condition shown in FIG. 2A. The perimeter support 210 and inner support 220 can be joined at junctions 226 and 228. The perimeter and inner supports 210 and 220 can have struts similar to those described above regarding FIGS. 1A-1D. However, the aneurysm device 200 does not have lateral or longitudinal connector struts between the perimeter and inner structures 210 and 220.

The aneurysm device 200 may be constructed from the pre-assembled form of FIG. 2A to the assembled form illustrated in FIG. 2B simply by folding the device to rotate the terminal junctions 226 and 228 toward one another and form a substantially inverted U-shaped configuration having a curved distal portion as described above with reference to FIGS. 1B and 1C. The device 200 can also have struts 230a-d projecting proximally from the junctions 226 and 228. In the assembled configuration, struts 230a-b are connected at junction 232a and struts 230c-d are connected at junction 232b to form a supplemental stabilizer with proximal anchoring segments. The aneurysm device 200 shown in FIGS. 2A-2C is similar to the device 100 shown in FIGS. 1A-1D, but the device 200 lacks support connecting the perimeter support 210 to the inner support 220.

FIGS. 2D and 2E illustrate the aneurysm device 200 of FIGS. 2A-2C deployed cross the neck of an aneurysm A with anchoring legs 240 defined by the proximal sides of the closure structure 202 and proximal anchoring segments defined by the struts 230a-d contacting the wall of parent vessel PV. The device, when deployed, does not obstruct flow in parent vessel PV or either of the side branch vessels SB1 and SB2. FIG. 2D illustrates a deployment and an aneurysm having a relative wide neck. In this deployment, lateral corners 215 and 216 of the perimeter support 210 are deployed to contact the neck of the aneurysm and/or vessel wall in proximity to the neck of the aneurysm, while the inner support 220 is substantially or entirely within the opening formed by the neck of the aneurysm. FIG. 2E illustrates a deployment across an aneurysm having a relatively narrow neck in which lateral corners of both the perimeter support 210 and the inner support 220 are deployed to contact at least a portion of the neck of the aneurysm and/or vessel wall in proximity to the neck of the aneurysm.

FIGS. 2D and 2E additionally illustrate the use of aneurysm device 200 to retain debris and/or other materials, such as an embolic coil mass 250, within the aneurysm cavity. In one embodiment, implantable devices of the present technology may be deployed to retain debris and/or previously placed materials within the aneurysm cavity. In another embodiment, implantable devices of the present technology may be deployed before placing materials, such as embolic materials, coils, and the like, in the aneurismal cavity, and then the materials may be placed through the openings in the closure structure 202. In this situation, the aneurysm device 200 may be retracted following placement of the embolic materials, or it may be detached and left at the site.

FIGS. 3A-3C show additional embodiments of implantable aneurysm devices 300a-c of the present technology similar to the aneurysm device 200 illustrated in FIGS. 2A-2E, but the aneurysm devices 300a-c have different, more complex curved profiles. Each of the aneurysm devices 300a-c has a closure structure 302 and a supplemental stabilizer 303. The closure structure 302 of the aneurysm device 300a in FIG. 3A has lateral corners 315a-b and 316a-b that curve upwardly (e.g., distally). Referring to FIG. 3B, the closure structure 302 of the aneurysm device 300b has lateral corners 315a-b and 316a-b that curve downwardly (e.g., proximally). The closure structure 302 of the aneurysm device 300c shown in FIG. 3C has a first set of lateral corners 315a-b that curve upwardly (e.g., distally) and a second set of lateral corners 316a-b that curve downwardly (e.g., proximally). Both the perimeter support and internal support of the closure structures of aneurysm devices configured in accordance with the present technology may have a variety of simple or complex curves and configurations, and thus the foregoing examples are merely illustrative.

Figure 4D:
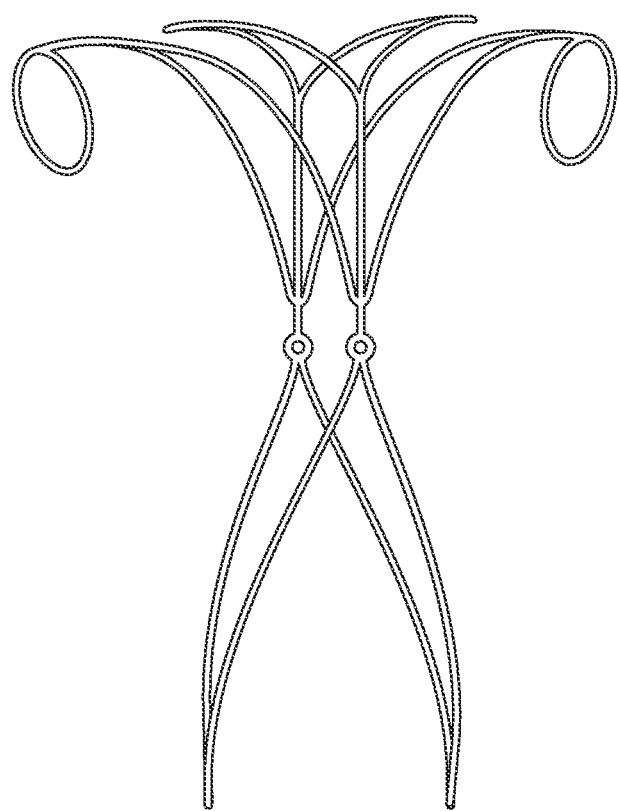
FIG. 4D is a view of the aneurysm device configured in accordance with an embodiments of the technology.

FIGS. 4A-4C illustrate the aneurysm devices 300a-c of FIGS. 3A-3C implanted at different aneurysm target sites A. The curvature and configuration of the perimeter support and inner support of the closure structures 302 of these different devices 300a-c accommodate different aneurysm configurations and locations, different side branch vessels SB1 and SB2, different parent vessel PV locations and configurations, and the like. Referring to FIG. 4A, the device 300a is well suited for anatomical structures in which the first and second side branch vessels SB1 and SB2 extend from the parent vessel PV at an angle α greater than 90° because the lateral corners 315a-b and 316a-b curve distally and radially expandable rings at lateral corners 316a-b expand within the first and second side branch vessels SB1 and SB2. Conversely, the device 300b shown in FIGS. 4B is well suited for anatomical structures in which the side branch vessels SB1 and SB2 extend at an angle .alpha. less than 90° relative to the longitudinal axis of the parent vessel PV because the lateral corners 315a-b and 316a-b project proximally and radially expandable rings at lateral corners 316a-b expand within the first and second side branch vessels SB1 and SB2. The device 300c shown in FIG. 4C and FIG. 4D is well suited for situations in which one side branch vessel SB1 projects at an angle a greater than 90° and the other side branch vessel SB2 projects at an angle β less than 90° because the first set of lateral corners 315a-b project distally and the second set of lateral corners 316a-b project proximally and radially expandable rings at lateral corners 316a-b expand within the first and second side branch vessels SB1 and SB2.

Figure 5B:
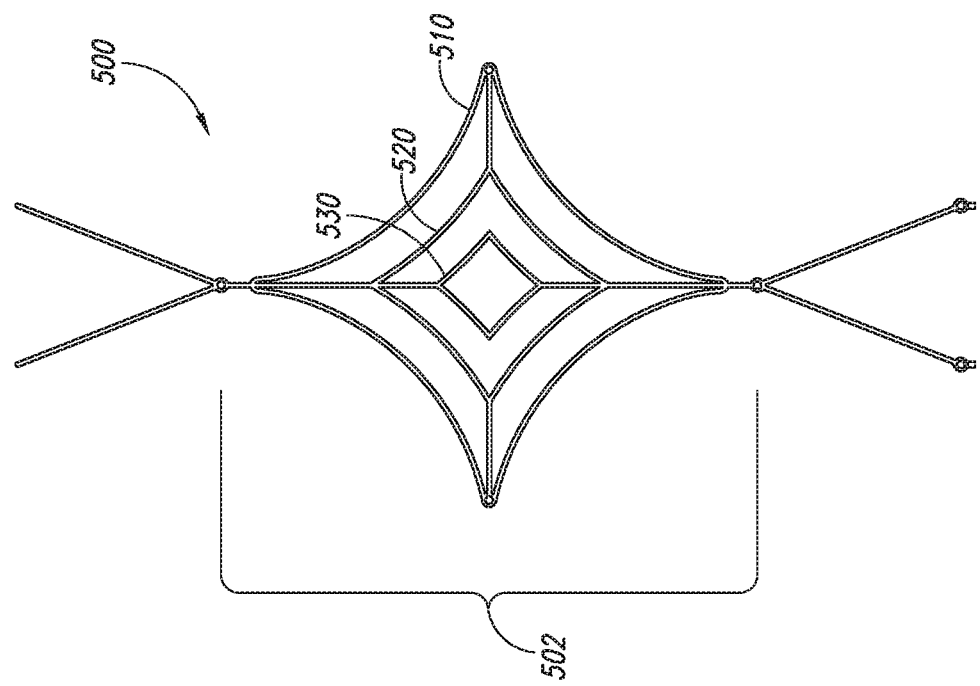
Figure 5A:
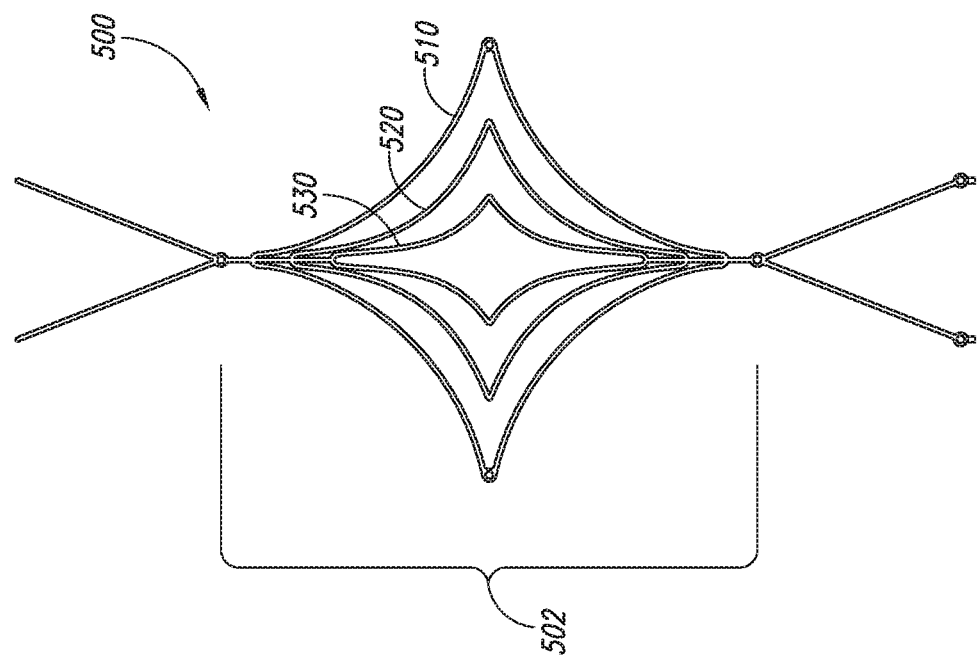
Figure 5H:
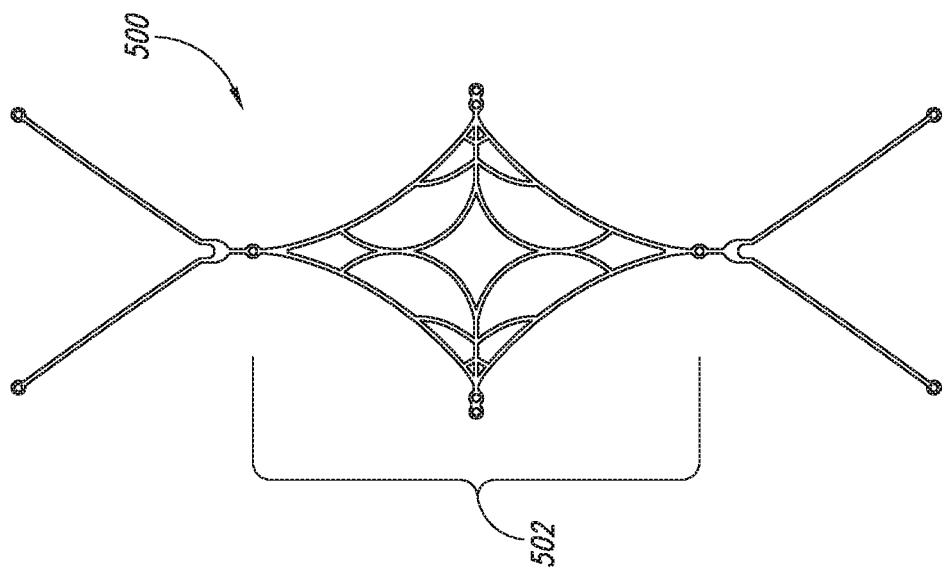
Figure 5G:
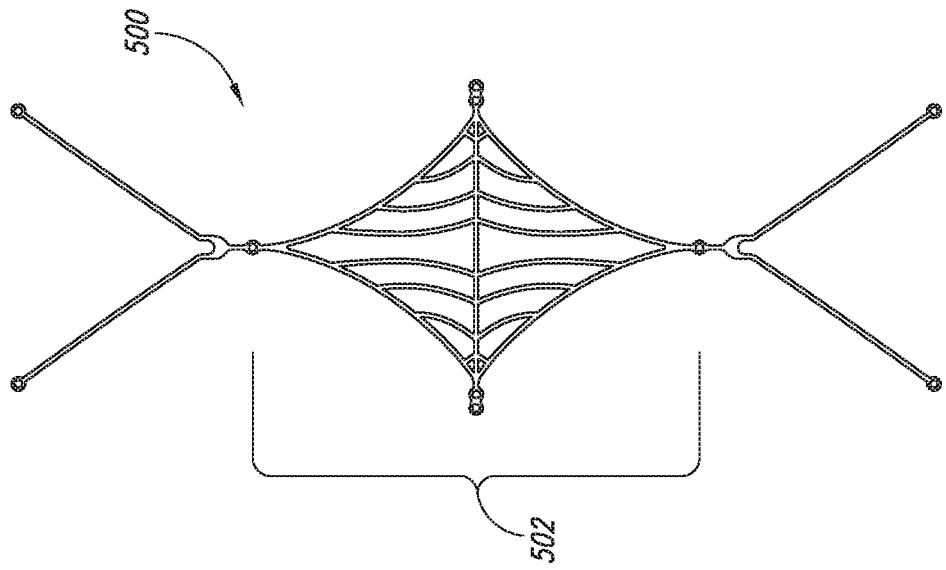
Figure 5F:
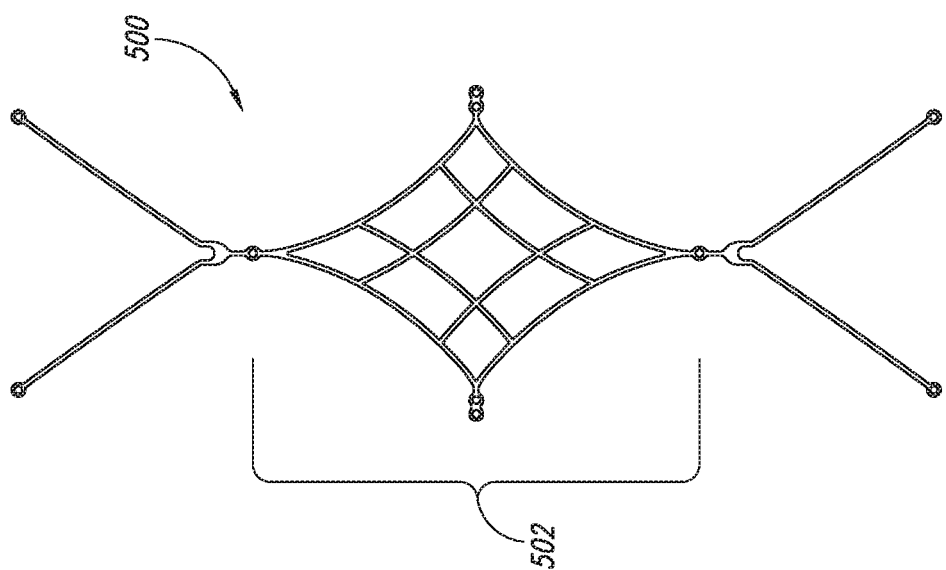

FIGS. 5A-5H are top plan views illustrating a plurality of different embodiments of aneurysm devices 500 configured in accordance with the technology. Each of the aneurysm devices illustrated in FIGS. 5A-5H are shown in a substantially flat, pre-assembled format, and they are in addition to the embodiments of the aneurysm devices 100-300c illustrated in FIGS. 1A-4C. The aneurysm devices 500 include various configurations of closure structures 502. For example, the closure structures 502 illustrated in FIGS. 5A and 5B have three supports 510, 520, and 530 configured to extend across the neck of an aneurysm. FIGS. 5C-5H illustrate additional embodiments with support structures configured to extend across at least a portion of the neck of an aneurysm. However, instead of having one support structure within another support structure as shown in FIGS. 5A-5B, the struts forming the supports of the closure structures 502 illustrated in FIGS. 5C-5H can be interconnected.

Some embodiments of the distal framework portion have more than one set of distal first and second pairs of struts in which case the pairs of struts typically form rhombus-or diamond-shaped structures within each other. By way of example, a perimeter rhombus-shaped form may include within it one or more smaller rhombus-shaped forms arranged in an external-internal hierarchy. In some embodiments of the distal framework, the framework may further include longitudinally aligned extension elements that extend distally from the distal junction and give rise proximally to bifurcating struts that form rhombus-shaped frame portions. These rhombus shapes mounted at the ends of extension elements are typically rhombi that are internal with respect to more external surrounding rhombi, and the rhombus-shaped structures collectively form the distal-facing aspect of the distal framework. With respect to size and general dimensions, the perimeter or external rhombus-shaped forms generally are sized to approximate the dimensions of the neck of the target aneurysm, and when implanted, these rhombi generally align with the neck but do not necessarily make direct contact. The internal rhombus-shaped forms are thus generally smaller than the neck of the aneurysm and are disposed across the face of the aneurysm within the bounds of the neck.

FIGS. 6A and 6B illustrate embodiments of asymmetric aneurysm devices 600a and 600b, respectively, that each include a closure structure 602 and a supplemental stabilizer 603. The closure structure 602 of the aneurysm device 600a illustrated in FIG. 6A has a perimeter support 610 and an inner support 620. The perimeter support 610 has major struts 612 and minor struts 614, and the inner support 620 has major struts 622 and minor struts 624. The inner support 620 can be connected to the perimeter support 610 by links or connector struts 626a-b. The major struts 612 and 622 have a first length d.sub.1, and the minor struts 614 and 624 have a length d.sub.2 less than the length d.sub.1. As a result, the aneurysm device 600a has a first side 631 longer than a second side 632.

Referring to FIG. 6B, the aneurysm device 600b also has a perimeter support 610 and an inner support 620. In addition to the connector struts 626a-b of the aneurysm device 600a, the aneurysm device 600b further includes connector struts 627a-b extending along the lateral dimension of the closure structure 602.

Figure 7B:
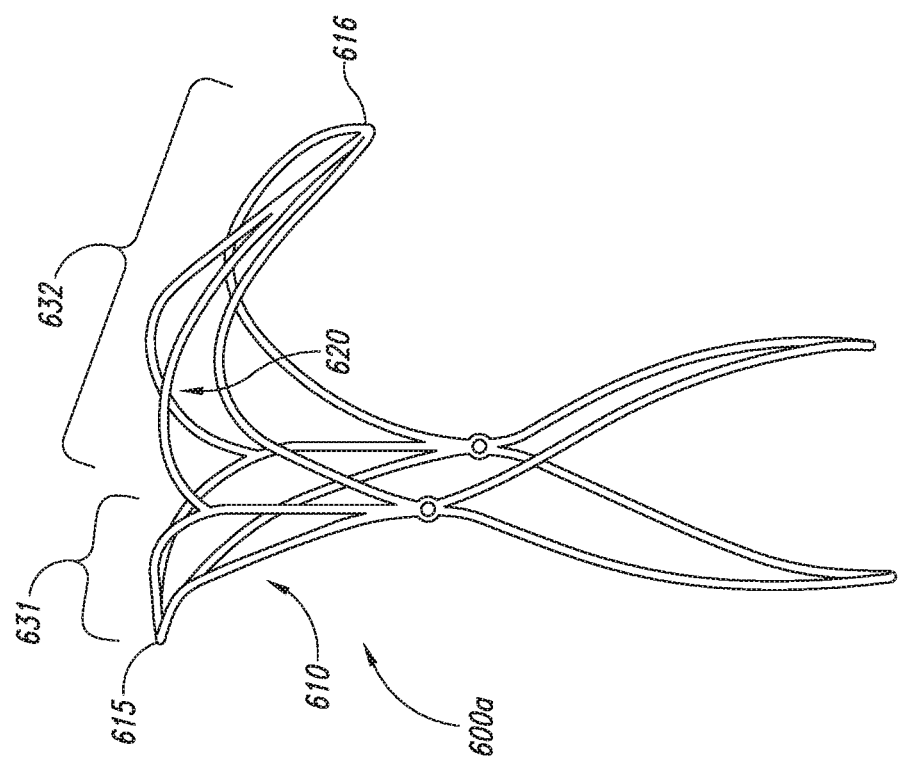
FIGS. 7A and 7B are views of the asymmetric aneurysm devices of FIGS. 6A and 6B in a deployed configuration.
Figure 7A:
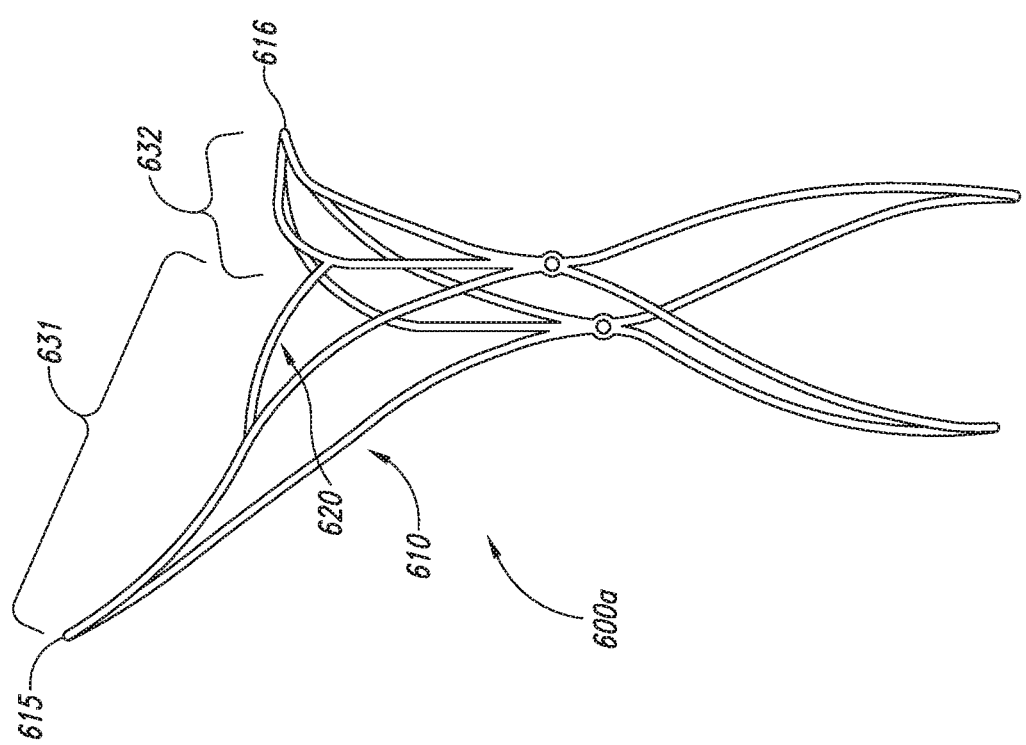

FIGS. 7A and 7B illustrate devices formed from the template illustrated in FIG. 6A. Referring to FIG. 7A, the first side 631 of the aneurysm device 600a can be longer and project upwardly (distally). The lateral corner 615 associated with the first side 631 is accordingly more distal than the lateral corner 616 of the second side 632. Referring to FIG. 7B, the second side 632 of the aneurysm device 600a is longer than the first side 631, and the lateral corner 616 of the second side 632 is positioned proximal relative to the lateral corner 615 of the first side 631. FIGS. 6A-7B accordingly show several embodiments of asymmetric aneurysm devices, but additional embodiments are included within the scope of the technology.

Figure 8A:
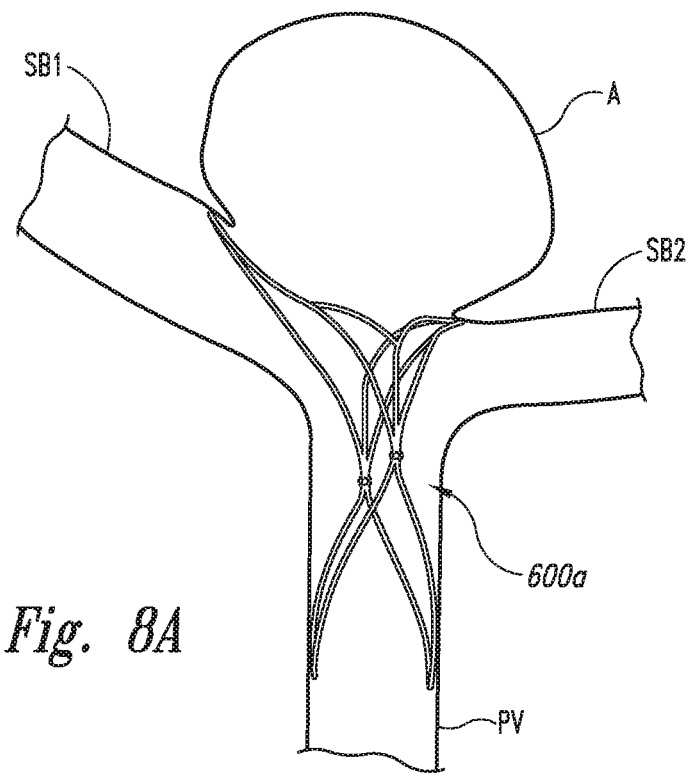
FIGS. 8A and 8B are views of the asymmetric aneurysm devices of FIGS. 7A and 7B implanted at aneurysms.
Figure 8B:
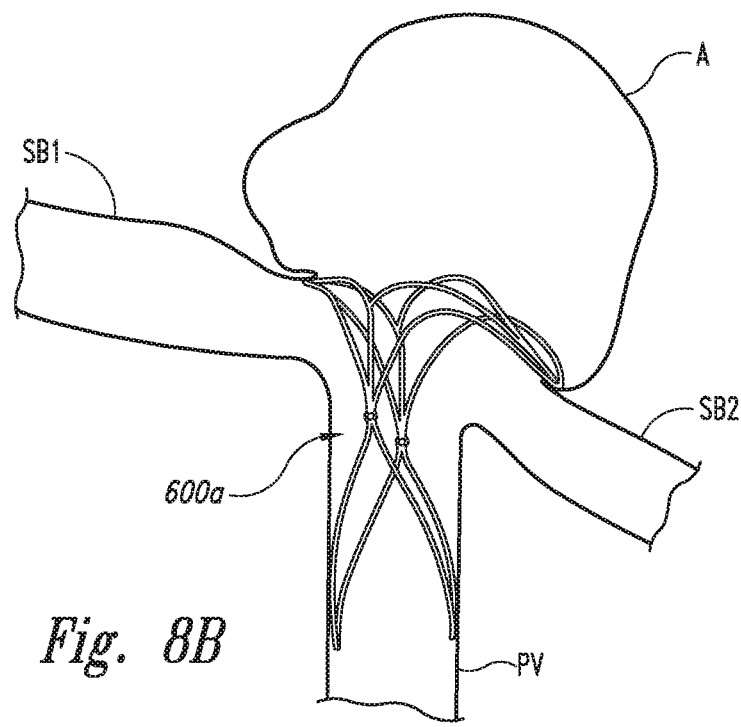

FIGS. 8A and 8B illustrate the aneurysm devices 600a of FIGS. 7A and 7B deployed across the neck of aneurysms having different geometries and neighboring vessel configurations. Such asymmetrical designs are suitable for applications where one aneurysm device would not be sufficient to completely bridge the neck of an aneurysm. As explained in more detail below, the aneurysm devices would generally be used in conjunction with a leading wire for precise orientation and deployment. In multiple device embodiments, a first aneurysm device is deployed such that it is anchored along a specific portion of the aneurysm neck, and then a second aneurysm device required to bridge the rest of the aneurysm neck is positioned such that the closure structure of the second device overlaps a portion of the closure structure of the first device and bridges the remaining portion of the aneurysm neck.

Figure 9:
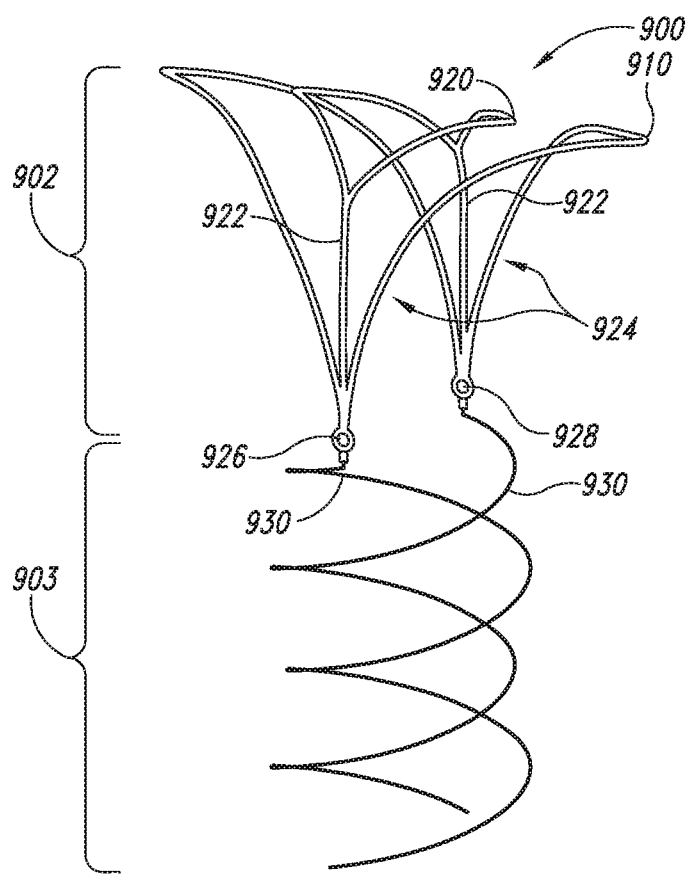
FIG. 9 is a view of an aneurysm device configured in accordance with another embodiment of the technology.

FIG. 9 is an isometric view of an embodiment of yet another aneurysm device 900 configured in accordance with the technology. In this embodiment, the aneurysm device 900 has a closure structure 902 with a perimeter support 910 and an inner support 920 that are joined by connector struts 922. The connector struts 922 and the proximally extending portions of the supports 910 and 920 define an anchoring mechanism 924 that extends to junctions 926 and 928 and is configured to exert an outward force against the parent vessel (not shown in FIG. 9). The aneurysm device 900 further includes a supplemental stabilizer 903 that includes at least one helical anchoring segment 930 projecting proximally from at least one of the junctions 926 or 928. The embodiment of the aneurysm device 900 shown in FIG. 9 has a helical anchoring segment 930 extending from each of the junctions 926 and 928. The aneurysm device 900 provides a framework that can be delivered endovascularly to a target site proximate an aneurysm near a terminus of a parent artery with bifurcating downstream arteries. The framework, when expanded at the target site, includes a distal framework portion comprising a distal-facing aspect configured to enclose the aneurysm and a proximal-facing aspect configured to arch over lumina of the downstream arteries. The framework also includes a proximal support framework connected to the distal framework portion that comprises a spiral configured to reside in the parent artery and biased to radially expand against the wall thereof.

The helical or spiral anchoring segments 930 of the supplemental stabilizer 903 provide proximal support and stability of the aneurysm device 900 after implantation. The anchoring segments 930 can be wound in one direction or in opposing directions to form a matrix of overlapping helixes. The helical anchoring segments 930 can be made from implantable alloys, stainless steel, shape memory or shape changing materials (e.g., Nitinol and/or polymers), or other suitable materials. Additionally, radiopaque elements can be attached to or integrated with the anchoring segments 930.

Figure 10:
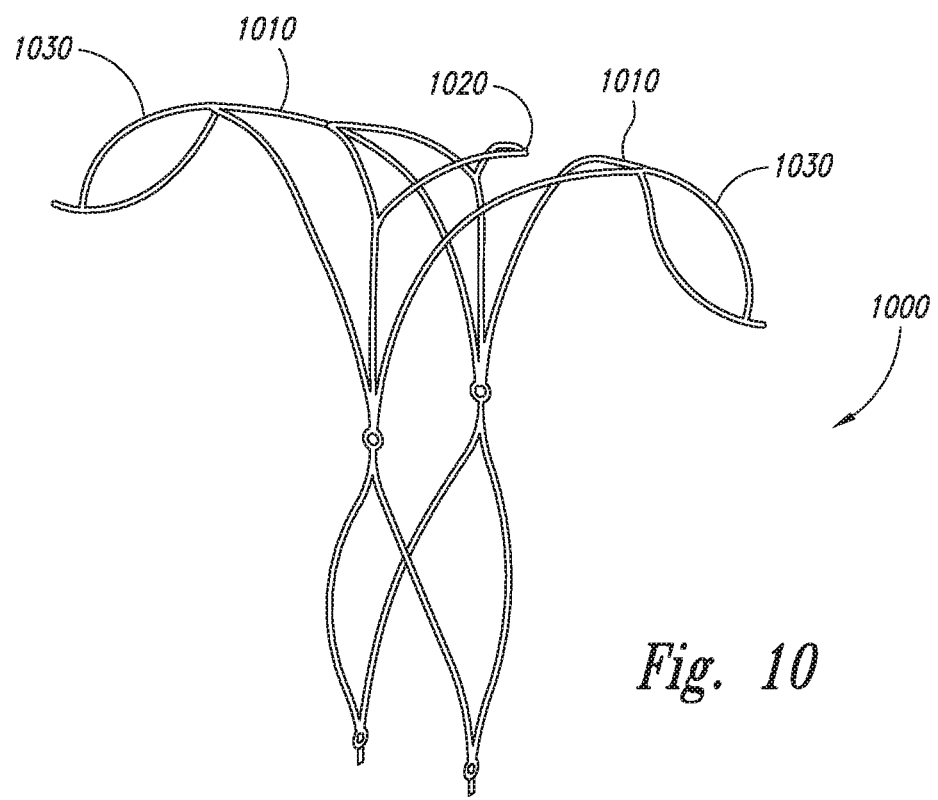
FIG. 10 is a view of an aneurysm device configured in accordance with another embodiment of the technology.
Figure 11:
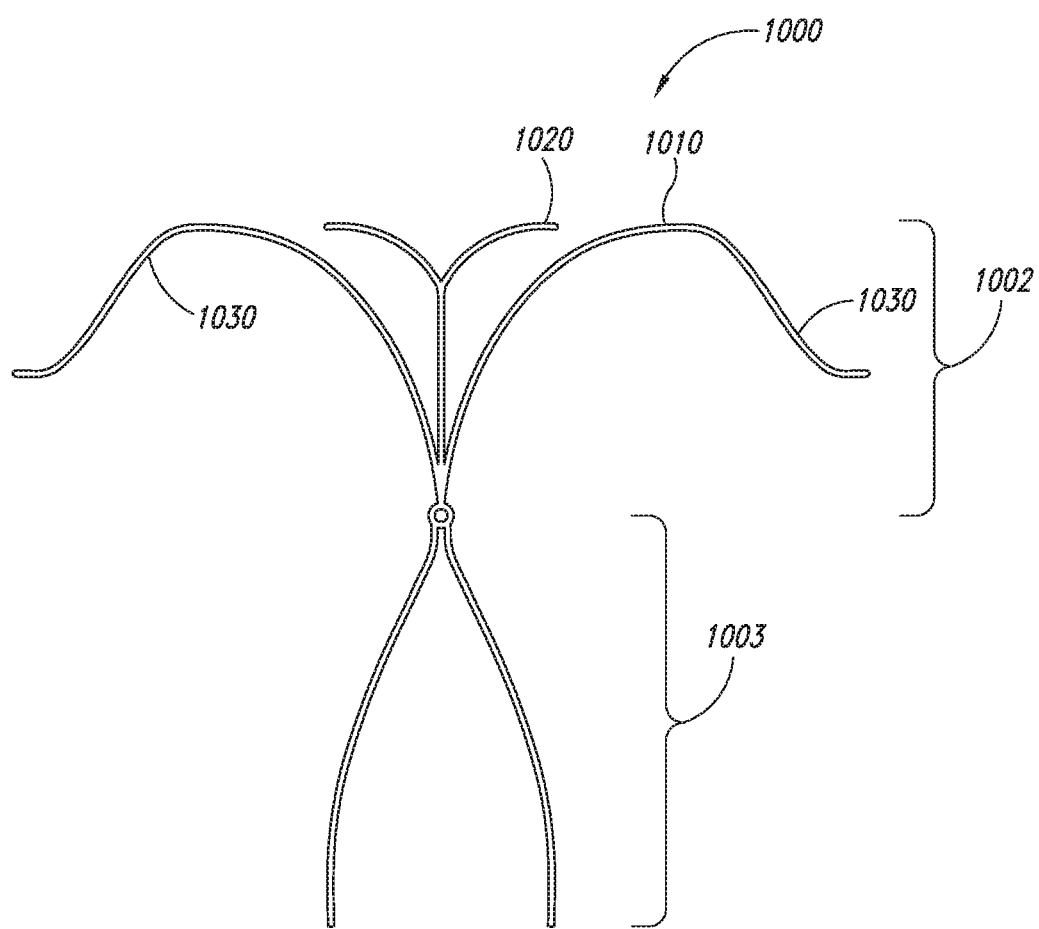
FIG. 11 is a side view of the device of FIG. 9.

FIG. 10 is an isometric view and FIG. 11 is a side view of an embodiment of another aneurysm device 1000 that includes a closure structure 1002 (FIG. 11) and a supplemental stabilizer 1003 (FIG. 11). Several embodiments of aneurysm devices can include variations in which the distal framework portion includes side branch artery encircling rings on the tips of the lateral apices. For example, the closure structure 1002 of the aneurysm device 1000 can have a perimeter support 1010, an inner support 1020, and distal anchoring segments 1030. The distal anchoring segments 1030 can be loops or arcuate segments that are configured to engage the inner wall of the side branch vessels. In the embodiment shown in FIGS. 10 and 11, the distal anchoring segments 1030 are loops extending from the lateral apices of the perimeter support 1010. However, the distal anchoring segments 1030 can project from the inner support 1020 in addition to or in lieu of the perimeter support 1010. The distal anchoring segments 1030 can be oval, circular, elliptical or other suitable shapes.

In operation, the distal anchoring segments 1030 can contact the vessel wall around a full circumference of the vessel or for a distance less than the full circumference that is sufficient to still fix the aneurysm device 1000 within the vessel. The distal anchoring segments 1030 accordingly stabilize the aneurysm device 1000 to inhibit migration after implantation. The anchoring segments can be made from shape memory/change material(s), metal alloys, stainless steel, or other suitable materials that provide an outward spring force against the vessel wall. In general, the distal anchoring segments 1030 are configured to be inserted in a low-profile state and then expand upon deployment to contact the vessel.

Figure 12B:
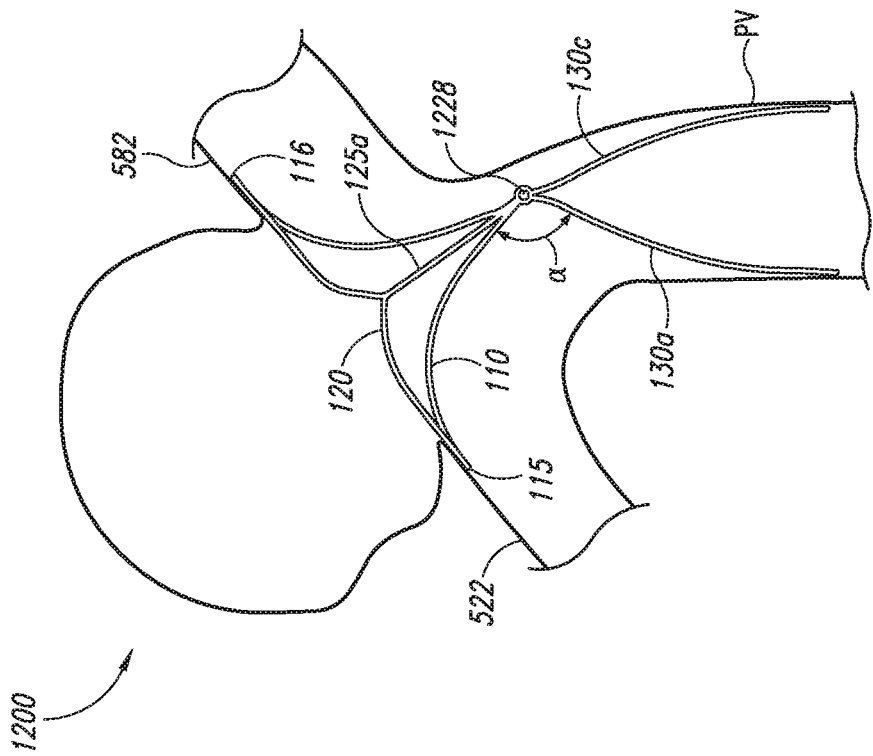
FIGS. 12A and 12B are views of an aneurysm device configured in accordance with another embodiment of the technology.
Figure 12A:
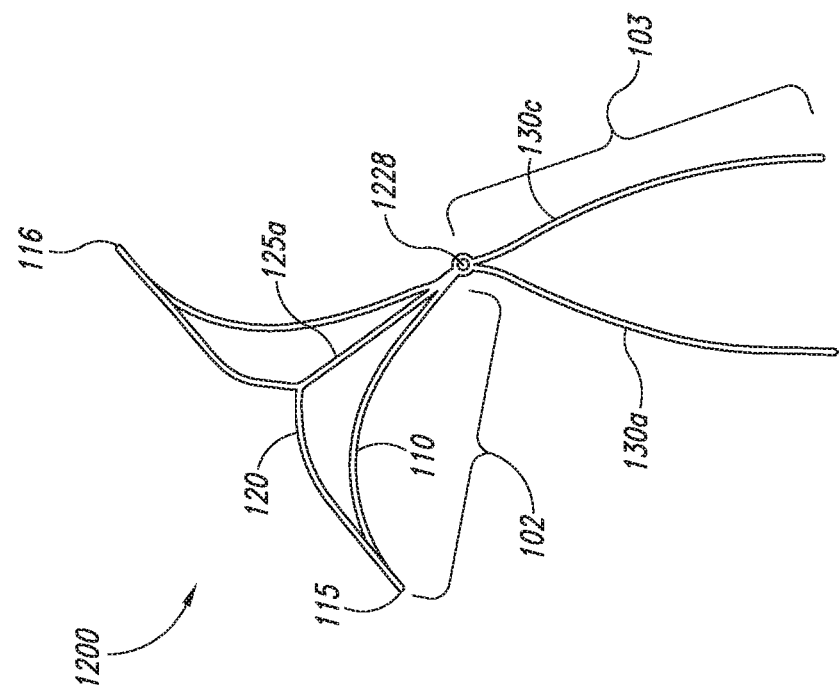

FIGS. 12A and 12B illustrate another embodiment of an aneurysm device 1200 having a closure structure 102 and a supplemental stabilizer 103 similar to those above described with respect to FIGS. 1A-1D. Like reference numbers accordingly refer to like components in FIGS. 1A-1B and 12A-12B. The aneurysm device 1200, however, has an articulating junction 1228 between the closure structure 102 and the supplemental stabilizer 103. Referring to FIG. 12B, the articulating junction 1228 can be manipulated to adjust the angle a between the closure structure 102 and the supplemental stabilizer 103 to accommodate situations in which the side branch vessels SB1 and SB2 are at substantially non-orthogonal angles relative to the longitudinal axis of the parent vessel PV.

Several of the foregoing embodiments of aneurysm devices configured in accordance with the technology accordingly have an expandable closure structure that, when expanded, is sized and configured to form a boundary or other semi-occlusion or full occlusion at the neck of an aneurysm at a bifurcation of a parent artery into side branch vessels (see, e.g., FIGS. 1B-1D, 2B-2E, 3A-3C, 4A-4C, 7A, and 7B). As described above, some embodiments of the aneurysm closure framework are formed from struts, typically from a resilient metal or a metal alloy such as Nitinol. In some embodiments, the metal struts are coated with an insulated covering comprising a polymer, parylene (poly p-xylylene), or a metal oxide.

The struts of the aneurysm devices typically comprise both the distal framework portion as well as the proximal framework portion, as described above. The distal portion of the device framework defining the closure structure and the proximal support framework defining the supplemental stabilizer are assembled together initially in a planar configuration in which the distal framework portion is between two oppositely disposed proximal framework portions. The three portions, as a connected whole, are aligned on a longitudinal axis (see, e.g., FIGS. 1A, 2A, 5A-5H, 6A, and 6B).

As described above, upon expansion into a deployed configuration from a radially compressed and constrained delivery configuration, the closure structure assumes a shape that defines a complex curved surface, such as a saddle-shape or a hyperbolic paraboloid form. A proximal surface of the closure structure faces into the parent artery and forms an arch that extends unobtrusively over the lumina of side branching arteries or vessels. The supplemental stabilizer (e.g., proximal support portion), upon expansion into a deployed configuration from a radially compressed and constrained delivery configuration, assumes or defines a shape that lies within the bounds of a cylindrical surface pressed against the lumen of the parent artery.

The outward bias of the device as a whole in its assembled form is related to a material shape memory of the native or neutral planar configuration. The folding and connecting aspects of assembly impart a constraint on both the proximal and distal portions of the device. The mechanical biases of the device work against such constraint and exert forces that hold the device in its stable assembled form and also stabilize the device when implanted at the target site. Stabilization at the site includes pressing and holding the distal face of the closure structure against the aneurysm neck and holding the supplemental stabilizer within the parent artery. By stabilizing the device proximally in the parent artery, lateral slippage in either of the side branching arteries or vessels is inhibited or prevented.

The length of the struts or extension elements and the dimensions of the internal rhombus-shaped supports are sized such that they collapse when being distally drawn into a delivery device in coordination with the collapse of external rhombi-like structures. Similarly, the expansion of appropriately sized internal rhombi-like structures and their extension elements is coordinated with the expansion of external rhombi-like structures upon ejection from a delivery device. The occurrence or rate of collapse and expansion of the internal rhombi-like structures is at least partly controlled by the length of the extension elements to which they are connected. For example, as the framework is being drawn into the radial confines of a delivery catheter, the internal rhombi do not begin to collapse until the full length of the extension element is drawn into the catheter. Further withdrawing into the delivery device draws the divergent struts together.

As noted above, some embodiments of the technology further include connector struts that stabilize the supports and contribute to the overall robustness of the device. The connector struts or internal framework lie at least partially within the margin of the aneurysm neck upon deployment. The internal framework structures are commonly mounted to at least one portion of the perimeter support of the distal framework. In one aspect, the internal framework structure(s) provide additional mechanical structure for retaining materials, such as debris and embolic materials, within the cavity of the aneurysm. In another aspect, the internal framework structures provide additional mechanical structure for supporting a barrier across the neck of the aneurysm. In another aspect, the internal framework structures provide additional mechanical structure and support for the closure structure that increases the structural integrity of the device without significantly increasing the weight, flexibility, or deployability of the device, and without impeding flow in the neighboring vessels.

In general, when the closure structure is properly positioned near the target aneurysm, the two opposing lateral apices of the closure structure are sized to approximately align with the lateral boundaries of the aneurysm neck. However, in some embodiments, a lateral apex of the closure structure extends substantially beyond a periphery of the aneurysm neck. In some embodiments of the technology the distal-facing aspect of the closure structure is laterally symmetrical in length; in other embodiments it may be laterally asymmetrical in length. Variations in the total length of the distal axis of the device and in the relative lengths of the two lateral halves of the device are structural features of the device that are designed to fit particular features of the target site. In typical embodiments of the distal framework, the diameter of the proximal-facing arch of the distal framework is sized to approximate the diameter of the side branch arteries over which it arches.

In several embodiments of the aneurysm device, two distal junctions that join the distal and proximal portions of the framework struts together are substantially opposite each other. Similarly, two proximal junctions that join the proximal ends of struts of the proximal support framework are substantially opposite each other. Further, the distal junction pair and the proximal junction pair are circumferentially distributed around the central longitudinal axis of the proximal support framework such that the four junctions (two distal, two proximal) are spaced apart by about 90 degrees. For example, in an end view, if a first distal junction is situated at 0 degrees, a first proximal junction would-be situated at about 90 degrees, a second distal junction would be situated at about 180 degrees, and a second proximal junction would be situated at about 270 degrees. As such, with regard to the first and second pairs of struts of the proximal support framework, the distal ends of each strut of each pair are joined together at one of the two distal junctions of the distal struts, and the proximal end of each strut of each pair is joined together with a proximal end of a strut of the second pair to form two proximal junctions, 180 degrees opposite each other. In typical embodiments of the proximal support framework, the first and second pairs of struts extend proximally from the first and second distal junctions to the first and second proximal junctions without intersecting each other. As described elsewhere, in some embodiments, each of the proximal junctions may serve as a detachable joint that connects the framework to a delivery wire.

When the device is implanted at a target site, the distal junctions and the proximal junctions all reside within the parent artery. The struts and junctions are all constructed and finished so as to be atraumatic to the luminal surfaces that they contact. Further, by the general closeness of their contact with the luminal surfaces and by their small diameter relative to the diameter of the vessels, the struts and junctions form no substantial intrusion into the parent artery and do not interfere with blood flow.

In typical embodiments of the framework, the distal junctions (joining the distal and proximal portions of the framework) and proximal junctions (joining proximal ends of the struts of the proximal support framework) are all biased outward to contact the walls of the parent artery with pressure sufficient to secure the framework therein. The struts of the proximal support framework are generally biased to push outward against the lumen of the parent artery and, accordingly, are in contact with the lumen substantially along their entire length. The distal and proximal junctions represent foci of the outward bias. As described above, the outward biasing force originates from the lateral vertex of the distal framework portion, which is folded against its native planar configuration. The outward biasing force is sufficient to stabilize the proximal support framework within the parent artery; with the proximal support framework stabilized, the distal framework(connected to the proximal support framework) is secured against slippage in either lateral direction within the side branching arteries. In general, the outward biasing force of the proximal support framework against the lumen of the parent artery is substantially less than that would be typically provided by a stent being used to maintain the integrity of a vessel. The lesser level of force is appropriate for the inventive device because the proximal support framework is not required to secure the device against longitudinal slippage (proximal or distal) within the parent artery, but is required only to maintain a longitudinal alignment. The direction of arterial flow generally biases slippage in a downstream (distal) direction, but such movement is prevented by the distal terminating anatomy of the parent artery as it bifurcates into side branching arteries.

In some embodiments of the technology the distal-facing aspect of the distal struts has a concave skeletal form; in other embodiment it may have a convex skeletal form. In some embodiments of the technology the distal-facing aspect of the struts is laterally symmetrical with respect to concavity or convexity; in other embodiments if may be laterally asymmetrical with respect to concavity or convexity.

Some embodiments of the technology include polymeric components or elements that are associated with the struts that form the distal-facing aspect of the aneurysm closure device. These embodiments incorporate polymeric material of any suitable type (as listed above), but parylene is a suitable example. In these embodiments of the device, polymer is applied to the assembled device, with lines of polymer extending across, and effectively connecting, one or more struts. The structural and functional advantages provided by these polymeric structural elements include the provision of a higher structural surface area arrayed across the distal-facing aspect of the device, with a minimal impact on collapsibility or compressibility of the device as a whole, as is required for accommodation in a delivery catheter.

FIG. 13A is a side view and FIG. 13B is a top plan view of anon-planar sheet 1300 of material from which the framework of the closure structure and supplemental stabilizer of any of the foregoing embodiments of aneurysm devices can be made. The sheet 1300 can have a first section 1302 having a first thickness $t_1$ and at least one second section 1304 having a second thickness $t_2$ different than the first thickness $t_1$. The first and second sections 1302 and 1304 can correspond to different portions of the framework, and the different thicknesses of the first section 1302 and the second section 1304 can be selected to vary the bending radius, strength, and/or biasing force of the different portions of the aneurysm devices. In the particular embodiment illustrated in FIGS. 13A and 13B, the first section 1302 is central, and the sheet 1300 has two second sections 1304 on either side of the first section 1302. Referring to FIG. 13B, the first section 1302 can provide the material for a closure structure 1310 of a device, and the second sections 1304 can correspond to separate, unassembled portions 1312a and 1312b of the supplemental stabilizer. The sheet 1300 further includes transition zones 1306 between the first section 1302 and second sections 1304. The transition zones 1306 typically provide a step or taper between the first section 1302 and the second sections 1304.

The non-planar sheet 1300 illustrated in FIGS. 13A and 13B enables the aneurysm devices to have different flex and strength properties at different areas of the device. In the embodiment illustrated in FIGS. 13A and 13B, the thinner first section 1302 provides enhanced flexibility to the curved portion of the closure structure, and the thicker second sections 1304 enhance the strength of the supplemental stabilizer. The sheet 1300 can have many different configurations with additional sections having thicknesses either thinner or thicker than the thicknesses $t_1$ and $t_2$. Additionally, the center first section 1302 can be thicker than the second sections 1304 in other embodiments that require more robust closure structures. For example, it may be desirable to have robust closure structures to increase the outward biasing force of the anchoring mechanism of a closure structure and/or the supplemental stabilizer.

D. Selected Embodiments of Aneurysm Devices with Barriers or Covers

In additional embodiments shown in FIGS. 14A-17, one or more barriers can be attached to selected struts of any of the foregoing closure structures described above. For example, a barrier can be attached to at least a portion of any of the perimeter and/or inner distal-facing supports having rhombus-like shapes described above. The barrier can be a permeable or semi-permeable membrane, cover, sheet, panel, or other structure that forms an occlusive or semi-occlusive covering that (a) restricts or inhibits vascular flow into the cavity of the aneurysm and/or (b) prevents materials from escaping the cavity. In this aspect, devices and methods of the described technology may provide repair and reconstruction of a blood vessel or a junction of blood vessels by placement and retention of a closure structure across the neck of the aneurysm that diverts blood flow away from the aneurysm. Following placement and deployment, the closure structure may substantially cover the aneurysm neck and form a structure that substantially conforms to the tissue surrounding the aneurysm and/or the neighboring vessel walls. The highly conforming fit generally restores the vascular anatomical neighborhood to a normal or more normal configuration, thereby supporting a normal vascular flow pattern and overall function. No part of the device (including the distal framework, the proximal support framework, or the membrane arranged across the distal framework) provides any substantial interference with normal or original patterns of fluid flow in the arterial lumens in proximity to the opening.

Figures 14A, 14B:
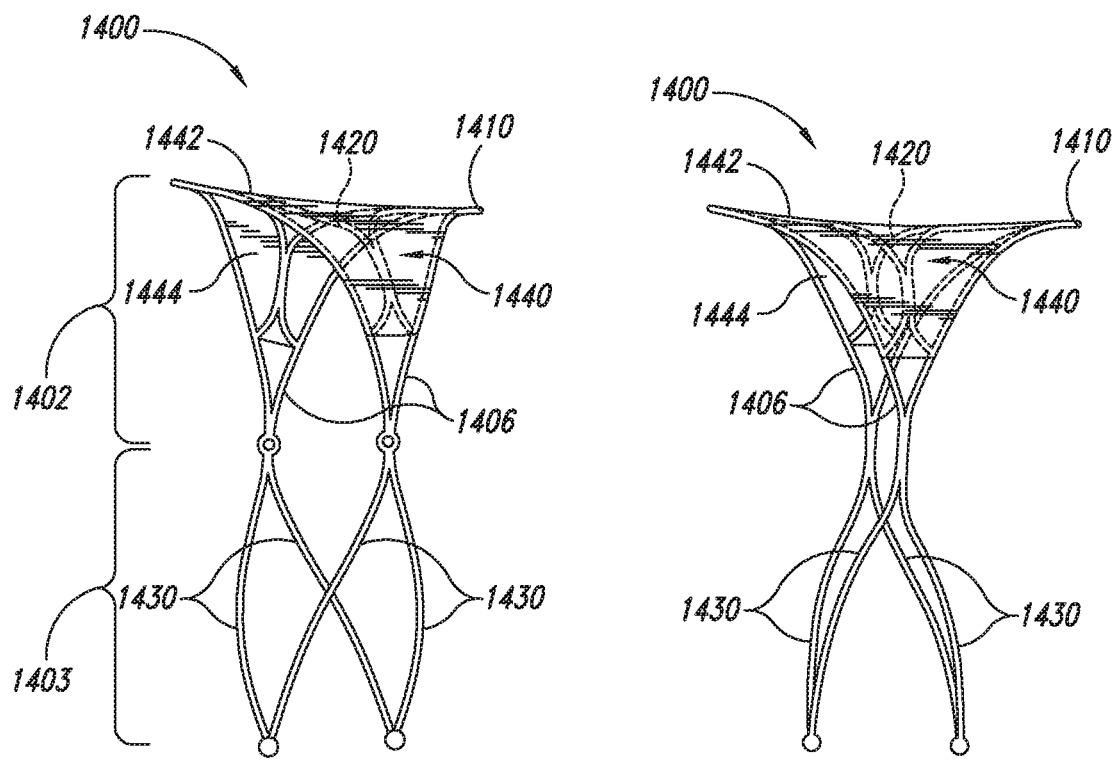
FIGS. 14A-14C are views of aneurysm devices configured in accordance with additional embodiments of the technology.

FIGS. 14A and 14B are isometric views of an embodiment of an aneurysm device 1400 having a barrier in accordance with the technology. In this embodiment, the aneurysm device 1400 has a closure structure 1402 and a supplemental stabilizer 1403 similar to the aneurysm devices described above. The closure structure 1402 can accordingly have a distal framework portion including a plurality of struts that form a perimeter support 1410 and an inner support 1420. The supplemental stabilizer 1403 can accordingly include a plurality of struts 1430 that form a proximal framework portion. The aneurysm device 1400 further includes a barrier 1440 that covers at least a portion of the closure structure 1402. In the particular embodiment illustrated in FIGS. 14A and 14B, the barrier 1440 can be a membrane or other type of cover that extends across the full lateral aspect of the perimeter support 1410. The embodiment of the barrier 1440 illustrated in FIGS. 14A and 14B accordingly covers a significant portion of the U-shaped curved region of both the perimeter support 1410 and the inner support 1420.

The barrier 1440 can have a distal surface 1442 configured to contact the inner wall of the side branch vessels and substantially seal the neck of an aneurysm. The barrier 1440 further includes a proximally facing surface 1444 configured to unobtrusively guide or direct the blood flow from the parent vessel through the side branch vessels. The barrier 1440 accordingly enhances the separation between the cavity of an aneurysm and the lumen of the side branch vessels compared to aneurysm devices without the barrier. As explained in more detail below, the barrier is a thin, flexible material that can be readily folded to be placed in a delivery catheter and then expanded upon deployment. The barrier 1440 can accordingly be made from an elastic or inelastic material depending upon the application.

Figure 14C:
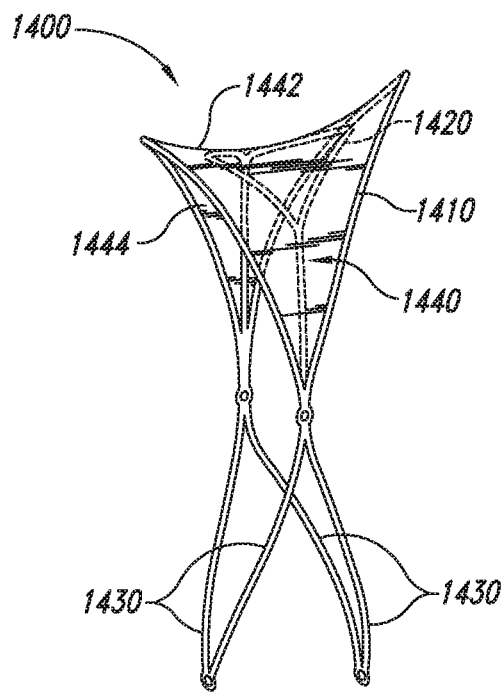

FIG. 14C is an isometric view illustrating an alternate embodiment of the aneurysm device 1400 in which the curved portion of the closure structure has a hyperbolic paraboloid profile and the barrier 1440 covers substantially all of the framework of the closure structure. The barrier 1440 accordingly has a saddle shape to conform to the particular anatomy. Accordingly, the perimeter support 1410, inner support 1420, and/or the barrier 1440 may have complex curve configurations.

Figure 15A:
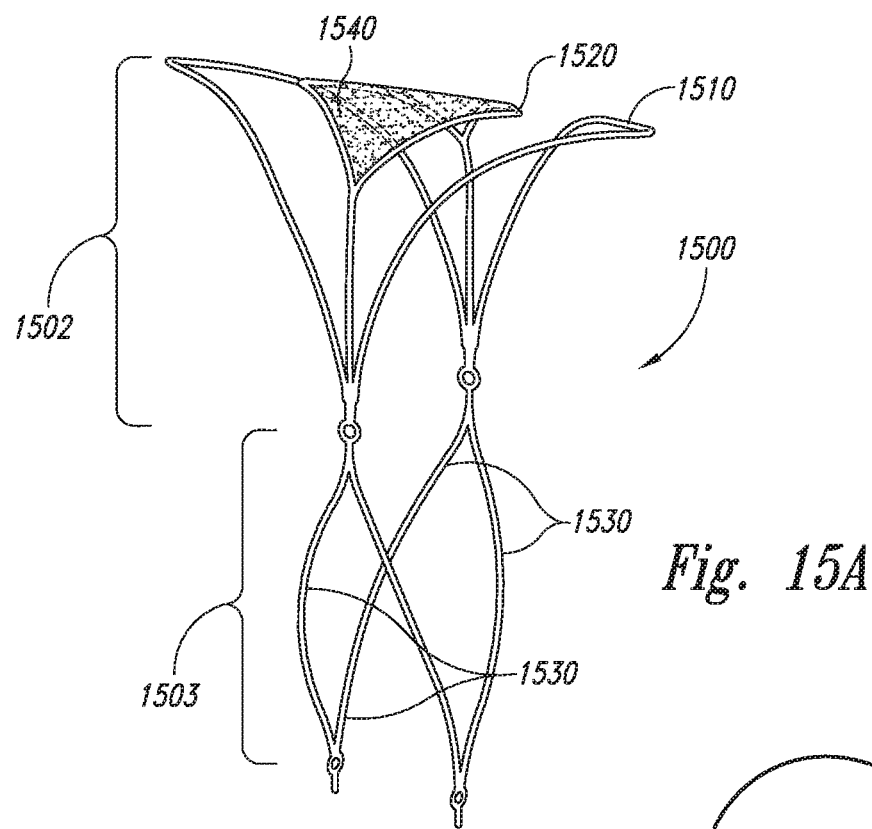
FIGS. 15A-15C are views of aneurysm devices configured in accordance with additional embodiments of the technology.
Figure 15B:
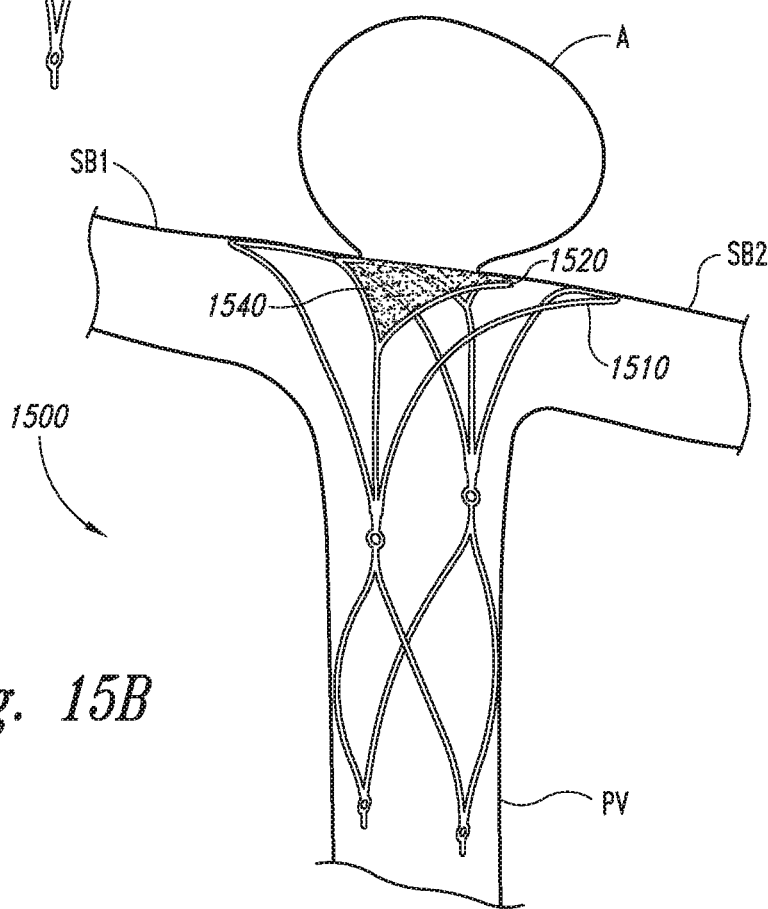
Figure 15C:
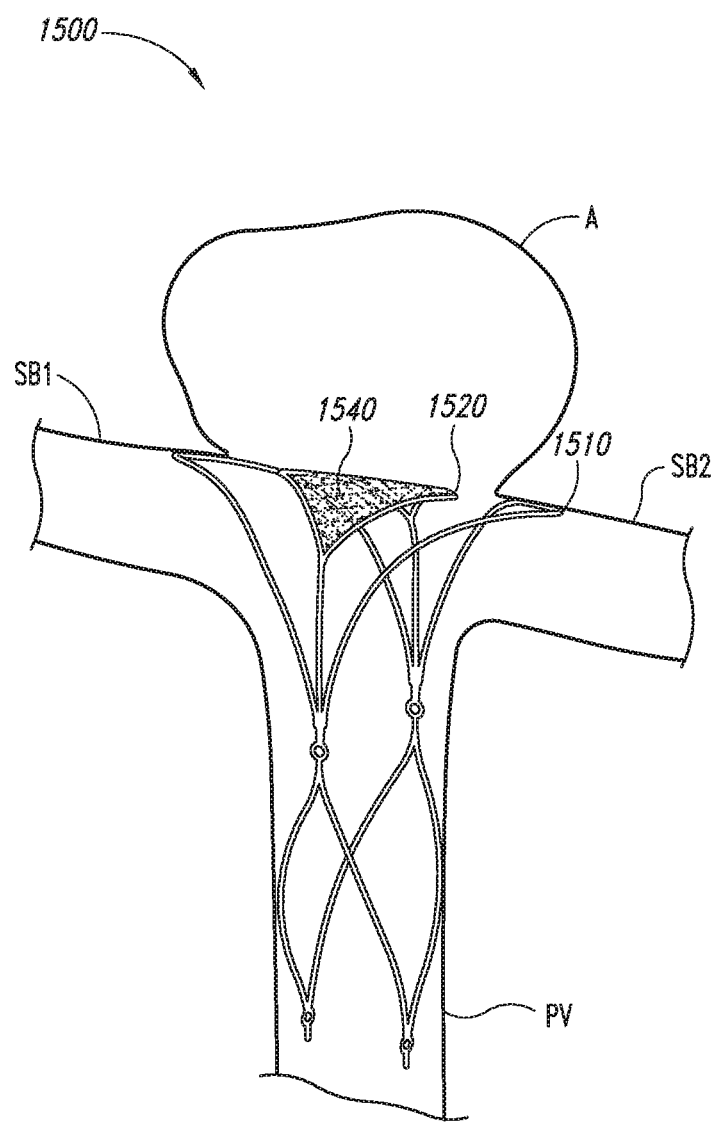

FIGS. 15A-15C illustrate an aneurysm device 1500 having a barrier configured in accordance with another embodiment of the technology. The aneurysm device 1500 can include a support structure 1502 having perimeter and inner supports 1510 and 1520, respectively, and a supplemental stabilizer 1503 having struts 1530. In this embodiment, the aneurysm device 1500 includes a barrier or membrane 1540 attached to the inner support 1520, but not to the perimeter support 1510. As such, instead of having a barrier coextensive with the distal boundaries of the closure structure as in FIGS. 14A-14C, the barrier 1540 is not coextensive with the perimeter support 1510.

FIGS. 15B and 15C illustrate different implementations of the aneurysm device 1500. As illustrated in FIG. 15B, the inner support 1520 and the barrier 1540 substantially cover the neck of an aneurysm A, and the perimeter support 1510 contacts the neck of the aneurysm A and/or the vessel walls of the side branch vessels SB1 and SB2 proximate to the aneurysm neck. In this embodiment, the lateral portions of the perimeter support 1510 contact the vessel wall at locations more distant than the neck of the aneurysm to provide support at the vessel wall surface areas that are generally healthy and resilient. With respect to FIG. 15C, the inner support 1520 and barrier 1540 partially occlude, but do not completely cover, the neck of the aneurysm A. This deployment strategy provides a flow diversion from the central portion of the parent vessel PV and a central portion of the neck of the aneurysm A without completely occluding the neck of the aneurysm A.

Figure 16A:
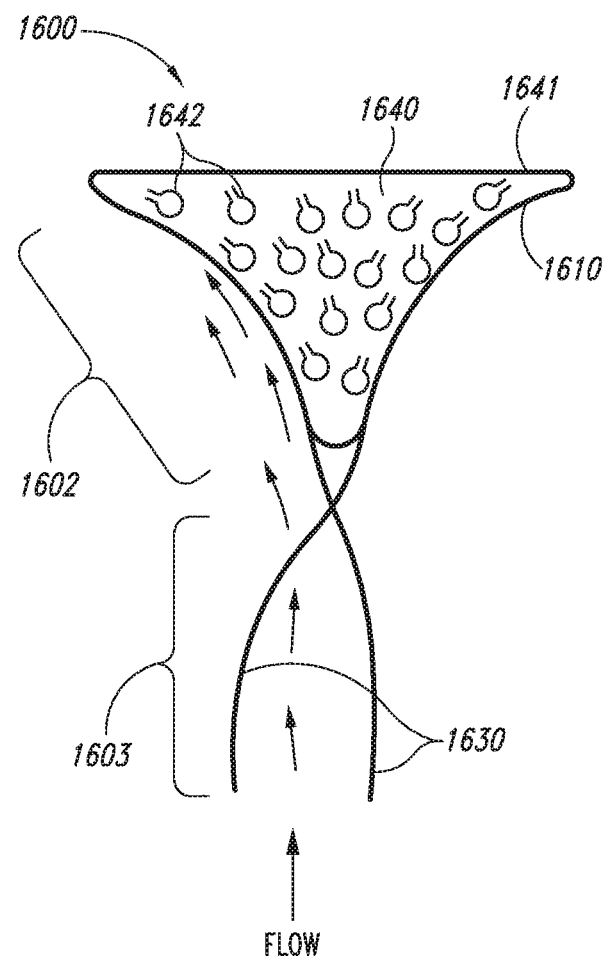
FIGS. 16A-16C are views of an aneurysm device having a barrier configured in accordance with an additional embodiment of the technology.

FIG. 16A is a side view of an aneurysm device 1600 configured in accordance with another embodiment of the technology. In this embodiment, the aneurysm device 1600 includes a closure structure 1602 having a perimeter support 1610 and a supplemental stabilizer or support 1603 having a plurality of struts 1630. The closure structure 1602 is not limited to having only the perimeter support 1610; rather, the closure structure 1602 can be any of the foregoing embodiments of closure structures. Similarly, the supplemental stabilizer 1603 can be any of the foregoing embodiments of supplemental stabilizers. The aneurysm device 1600 further includes a barrier 1640 having a sheet 1641 and at least one one-way valve 1642 through the sheet 1641. In the embodiment illustrated in FIG. 16A, the barrier 1640 has a plurality of one-way valves 1642.

Figure 16B:
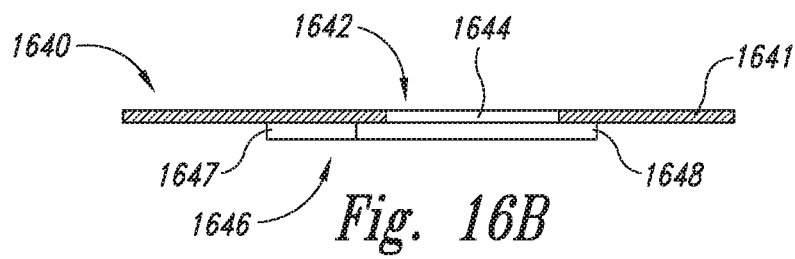
Figure 16C:
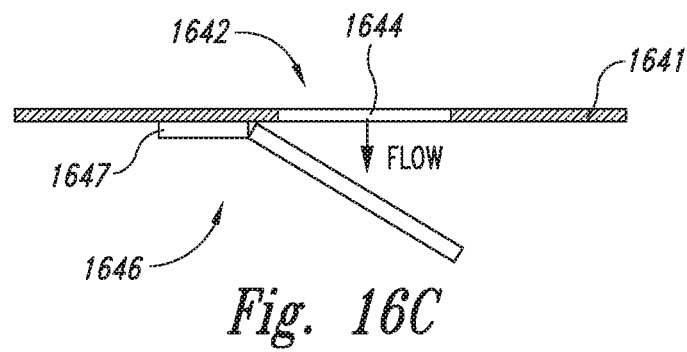

FIGS. 16B and 16C illustrate an embodiment of the one-way valve 1642 that can be used for the barrier 1640. In this embodiment, the sheet 1641 has an opening 1644, and the one-way valve 1642 includes a flap 1646 having a fixed base portion 1647 and a cover 1648. The base portion 1647 can be attached to or otherwise integral with the sheet 1641, and the cover 1648 can move between a closed position (FIG. 16B) and an open position (FIG. 16C). The cover 1648 is generally larger than the opening 1644. Therefore, the one-way valve 1642 closes to prevent flow across the barrier 1640 when the pressure on the side with the flaps 1646 is greater than the pressure on the other side of the sheet 1641. Conversely, the one-way valve 1642 opens to allow flow through the opening 1644 when the pressure on the side of the sheet 1641 opposite the flap 1646 is higher. The barrier 1640 can accordingly selectively allow flow into or out of an aneurysm A for controlling the pressure within the aneurysm.

As described above, the framework may include struts that form quadrilateral forms arranged in an internal to external hierarchy on the distal face of the distal portion of the framework. As described above, two portions of the framework opposite each other across the central longitudinal axis of the framework may be referred to as lateral leaves of the framework; this term is particularly applicable to the framework when a membrane or barrier covers at least a portion of it. In some embodiments, the membrane covers the distal face of the device entirely, filling the distal-facing aspect completely within the bounds of the most external or peripheral quadrilateral form. In other embodiments, where the distal-facing aspect of the distal framework can be sectored into internal and external quadrilateral (or other polygonal) forms, the membrane may only partially cover the distal face. For example, a membrane may cover an internal quadrilateral form and leave a zone between the internal quadrilateral and the external quadrilateral open. Similarly, a membrane may be arranged on a peripheral sector, between the boundary of an internal quadrilateral form and the peripheral quadrilateral boundary. Other arrangements may be formed, depending on the complexity of the distal-facing aspect of the distal framework.

Coverings and membranes including both occlusive and semi-occlusive materials may be provided and supported by the framework structure. Occlusive and semi-occlusive coverings and membranes may incorporate pores or perforations and may have a variety of surface treatments. Coverings may also incorporate or be associated with a variety of materials to provide properties desired for various applications. The distal framework portion of the device is generally sized and configured to reside entirely outside the neck of the aneurysm following deployment. In some alternative embodiments, the distal framework portion of the device may be associated with a structure extending distally for placement inside the cavity of the aneurysm, such as described in U.S. patent application Ser. No. 12/554,850 (now U.S. Pat. No. 8,388,650) by Gerberding et al., entitled "Systems and Methods for Supporting or Occluding a Physiological Opening or Cavity", which is incorporated herein by reference in its entirety.

The membrane may have a porous or perforated surface structure over at least a portion of its surface area, with pores arranged to provide a substantially uniform porosity over the surface area, or with pores arranged to provide different porosities at different surface areas of the closure structure. The average pore size may be substantially uniform over the surface area of the closure structure, or pore size may be distributed over a range of sizes. In general, pore sizes in the range of from about 0.5 microns to 400 microns are suitable. In one embodiment, a pore structure is provided that permits flow of liquids across the closure structure but excludes large proteins and cells circulating in the blood. In general, pores having an average diameter of less than about 10 microns will exclude large proteins and cells, while allowing fluids to transfer across the membrane. The arrangement of pores may forma regular or irregular pattern, and the conformation of the pores may be uniform or non-uniform and of any shape. A higher porosity may be provided, for example, at peripheral portions of the closure structure that, following placement, are in proximity to or contact the tissue or vessel wall.

The membrane may also incorporate holes, cutout portions, or other peripheral features that are designed to allow greater pliability or compliance of the membrane with regard to folding, compressing, or compacting, and the reversal of these processes (unfolding, decompressing, expanding), particularly in such a way that maintains integrity of the membrane. In some embodiments, holes or cutout profiles are distributed along the periphery of the membrane. In some embodiments of the membrane, cutout profiles, or open areas are located at the lateral and/or longitudinal apices of the cover. In some embodiments, the open areas are supported by structural elements that are disposed within the perimeter of the main structural struts of the distal framework portion.

These different covering arrangements may be appropriate for different clinical or therapeutic situations. For example, in an emergent situation in which an aneurysm has recently hemorrhaged, it may be clinically appropriate to implant a device with a covering that extends only across the peripheral zone of the distal face of the device. Further, in an emergent situation, it may be clinically appropriate to not detach the device, but rather to leave it connected to its delivery wire so that it can be withdrawn or repositioned.

In some embodiments of the technology, a framework with a membrane covering at least part of a distal-facing aspect of the distal framework portion functions as a vascular flow diverter, preventing or impeding blood flow into an aneurysm cavity. Blood has a tendency to clot when its flow is slowed only a little; it is not necessary that it be stopped entirely or even substantially for its condition to become liable to clotting. Thus, even a minimal diversion of blood away from the aneurysm may be clinically effective in inducing a coagulative condition in the aneurysm cavity that is therapeutically beneficial. An important structural element in diverting blood flow away from the aneurysm may be a proximally directed wedge formed by the membrane along the axis that separates the two lateral leaves of the distal framework. From the perspective of a view looking proximally from the distal face of the framework, the wedge manifests as a cleft within the cover between the two lateral leaves of the distal framework. When implanted, the leading edge of the wedge is oriented orthogonally with respect to the common axis of the two arteries bifurcating from the parent artery.

Figure 17:
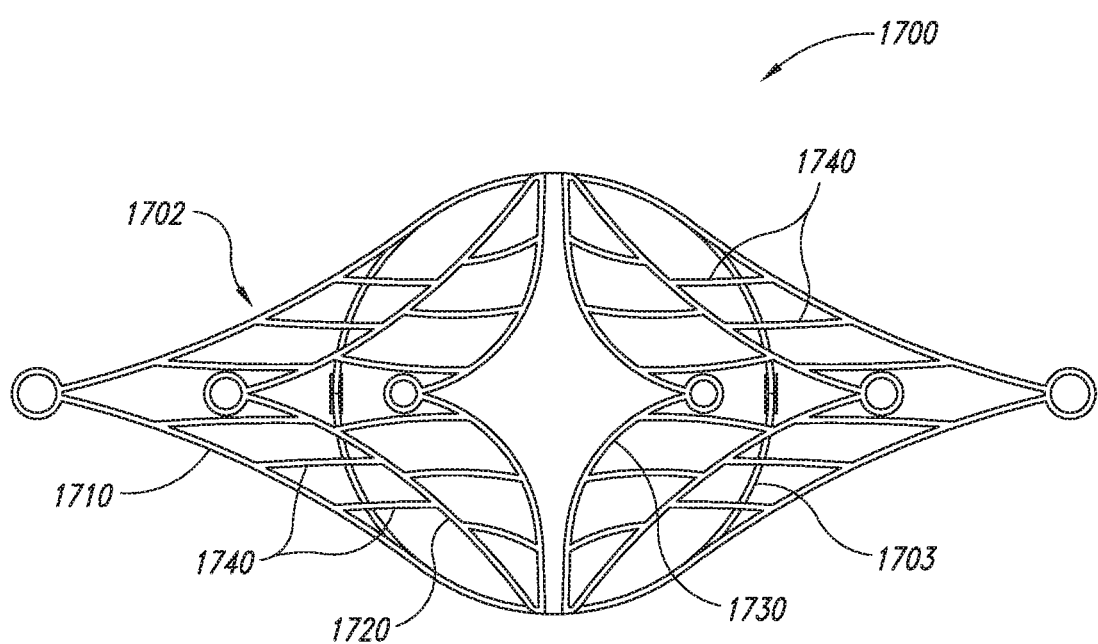
FIG. 17 is a view of an aneurysm device having a barrier configured in accordance with an additional embodiment of the technology.

FIG. 17 is a top view of an aneurysm device 1700 configured in accordance with the technology. The aneurysm device 1700 is a composite design that includes a closure structure 1702 and a supplemental stabilizer 1703 defined by a distal framework portion and a proximal framework portion, respectively, similar to the frameworks of the aneurysm devices described above. In this specific example, the closure structure 1702 of the aneurysm device 1700 includes a perimeter support 1710, an intermediate support 1720, and an inner support 1730 formed by a plurality of struts. The supports 1710, 1720, and 1730 can have rhombus-like shapes in which the sides have varying degrees of curvature. The aneurysm device 1700 further includes a barrier 1740 comprised of a plurality of flexible strands, straps, or bands that are individually attached to the supports. For example, a first set of straps can extend between the perimeter support 1710 and the intermediate support 1720, and a second set of straps can extend between the intermediate support 1720 and the inner support 1730. In other embodiments, a single strap can extend across all or between any of the supports of the closure structure 1702. The individual strands or straps can be made from a highly flexible, thin polymeric material. The strands, for example, can be elastic or inelastic such that they unfold upon deployment as the closure structure 1702 expands.

The strands or straps of the barrier 1740 can be attached to the support 1710, 1720, and/or 1730 of the closure structure 1702 after bending the distal framework portion to form the curved closure structure 1702. This process is useful in embodiments in which the strands are formed from a material that would deform or otherwise burn off at the temperatures of the bending process.

The strand-type barrier 1740 illustrated in FIG. 17 is generally a substitute for a contiguous-type barrier, such as the barriers 1440 and 1540 described above with reference to FIGS. 14A-15C. The strand-type barrier 1740 of the aneurysm device 1700 is expected to achieve a higher density of scaffolding for coil support without adding additional metal because the strands are more flexible and thinner than struts or contiguous barriers. The strand-type barrier 1740 is also expected to occupy less volume when collapsed into a configuration for insertion into a delivery catheter compared to the contiguous-type barriers because the strand-type barrier uses less material. The strand-type barrier accordingly allows for a lower profile and more flexible design compared to other configurations.

E. Materials for the Framework and the Barrier

The framework portion of the inventive device may be constructed from a variety of resilient metallic materials, polymeric materials (e.g., polyethylenes, polypropylenes, Nylons, polytetrafluoroethylenes(PTFEs), and the like), and composites of materials. Further appropriate or typical materials include biocompatible stainless steels, highly elastic metallic alloys, and biocompatible shape change materials that exhibit pseudo-elastic or super-elastic behavior and/or shape memory properties, such as shape memory alloys. Structures made from shape change materials have a preferred or native configuration and are also highly elastic; they can be deformed or constrained into a secondary configuration, but upon release from the constraint, they return toward their native configuration with high fidelity.

Nitinol alloys exhibiting super-elastic behavior are preferred form any implantable devices described herein and may be used to construct both the framework elements, generally referred to as struts, and as described in further detail below. In some embodiments, Nitinol alloys may also be used to construct a closure membrane. When metallic materials such as Nitinol are used, framework structures may be formed, for example, from solid wire, tubular wire, braided materials, or the like, and/or may be cut (or etched or otherwise removed) from substantially flat sheets of material or from shaped substrate materials. Framework and anchoring structures may incorporate additional materials and may have coatings or membranes provided between and among the framework struts. In one embodiment, the framework struts may be formed from a thin-film highly elastic alloy, such as a thin-film Nitinol alloy, using sputtering techniques that are known in the art. In another embodiment, the framework struts may be constructed from a metallic or polymeric or composite material by cutting, or etching, or otherwise providing a preassembled shape from a substantially flat sheet substrate and subsequently shaping the preassembled shape to provide the desired deployed conformation.

The occlusive or semi-occlusive membrane or cover is generally constructed from material(s) that are biocompatible, biostable, and compressible, foldable, deformable, or compliant to allow compression or compacting into a low diametric profile in a delivery condition for loading into or mounting to a delivery catheter. Suitable membranes may comprise at least one layer of flexible material and may have a substantially continuous, non-porous structure. Alternatively, occlusive or semi-occlusive membranes may have various types of porous, perforated, woven, non-woven and fibrous structures and may comprise multiple layers of material.

In one embodiment, the closure membrane is constructed from a material that is substantially impermeable to liquids such as blood and bodily fluids. Alternatively, the closure membrane may be constructed from a material that is semi-permeable or permeable to liquids, such as bodily fluids, and allows at least limited fluid exchange across the membrane. A closure membrane may be constructed, for example, from many types of natural or synthetic polymeric materials, polyurethanes, silicone materials, polyurethane/silicone combinations, rubber materials, woven and non-woven fabrics such as Dacron™, fluoropolymer compositions such as a PTFE materials, expanded PTFE materials (ePTFE) such as and including TEFLON®, GORE-TEX®, SOFTFORM®, IMPRA®, and the like.

In another embodiment, the closure membrane may include a metallic material, such as a thin-film shape memory alloy, e.g., a thin-film nickel-yitanium alloy such as a Nitinol alloy or other biocompatible metals, including noble metals, in such forms as gold foils, tantalum wire and the like. The membrane may be bonded, mechanically attached, or fused to the frame to provide a secure seal and contribute to device strength. In some embodiments, the membrane and structural framework component may be constructed from a single piece of material such as Nitinol, stainless steel, silicone, Dacron, ePTFE, or another polymeric material.

In some embodiments, the closure membrane includes a mesh-like structure, typically a fine mesh, having a uniform or non-uniform configuration over its surface area. In some embodiments, the membrane has a mesh-like structure that is radially expandable or expandable along one or more axes. The closure membrane, in some embodiments, is semi-permeable and has radial flexibility sufficient to mimic the structure and accommodate movement of the targeted treatment site. When an implantable device with a membrane is placed across the neck of an aneurysm, for example, it may become substantially continuous with and follow the motion of the vessel wall, providing effective repair and reconstruction of the vessel wall and restoring strength, structure and flexibility to the vessel wall. In some embodiments, the inventive device, after placement across a tissue or vessel defect, may further promote cellular ingrowth and reendothelialization across its surface, thereby further incorporating the device in anatomical structure and reducing the opportunity for the anatomy to weaken and return to a defective condition.

The inventive device, including the membrane, may also incorporate a reinforcing structure throughout its surface area, or in particular areas of its structure. In one embodiment, for example, a resilient and flexible sheet material may be bonded to or associated with a more rigid reinforcing structure having a regular or irregular pattern.

The membrane may include a surface treatment provided on one or both sides that promotes cellular attachment and growth. In one embodiment, for example, the membrane material has a surface conformation that is irregular, or roughened, or incorporates surface irregularities that promote cellular attachment to the material. In another embodiment, the closure structure may have a three dimensional configuration with features such, for example, depressions, grooves, or channels, in a regular or irregular pattern, to promote cellular attachment and re-endothelialization.

In some devices disclosed herein, the membrane and the framework structures, and/or other structural components of the implantable device may be structured or treated or incorporate a material or a bioactive agent that promotes, cellular ingrowth or attachment at the site of deployment. Similarly, methods of the present technology may involvement of features or introduction of an agent that promote cellular ingrowth and re-endothelialization at the site of the device deployment prior to, during, and/or subsequently to placement of the implantable device. For vascular applications, for example, it is desirable for some applications to promote the re-endothelialization of the blood vessel at the site of an aneurysm or another vessel defect that may be repaired by placement of devices of the present technology. Numerous substances that may be used in connection with methods and systems of the present technology are described in U.S. Patent App. Publication Nos. US 2004/087998 and US 2004/0193206, which are incorporated herein by reference in their entireties.

Numerous materials may be administered prior to, during or subsequent to device deployment, or associated with the implantable device, to promote cellular ingrowth. Biocompatible materials may be used for this purpose including, for example, structural proteins such as collagen, fibrin, or fibronectin, or biologically active proteins, such as antibodies, cytokines, growth factors, enzymes, and the like; as well as polysaccharides such as heparin, chondroitin; biologically originated crosslinked gelatins; hyaluronic acid; poly(alpha.-hydroxy acids); RNA; DNA; other nucleic acids; polyesters and polyorthoesters such as polyglycolides, polylactides and polylactide-co-glycolides; polylactones including polycaprolactones; polydioxanones; polyamino acids such aspolylysine; poly-cyanoacrylates; poly(phosphazines); poly(phosphoesters); polyesteramides; polyacetals; polyketals; polycarbonates and polyorthocarbonates including trimethylene carbonates; degradable polyethylenes; polyalkylene oxalates; polyalkylene succinates; chitin; chitosan; oxidized cellulose; polyhydroxyalkanoates including polyhydroxybutyrates, poly-hydroxyvalerates and copolymers thereof; polymers and copolymers of polyethylene oxide; acrylic terminatepolyethylene oxide; polyamides; polyethylenes; polyacrylonitriles; poly-phosphazenes; polyanhydrides formed from dicarboxylic acid monomers including unsaturated polyanhydrides, poly(amide anhydrides), poly (amide-ester) anhydrides, aliphatic-aromatic homopolyanhydrides, aromatic polyanhydrides, poly(ester anhydrides), fatty acid based polyanhydrides, and the like; as well as other biocompatible or naturally occurring polymeric materials, copolymers and terpolymers thereof; fragments of biologically active materials; and mixtures thereof Some biocompatible polymers are considered to be bioabsorbable and are suitable for use in association with devices and methods of the present technology, including polylactides, polyglycolides, polylactide-co-glycolides, polyanhydrides, poly-p-dioxanones, trimethylene carbonates, polycaprolactones, polyhydroxyalkanoates, and the like. Biocompatible polymers which are not generally considered to be biodegradable may also be used, including polyacrylates; ethylene-vinyl acetates; cellulose and cellulose derivatives including cellulose acetatebutyrate and cellulose acetate propionate; acyl substituted cellulose acetates and derivatives thereof; non-erodible polyolefins; polystyrenes; polyvinyl chlorides; polyvinyl fluorides; polyvinyl (imidazoles); chlorosulphonated polyolefins; polyethylene oxides; polyethylene glycols; polyvinyl pyrrolidones; polyurethanes; polysiloxanes; copolymers and terpolymers thereof and mixtures thereof. Appropriate polymers are well known in the art and one of ordinary skill in the art would understand that such polymers are by far too numerous to list here. Thus, this list, as well as other lists of examples included herein, are intended for illustrative purposes only and are not intended to be exhaustive.

Biological agents such as hormones and growth factors may also be used on connection with membranes and implantable devices of the present technology. Examples of other biocompatible materials that promote integration with the vasculature of the patient include, for example, processed human or animal tissue including, for example, cells or portions thereof, engineered vascular tissue, biologically derived or synthetic matrix or basement membrane material.

Other types of compositions may also be associated with a membrane, framework structure and/or anchoring structure(s) forming the implantable devices of the present technology. Hydrophilic and/or hydrophobic agents or bonding agents may be provided on all or a portion of the structure(s), for example. Similarly, friction-reducing agents, including fluoropolymers such as PTFE, may be provided on all or a portion of the structure(s) to facilitate deployment from a delivery catheter or sheath. In yet another embodiment, certain therapeutic agents, antibiotic agents, thrombogenic agents, anti-thrombogenic agents, and the like may be associated with certain structures or portions of the device structure, or may be administered prior to, during or following deployment of the implantable device. Suitable agents are well known in the art and are used in connection with other types of implantable devices.

The membrane may comprise multiple layers, and may have a variety of coatings or other materials associated with it, such as adherent or bonding substances, therapeutic substances, hydrophilic or hydrophobic materials, swellable materials such as hydrogels, radiopaque markers, and the like. In one embodiment, for example, a swellable hydrogel may be provided on a surface of the closure structure and/or anchoring structures that, in a deployed condition, face or contact an internal portion of an aneurysm. In another embodiment, an agent or combination of agents that promote embolization or thrombosis may be provided on a surface of the membrane, framework support structure and/or anchoring structures that, in a deployed condition, face or contact an internal portion of an aneurysm to promote embolization inside the aneurysm. In yet another embodiment, an agent or combination of agents that reduce thrombosis and clotting, such as heparin, tissue plasminogen activator (tPA), Abciximab, and the like may be provided on a surface of the closure structure and/or anchoring structures that, in a deployed condition, face or contact a blood vessel or blood vessel wall. In still another embodiment, an agent or combination of agents that prevent restenosis and/or reduce inflammation to the site, such as Paclitaxel or a derivative or analog, Sirolimus, anti-inflammatory compositions such as steroids, statins, ibuprofen or the like, may be provided on a surface of the closure structure and/or anchoring structures. In yet another embodiment, a radioactive composition may be associated with a surface of the closure structure and/or anchoring structures for therapeutic or imaging purposes.

The membrane associated with the framework support structure placed across the neck of the aneurysm may have an opening or slot for passage of a guidewire of another delivery or targeting mechanism, or for introduction of compositions, devices, or the like subsequent to placement of the closure system. According to some methods of the present technology, additional embolic devices such as coils, liquid or particulate embolics, or any suitable embolic or coagulant material, maybe introduced through a delivery catheter inserted through an opening of the closure structure following placement of the closure structure.

The material(s) forming the membrane may be designed to incorporate various agents and/or coatings homogeneously or heterogeneously provided across one or all layers to promote or retard cell growth, depending on the characteristics desired. For example, the inside surface of the covering may be coated with an agent to prevent excessive cell growth that may block the lumen of the vessel (i.e., to prevent restenosis), while the outer surface of the covering may be coated with a material designed to promote a healing response. In other embodiments, specific portions or sections of individual coverings may be coated or provided with materials having different properties. Other physical features of the membrane are described further in a section below.

Radiopaque markers or radiopaque compounds may be associated with certain structures or portions of device structure to facilitate accurate positioning, placement and monitoring of the deployed device in the vasculature. In one embodiment, for example, a radiopaque composition maybe incorporated in the closure structure or provided as a coating on the closure structure. Variations in the marker geometry may be adopted to distinguish different segments of the device framework. For example, the proximal legs of the device may incorporate a marker with two dots, while the portion of the device closer to or in proximity to the covering may incorporate a single dot. Alternatively, different shaped markers may be used to differentiate different parts of the device. Radiopaque markers may be added anywhere along the device frame or attached materials, coverings, and membranes to provide spatial location of different device components and features under angiography.

F. Selected Embodiments of Delivery Devices

Endoluminal and endovascular procedures are commonly used for placing implantable devices and materials in many types of therapeutic interventions. An intravascular guide catheter is generally inserted into a patient's vasculature, such as through the femoral artery, and guided through the vasculature to the locale of a desired site of intervention. Additional delivery mechanisms and specialized catheters, such as microcatheters, pusher devices, and the like, may be used to facilitate delivery of various devices and accessories to the target site implantable devices are generally detachably mounted to a pusher or delivery mechanism and navigated through the guide catheter to the target site where they are deployed and detached from the delivery mechanism. The delivery mechanism is then withdrawn through the guide catheter and additional devices, accessories, drugs, or material may be delivered to the target site, if desired, prior to removal of the guide catheter.

In some embodiments of the technology, a delivery device is provided that retains the aneurysm device in a connected or held configuration and facilitates delivering, positioning, or deploying the aneurysm device. The delivery device may retain and hold an implantable aneurysm device at a distal end of a delivery mechanism, such as one or more delivery wires and an elongated, flexible introducer sheath provide dover the delivery wire(s) and sized and configured for passage through a guiding catheter or a delivery catheter. The implantable aneurysm device may be stored in a small diameter, delivery condition within a distal end of the sheath (e.g., a low-profile configuration). In alternative embodiments, the implantable aneurysm device may be assembled and stored in an expanded, deployed condition in a protective container. In general, the proximal end of the aneurysm device is attached to the delivery mechanism and the introducer sheath is positioned over the delivery mechanism. The aneurysm device can be rendered into a deliverable condition by retracting the aneurysm device into the distal end of the sheath before inserting the delivery device into a patient.

Figure 18A:
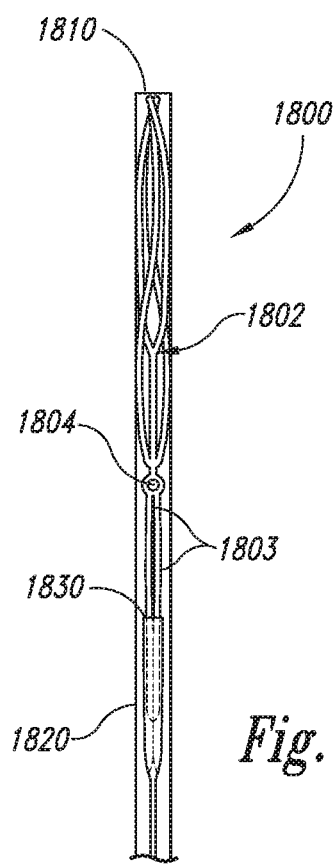
FIGS. 18A-18D are views of a delivery device and an aneurysm device configured in accordance with an embodiment of the technology.
Figure 18B:
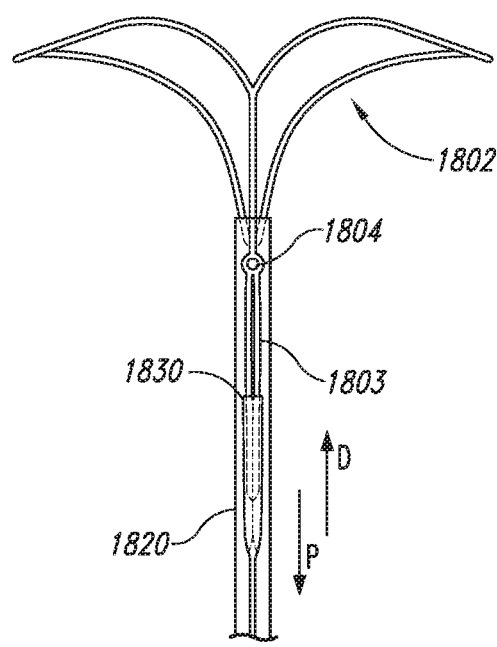
Figure 18C:
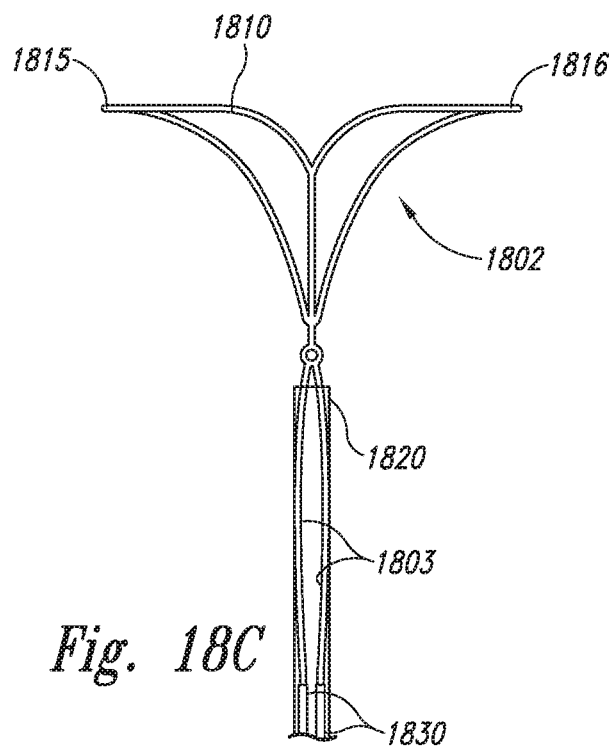
Figure 18D:
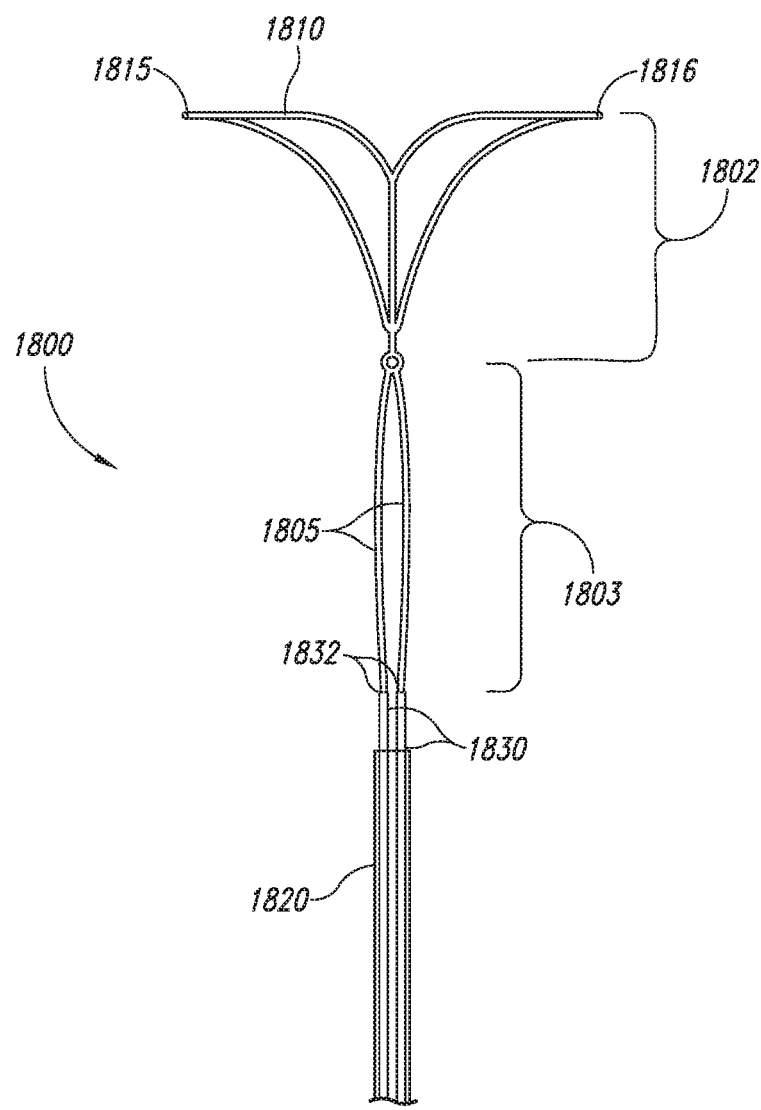

FIGS. 18A-18D illustrate an embodiment of an aneurysm device 1800 being deployed from a small diameter, folded delivery condition (FIG. 18A) to an expanded state in which the aneurysm device 1800 is nearly deployed (FIG. 18D). The aneurysm device 1800 can be any of the foregoing aneurysm devices described above. As such, the aneurysm device 1800 can include a closure structure 1802, a supplemental stabilizer 1803, and a junction or joint 1804 between the closure structure 1802 and the supplemental stabilizer 1803.

Referring to FIG. 18A, a delivery device can include an elongated, flexible introducer sheath 1820 and a positioning mechanism 1830, such as one or more delivery wires. The aneurysm device 1800 is generally radially compressed along its longitudinal axis and arranged in a substantially cylindrical, low-profile configuration within the sheath 1820. The proximal portion of the supplemental stabilizer 1803 is attached to a distal portion of the positioning mechanism 1830. The aneurysm device 1800 may be collapsed into the low-profile configuration shown in FIG. 18A using a loading sheath (not shown) into which the aneurysm device 1800 is loaded to assume a smaller diameter delivery condition before being transferred to the delivery sheath 1820.

The positioning mechanism 1830 can be a pusher system associated with the proximal or distal portions of the supplemental stabilizer 1803 and/or the closure structure 1802. The positioning mechanism 1830 can move within the delivery sheath 1820 to translate the aneurysm device relative to the delivery sheath 1820. The aneurysm device 1800 may be deployed by actively driving the positioning mechanism 1830 distally to push the aneurysm device 1800 out of the delivery sheath 1820 and/or by actively withdrawing the delivery sheath 1820 while maintaining the positioning mechanism 1830 and aneurysm device 1800 at a desired location. As described in more detail below, the aneurysm device 1800 and/or the positioning mechanism 1830 can incorporate detachment elements or detachment mechanisms 1832 for releasing the aneurysm device 1800. Detachment mechanisms known in the art, including mechanical, electrical, hydraulic, thermal, and/or other systems may be used.

In operation, the aneurysm device 1800 and delivery device can be passed through the vasculature using a guide catheter or other known techniques while the aneurysm device is in the low-profile configuration illustrated in FIG. 18A. When the aneurysm device 1800 is positioned within the vasculature at a treatment site, the positioning mechanism 1830 is moved distally and/or the delivery sheath 1820 is moved proximally until the aneurysm device 1800 is positioned beyond the distal end of the delivery sheath 1820 (FIGS. 18B-18D). As the aneurysm device 1800 exits the delivery sheath 1820, the closure structure 1802 expands into a deployed condition in which the lateral apices 1815 and 1816 of the support 1810 reach their fully extend lateral positions (FIGS. 18C and 18D). Referring to FIG. 18D, detachment mechanisms 1832 can detach struts 1805 of the supplemental stabilizer 1803 from the positioning mechanism 1830 to fully deploy the aneurysm device 1800.

Several embodiments of the device can have a particularly small metal-on-vessel wall footprint. The proximal support framework of atypical embodiment of the device, when implanted, contacts the vascular lumen at metal area/lumen wall area of about 1%, or in some cases 5%. Therapeutic advantages of minimizing the amount of metal contacting the luminal walls are expected to include the minimization of interference with pontine arteries emanating from the parent artery, and perforating arteries emanating from the side branching arteries. Further, a minimization of the amount of metal in the device contributes to minimization of bulk volume that needs to be compressed in its radial dimension for insertion into a delivery device.

Figure 19:
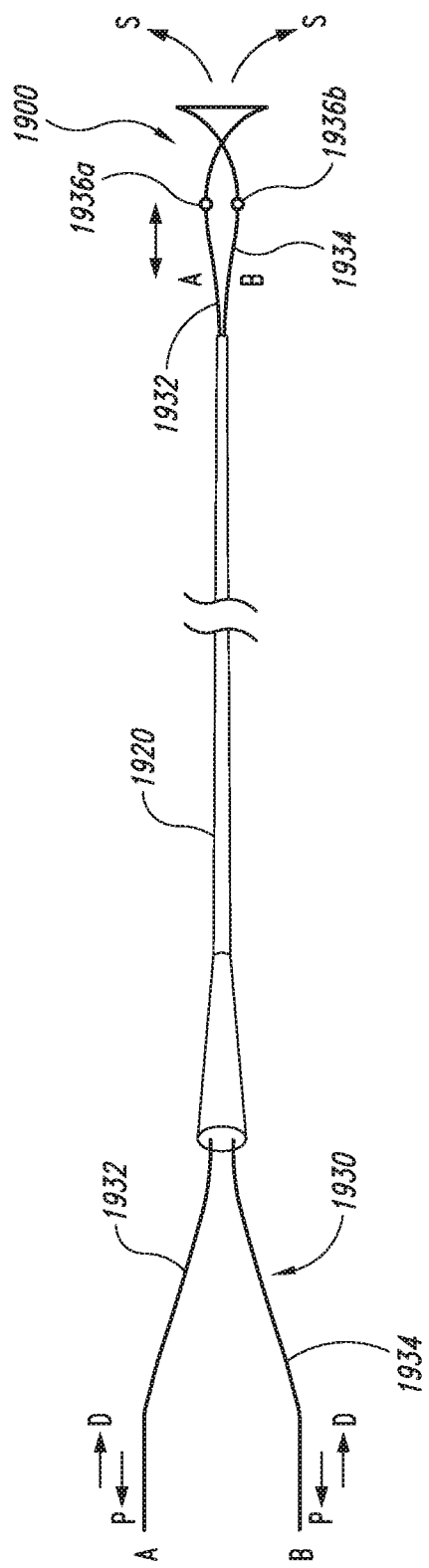
FIG. 19 is a view of a delivery device and an aneurysm device configured in accordance with an additional embodiment of the technology.

FIG. 19 illustrates another embodiment of delivering an aneurysm device 1900 using a delivery device having a delivery sheath 1920 and a steerable multi-wire positioning mechanism 1930. In the embodiment illustrated in FIG. 19, the positioning mechanism 1930 has a first push-wire 1932 and a second push-wire 1934 that extend through the delivery sheath 1920 and are attached to separate detaching elements 1936a and 1936b at separate points of the aneurysm device 1900. The positioning mechanism 1930 may have more than two independent push-wires depending on the number of proximal ends of the aneurysm device and/or whether the push-wires have forked distal ends. For example, although many embodiments of the aneurysm devices described above have been depicted as having two proximal ends at the proximal-most point of the supplemental stabilizer, the technology includes embodiments with multiple proximal-most ends of the supplemental stabilizer and/or the closure structure. The multi-wire positioning mechanism 1930 can accordingly have a complementary number of push-wires, or individual push-wires may have forked distal ends having two, three, or more tines that can be connected to the individual proximal ends of the aneurysm device 1900. The embodiment of the positioning mechanism 1930 illustrated in FIG. 19 is a dual-wire system in which the first push-wire 1932 can be moved proximally or distally (arrows P-D) independent of proximal or distal movement of the second push-wire 1934. This allows steering (arrows S) of the distal portion of the aneurysm device 1900 using a "puppet-like" control of the aneurysm device 1900 after it is positioned beyond the distal end of the positioning sheath 1920. As explained below, such enhanced steering is useful in directing the closure structure into the side branch arteries.

Implantable devices of the present technology are typically delivered to a target site, such as in the neurovasculature, in a small diameter, constrained condition. In some embodiments, the technology provides implantable device assemblies having an elongated, flexible delivery catheter, at least one elongated, flexible delivery mechanism axially movable with respect to the catheter, and an implantable device in a small diameter, constrained condition associated with a distal end of the delivery mechanism and mounted at or near a distal end of the delivery catheter. The delivery mechanism may be a delivery (or pusher) wire or tube detachably connected to the implantable device at or near its distal end. In alternative embodiments, the delivery mechanism may bean expandable or inflatable device such as a balloon that facilitates placement and/or expansion of the implantable device during deployment.

The disclosed deliverable device is designed to be compatible with available endovascular delivery system technologies and can be loaded at the proximal catheter hub and then advanced the distance of the (already placed) guiding or delivery catheter, exiting the delivery catheter at the target deployment site. Upon proper positioning at the target deployment site, the implantable device is advanced out of there straining device in a controllable fashion and, as it exits there straining device, the device assumes its larger diameter deployed condition as it is positioned at the target site.

The device may be advanced using one or more delivery wire(s) to which the device is electrolytically, mechanically, hydraulically, and/or thermally attached; and the device can be separated from the delivery wire(s) through the use of electrolytic, mechanical, hydraulic, and/or thermal techniques. Some particular embodiments of the disclosed assembly are designed for electrolytic detachment of the device from its delivery wire. Alternatively, the device may be advanced or deployed using a pusher or a push/pull technique that requires no mechanical, hydraulic, thermal or electrolytic attachment method. A pusher may act as a pusher and/or a stabilizer for deployment of the device. The device may be partially or fully deployed and detached or not depending on the application. An advantage of a system that includes attachment to a delivery wire is that the device may be withdrawn back into the delivery system in the event of a less than completely satisfactory placement or if other clinical factors indicate the appropriateness of withdrawal.

In one embodiment, implantable devices of the present technology may be deployed at a target site across the neck of an aneurysm but not detached from the delivery mechanism, and embolic or other materials maybe delivered to the site and placed within the aneurysm while the implantable device is deployed through or around the structure of the implantable device. The perimeter and/or internal framework structure of the implantable device prevents materials implanted in the interior of the aneurysm from escaping during or subsequent to placement. The implantable device may be detached and remain at the site or it may be retracted in a method that substantially reverses the deployment methodology following placement and stabilization of materials deployed within the interior of the aneurysm.

In some aspects of the technology, assemblies, systems, and methods provide an enclosing structure that can be placed across the neck of an aneurysm or a portion of the neck of an aneurysm to retain debris and other materials, such as embolic materials, within the internal cavity of the aneurysm. In some embodiments, the implantable device may be utilized in combination with adjunctive devices such as endovascular helically wound coils, liquid embolic glues, stents, and other agents that are deployed in a cavity or aneurysm prior to, during, or following placement of the implantable device across the neck of the aneurysm. The device maybe deployed and detached and left permanently across the aneurysm neck to retain debris and/or embolic materials, or the device may be deployed prior to placement of embolic materials. In this latter situation, embolic materials may be placed behind or through the mechanical structure following deployment of the device with the mechanical structure of the device retaining the embolic materials during and following their placement. The implantable device may be detached and left in place or it may be retracted following stabilization of the materials inside the aneurysm. In some embodiments, the distal framework structure of the implantable device incorporates an occlusive or semi-occlusive cover. The occlusive cover can assist in retaining debris and embolic materials within the internal cavity of the aneurysm and may alternatively or additionally provide flow diversion and exclusion/occlusion of the targeted aneurysm.

Figure 20:
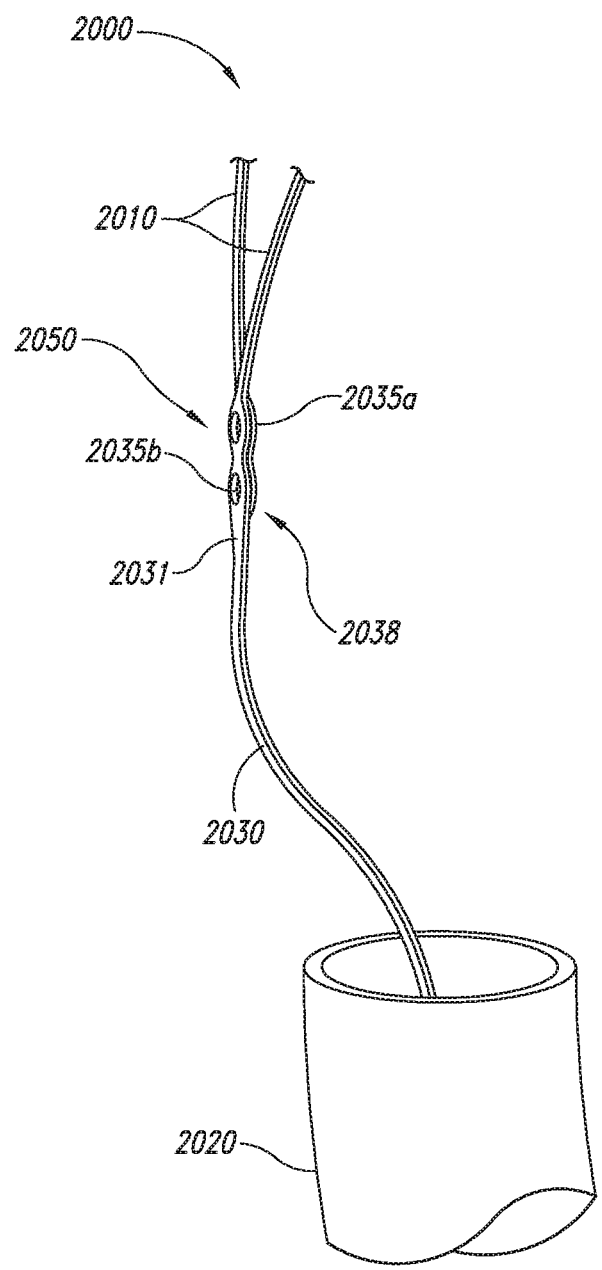
FIG. 20 is a view of a detachment element for use with a delivery device and an aneurysm device configured in accordance with an additional embodiment of the technology.

FIG. 20 illustrates an embodiment of a detachment mechanism for use with delivery devices and aneurysm devices configured in accordance with the technology. FIG. 20, more specifically, illustrates a proximal portion of an aneurysm device 2000 connected to the distal portion of a positioning mechanism 2030 by a detachment mechanism 2050. In this embodiment, struts 2010 of the aneurysm mechanism 2000 and a distal end 2031 of a push-wire of the positioning mechanism 2030 are welded together at welds 2035a and 2035b. The distal end 2031 of the push-wire is welded to the outside of the struts 2010 such that the distal end 2031 of the push-wire does not catch on the inner edge 2038 as the positioning mechanism 2030 is withdrawn into the delivery sheath 2020. It will be appreciated that other configurations may be used, but the detachment mechanism 2050 with the push-wire being welded to the outside provides an easy, strong weld that also performs better in operation.

Figure 21:
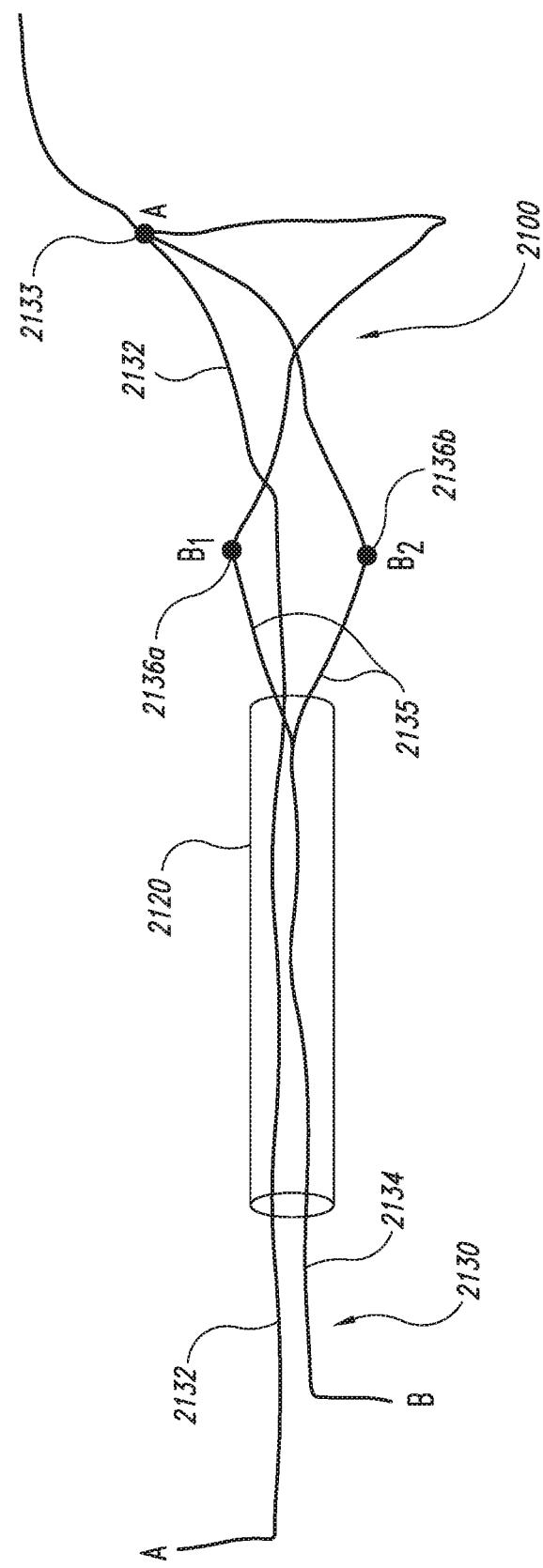
FIG. 21 is a view of a delivery device and an aneurysm device configured in accordance with an additional embodiment of the technology.
Figure 22:
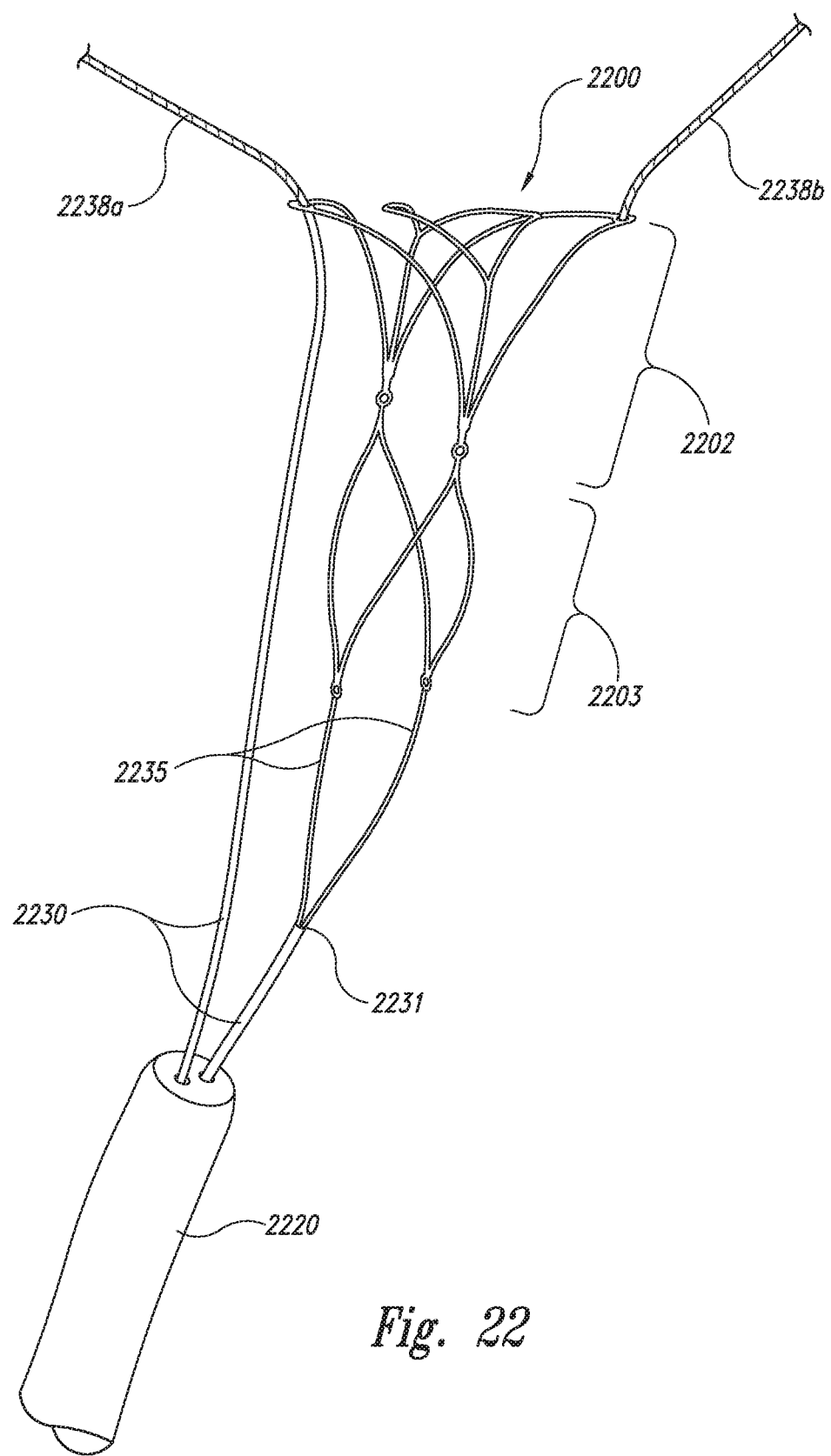
FIG. 22 is a view of a delivery device and an aneurysm device configured in accordance with an additional embodiment of the technology.
Figure 23:
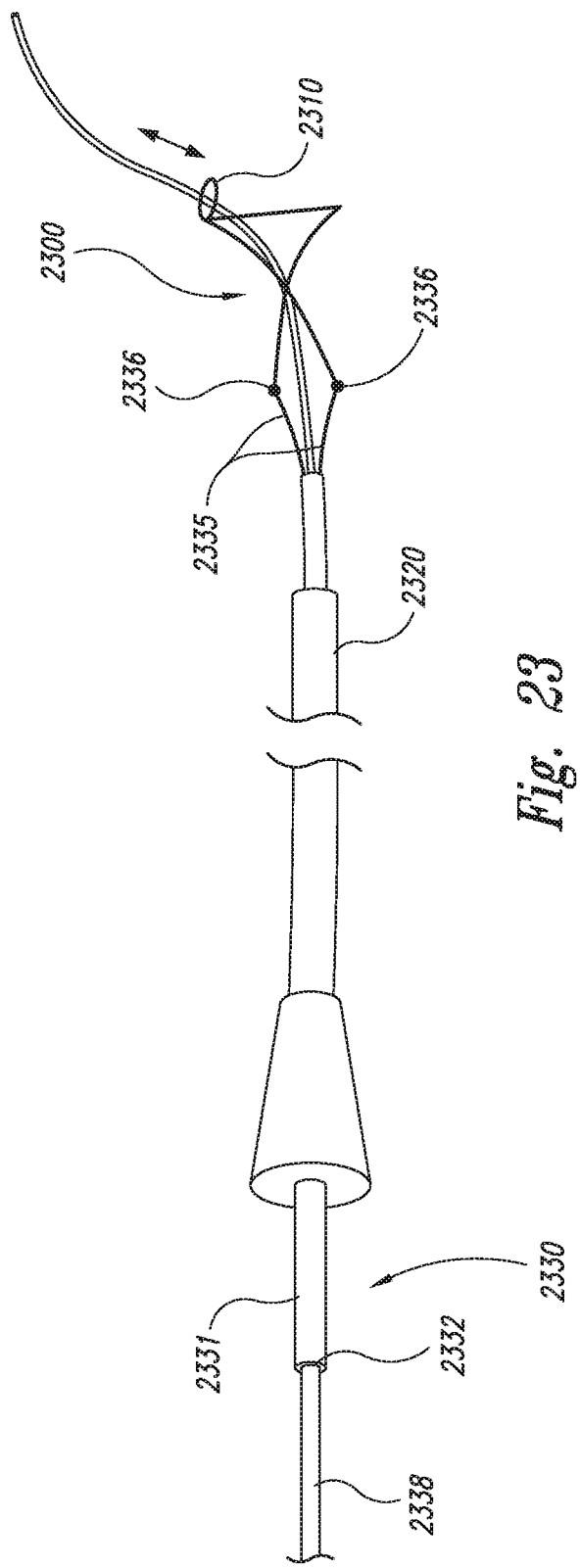
FIG. 23 is a view of a delivery device and an aneurysm device configured in accordance with an additional embodiment of the technology.

FIGS. 21-23 illustrate additional embodiments of delivery devices and aneurysm devices that provide lateral steering. In these embodiments, different push-wire and/or guidewire configurations are used to further enhance the positioning of the aneurysm device. FIG. 21 illustrates an aneurysm device 2100 being deployed by a delivering mechanism having a delivery sheath 2120 and a positioning mechanism 2130 that includes a multi-wire and multi-detachment system. More specifically, the positioning mechanism 2130 can have a first push-wire 2132 connected to a distal point of the aneurysm device at a first detachment element 2133 and a second push-wire 2134 that has a forked distal end with two tines 2135 attached to the proximal end of the aneurysm device 2100 at second detachment elements 2136a-b. The first detachment element 2133 is independently operable relative to the second detachment elements 2136a-b, and similarly the first push-wire 2132 can move proximally or distally independently relative to the second push-wire 2134. In operation, the first and second push-wires 2132 and 2134 can be manipulated to further control the orientation of the aneurysm device 2100 during deployment. Additionally, the proximal and distal portions of the aneurysm device 2100 can be released from the first or second push-wires 2132 or 2134 independently of each other to allow further control of the position of the aneurysm device 2100. For example, the first detachment element 2133 can be activated to release the distal end of the aneurysm device 2100, and then the second detachment elements 2136a-b can be activated to release the proximal end. This also allows the aneurysm device 2100 to be replaced back within the delivery sheath 2120 if the orientation is incorrect or the deployment otherwise malfunctions.

FIG. 22 is an isometric view of an aneurysm device 2200 having a closure structure 2202 and a supplemental stabilizer 2203 being deployed by a delivery device that uses at least one secondary delivery wire, such as a guidewire, to aid in the navigation and deployment orientation of the aneurysm device 2200. In the embodiment illustrated in FIG. 22, the delivery device includes a deployment sheath 2220 and a positioning mechanism 2230. The positioning mechanism 2230 can include a push-wire 2231 with a two-tine fork 2235 and at least one secondary delivery wire 2238a that is either slidably connected to or fixedly bonded to a portion of the aneurysm device 2200. In a specific embodiment shown in FIG. 22, the secondary delivery wire 2238a is a guidewire slidably or fixedly coupled to one lateral apex of the closure structure 2202, and the positioning mechanism 2230 further includes an optional second secondary delivery wire 2238b slidably or fixedly coupled to the opposing lateral apex of the closure structure 2202. The secondary delivery wire 2238a canthus act as a leading wire.

The secondary delivery wire 2238a may either be a full-length secondary wire that is independently controllable on the proximal end, or it can be a secondary apparatus incorporated into the main delivery wire to which the aneurysm device 2200 is attached. The distal end of the secondary delivery wire 2238a may have a single terminus for unidirectional orientation bias, or it may incorporate multiple termini and leading wire elements for the stability and orientation bias of the aneurysm device 2200 and torturous and complex anatomical structures where multiple adjacent vessels are present. In general, the secondary delivery wire 2238a has an overall length of greater than 30 cm and maybe as long as 350 cm depending upon the need for additional navigation purposes and for axis stability in catheter exchange scenarios. The secondary delivery wire 2238a can have different diameters along its length or a single diameter. For example, the diameter of the distal terminus of the secondary delivery wire 2238a can be 0.001 inch to 0.035 inch in selected embodiments. Specific embodiments of the secondary delivery wire 2238a can have a diameter that does not exceed 0.014 inches. In operation, the secondary delivery wire 2238a can be slidably inserted into a delivery sheath in a generally parallel orientation to the main delivery wire (e.g., the push-wire 2231).

FIG. 23 illustrates an alternate embodiment of a delivery device having a secondary delivery wire in which the secondary delivery wire is positioned coaxially within the main delivery wire. In this embodiment, the delivery device includes a delivery sheath 2320 and a positioning mechanism 2330 having a main delivery wire or tube 2331 with a lumen 2332 and a secondary delivery wire 2338 extending through the lumen 2332 of the main delivery tube 2331. The main delivery tube 2331 can further include a distal fork 2335 attached to detachment elements 2336 at the proximal end of the aneurysm device 2300. In the embodiment illustrated in FIG. 23, the aneurysm device 2300 further includes a loop 2310 through which a distal portion of the secondary delivery wire 2338 is either slidably retained or fixedly attached. In other embodiments, the positioning mechanism 2330 may include one or more additional secondary delivery wires as described above with respect to FIG. 22. Additionally, the secondary delivery wire 2338 can be detached separately from the fork 2335 of the primary delivery tube 2331 to provide additional steering control as described above.

The delivery devices described above with reference to FIGS. 19-23 are well-suited for positioning or steering the aneurysm device such that one of the two lateral ends of the distal aspect of the aneurysm device is directed toward insertion into one of the two bifurcating arteries of the implantation site. Such steering or positioning can further be enhanced by an aneurysm device with an asymmetrical closure structure as described above with reference to FIG. 6A-8D because the longer lateral area of the aneurysm device can be directed toward one bifurcating vessel while the shorter lateral area of the device can be directed toward the other bifurcating vessel.

Figure 24B:
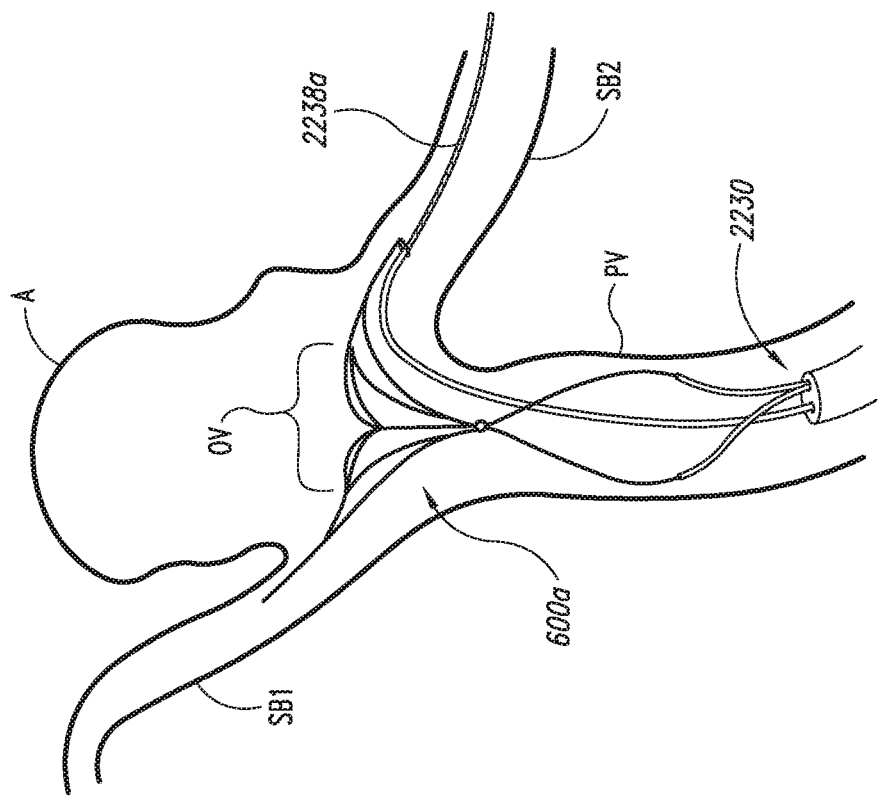
FIGS. 24A and 24B are views of multiple asymmetric aneurysm devices being implanted at a target site in accordance with an embodiment of the technology.
Figure 24A:
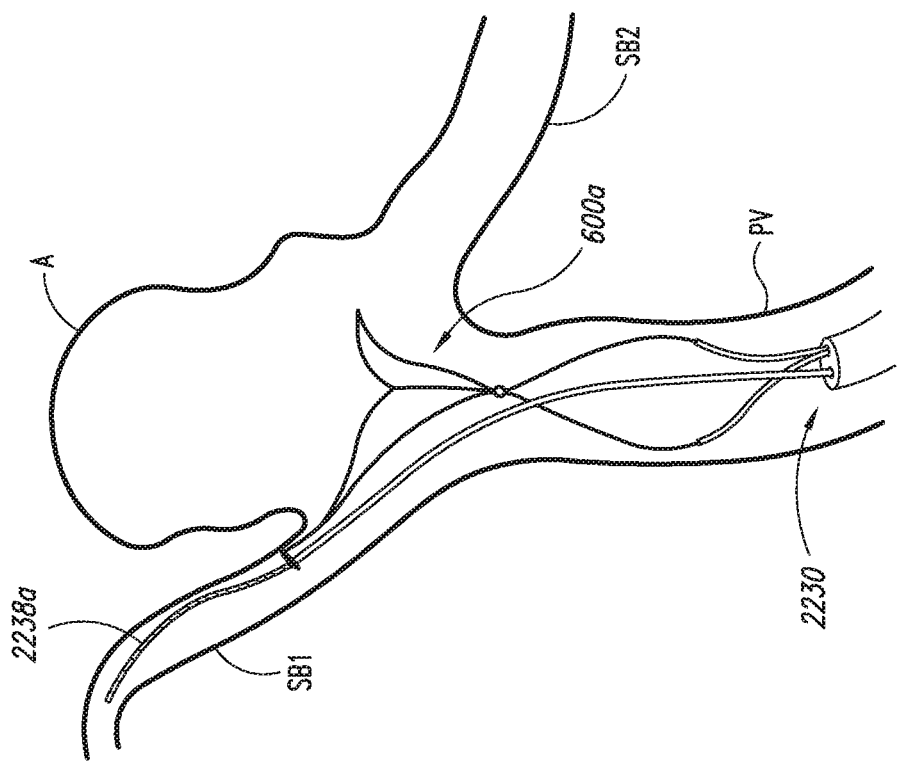

The steerable delivery device in FIGS. 19-23 can further be useful for treating or enclosing an aneurysm with two or more aneurysm devices rather than just a single aneurysm device. Referring to FIGS. 24A and 24B, for example, the two asymmetrical aneurysm devices 600a shown in FIGS. 7A and 7B are implanted in a patient. FIG. 24A shows the first aneurysm device 600a described with reference to FIG. 7A being implanted in a first side branch vessel SB1 using the positioning mechanism 2230 that has the secondary delivery wire 2238a. As shown in FIG. 24A, the secondary delivery wire 2238a can be positioned in the first side branch vessel SB1, and then the first aneurysm device 600a can be positioned to cover a portion of the neck of the aneurysm A. FIG. 24B illustrates implanting the second aneurysm device 600a to overlap the first aneurysm device in a region OV and be positioned in the second side branch vessel SB2. The second aneurysm device 600a can be implanted using the positioning mechanism 2230 of a second delivery device by positioning the secondary delivery wire 2238a down the second side branch vessel SB2. Although the asymmetric aneurysm devices described above are useful for multi-device applications, a steerable delivery device may enhance the positioning of the first and second aneurysm devices by providing more control over the position and orientation of the aneurysm devices as they are deployed.

In some implementations, a guidewire may be attached to a lateral aspect of an aneurysm closure device by an electrolytic joint. In related embodiments, electrolytic joints may join a guidewire and a device as well as at junctions between a delivery wire and the device. In a further variation on these embodiments, two individual delivery wires may be joined to individually to the two proximal ends of a device. In an embodiment such as this, separate circuits may operate the electrolytic detachment of the device from the guidewire and the electrolytic detachment of the device from the delivery wire may be independent. In yet another implementation of delivery, involving two individual wires, side-by-side independently operable delivery wires may be attached to the two proximal ends of a device. With independent operability, the device may be steered laterally such that deployment may be controlled without the use of a leading guidewire.

Another alternative embodiment of an aneurysm enclosure framework endovascularly deliverable to a site proximate an aneurysm near a terminus of a parent artery with bifurcating downstream arteries, includes a framework that, when expanded at the site, includes a distal framework portion comprising a distal-facing aspect configured to enclose the aneurysm, a proximal-facing aspect configured to arch over lumina of the downstream arteries, and radially expandable rings positioned at lateral apices of the distal framework portion and sized and configured to encircle within lumina of downstream arteries. The framework further comprises a proximal support framework connected to the distal framework portion, the support framework configured to reside in the parent artery, and biased to press outward against a luminal wall thereof.

G. Methods of Using Embodiments of the Device

Embodiments of the technology also provide methods for treating an aneurysm located near a terminus of a parent artery that bifurcates into downstream arteries. These methods can include: (a) expanding an axially-compressed framework that has a distal portion and a proximal portion at a site near the aneurysm, (b) arching the distal portion of the framework unobtrusively over lumina of the downstream arteries, and (c) applying a force outward against a luminal wall of the parent artery. This outwardly directed force originates from an axial vertex within the distal portion of the framework, the axis of the vertex being oriented orthogonal to a longitudinal axis of the proximal framework portion; the force is conveyed from the axial vertex by the proximal portion of the framework to the parent artery wall. As described above, the expanding step is typically a self-expansion process, the expansive force coming from the elastic force of highly resilient or shape memory material that biases the device to return toward its native configuration. Some embodiments of the method also include enclosing the aneurysm with the distal portion of the framework.

In some embodiments of the method, prior to the step of expanding the device, the method includes navigating the device within a delivery device through the vasculature and ultimately through the parent artery to a site near the aneurysm. The method may further include positioning the framework optimally at the aneurysm neck prior to ejecting and expanding the device. In some embodiments, ejecting and expanding the device may occur simultaneously with positioning the device at the target site. Any of these steps of navigating, ejecting, expanding, and positioning may be facilitated by visualization methodology aided by the presence of radiopaque markers disposed at various landmark sites on the device.

In some embodiments of the method, the expanding step includes the distal framework portion assuming a form of a distal-facing complex curve, such as a saddle shape or a hyperbolic paraboloid form. The expanding step may also include the proximal support framework expanding to contact a luminal surface of the parent artery.

Typical embodiments of the device include framework struts, thus the expanding step may include ejecting a set of struts from the radial constraint of a delivery device. In some embodiments, the device includes a plurality of sets of distal struts, and in these embodiments, the multiple sets of struts complete their expansion in a substantially simultaneous manner. The expanding step may also include expanding struts that comprise the proximal framework to contact a luminal surface of the parent artery.

Some embodiments of the method may further include positioning the framework at the site proximate to the aneurysm during the expanding step. Some embodiments of the method may further include positioning a distal-facing aspect of the distal framework portion proximate to an outer aspect of a neck of the aneurysm. As described above, the method may further include substantially enclosing the aneurysm with the distal portion of the framework, more particularly, with the distal-facing aspect of the distal framework portion. In another aspect, enclosing the aneurysm may be understood as separating the space within the aneurysm from the general space of the vascular system, and accordingly, slowing or preventing the vascular flow of blood into the aneurysm space.

In some embodiments of the device, the distal framework portion has a lateral axis orthogonal to a longitudinal axis of the proximal portion. In these embodiments, the method may further include positioning the lateral axis of the distal framework portion such that the lateral axis is substantially aligned with a common longitudinal axis of the downstream arteries. Some embodiments of the method may further include extending a distal-facing aspect of the framework from an aneurysm neck into a downstream artery. Some embodiments of the method may further include contacting a distal-facing aspect of the framework against a distal surface of a downstream artery while not contacting a proximal surface of the downstream artery.

Some embodiments of the method may further include positioning the proximal framework portion within the parent artery such that a central longitudinal axis of the framework is aligned with a longitudinal axis of the parent artery.

Embodiments of the framework of the device can be understood to contact vessel luminal walls of the target site within an outlined footprint described by the outer boundaries of the device. The amount of vessel wall surface area within that footprint that is actually contacted by the framework can be understood as being but a fraction of the total area of the footprint. Some embodiments of the method may include contacting luminal walls of the parent artery and the downstream arteries with a metal surface area such that a ratio of metal area to wall area is no greater than 5%, and more specifically 3-4%. Some embodiments of the method may further include contacting luminal walls of the parent artery such that at a ratio of metal area to wall area is no greater than about 1% to about 10%.

Some embodiments of the method may include distally collapsing the framework (i.e., the collapse proceeds in a proximal-to-distal direction) for insertion into a delivery device or sheath. In some embodiments of the method, the expanding step comprises ejecting a set of struts from the radial constraint of a delivery device. The expansion in concert with ejection of struts occurs in distal-to-proximal direction. Some embodiments of the method may include detaching the framework from a delivery device. In some of these embodiments, detaching may include electrolytically eroding a portion of a delivery wire that connects the device to the wire. Some embodiments of the method may further include ejecting a device from a delivery device without detaching it and pulling the device back into the delivery device. This latter aspect of the method may occur in conjunction with repositioning the device into a more favorable therapeutic position at the target site.

Some embodiments of the method of treating an aneurysm further include injecting embolic coils or other coagulative material into the aneurysm in conjunction with implanting an embodiment of the aneurysm enclosure device. In typical embodiments of this method, the embolic coils are injected into the aneurysm by conventional methods except for the route passing through struts of the inventive framework prior to entering the aneurysm.

From the foregoing, it will be appreciated that specific embodiments of the disclosure have been described herein for purposes of illustration, but that various modifications may be made without deviating from the spirit and scope of the disclosure. For example, structures and/or processes described in the context of particular embodiments may be combined or eliminated in other embodiments. In particular, the aneurysm devices described above with reference to particular embodiments can include one or more additional features or components, or one or more of the features described above can be omitted. Moreover, while advantages associated with certain embodiments of the disclosure have been described in the context of these embodiments, other embodiments may also exhibit such advantages, and not all embodiments need necessarily exhibit such advantages to fall within the scope of the disclosure. Accordingly, embodiments of the disclosure are not limited except as by the appended claims.

The disclosure will now be defined by the following clauses:

1. An aneurysm device endovascularly deliverable to a site proximate an aneurysm near a terminus of a parent artery with bifurcating downstream arteries, the aneurysm device comprising:

a closure structure comprising a distal-facing aspect configured to at least partially occlude the aneurysm and a proximal-facing aspect configured to arch over lumina of the downstream arteries; and a supplemental stabilizer connected to the closure structure, the supplemental stabilizer configured to reside in the parent artery and press outward against a luminal wall thereof.

2. The aneurysm device of clause 1 wherein the closure structure comprises a distal framework portion having a lateral axis orthogonal to a longitudinal axis of the supplemental stabilizer, the supplemental stabilizer has a proximal framework portion, and the lateral axis of the distal framework portion comprises a vertex from which the proximal support framework is biased to press outward against a luminal wall of the parent artery.

3. The aneurysm device of clause 2 wherein the distal-facing aspect of the distal framework portion forms a complex curved surface.

4. The aneurysm device of clause 3 wherein the complex curved surface comprises a hyperbolic paraboloid form.

5. The aneurysm device of clause 3 wherein the complex curved surface comprises two opposing apices aligned longitudinally with respect to the parent artery, and deflected proximally thereinto.

6. The aneurysm device of clause 3 wherein the complex curved surface comprises two opposing apices aligned longitudinally with respect to the downstream arteries, and extending thereinto.

7. The aneurysm device of clause 2 wherein the ratio of a surface area of the closure structure aligned against an area of combined parent artery luminal wall and downstream artery luminal wall is less than about 5% of the total area within an area defined by an outer boundary of the aneurysm device.

8. The aneurysm device of clause 2 wherein the ratio of a proximal support framework surface area aligned against an area of parent artery luminal wall is less than about 1% of the total area within an area defined by the outer boundaries of the proximal framework contact against the wall.

9. The aneurysm device of clause 2 wherein the distal framework portion, if laid out in a planar form, comprises a quadrilateral form having two sets of paired opposing apices. Revisit this one.

10. The aneurysm device of clause 1 wherein the closure structure comprises struts.

11. The aneurysm device of clause 10 comprising two proximal junctions at proximally-deflected apices of the hyperbolic parabolic form, the proximal junctions joining together at least some of the struts of the framework.

12. The aneurysm device of clause 1 wherein the device is radially compressible into a low-profile for endovascular delivery.

13. The aneurysm device of clause 12 wherein the device is axially compressible, at least in part, by a distal-ward foldability of the closure structure.

14. The aneurysm device of clause 12 wherein the device is radially compressible to a diameter of about 0.010 inch to about 0.040 inch.

15. The aneurysm device of clause 2, wherein the distal framework portion comprises a lateral axis configured to align with a longitudinal axis substantially defined by the downstream arteries, the lateral axis being oriented substantially transverse to a longitudinal axis of the proximal support framework, and the support framework being configured to align with a longitudinal axis of the parent artery.

16. The aneurysm device of clause 2 wherein the distal framework portion comprises two opposing lateral faces, the lateral faces configured to drape proximally over the lumina of the downstream arteries, the faces substantially parallel to the longitudinal axis of the distal framework portion.

17. The aneurysm device of clause 2 wherein the distal framework portion comprises at least one laterally elongated portion such that, when the device is deployed, the distal framework portion aligns lengthwise with a longitudinal axis of the downstream arteries.

18. The aneurysm device of clause 17 wherein the laterally elongated portion is sized and configured to extend into a lumen of a downstream artery, beyond a circumferential boundary of the luminal wall of the parent artery.

19. The aneurysm device of clause 17 wherein the laterally elongated portion contacts a distal surface of a lumen of one of more of the downstream arteries without contacting a proximal surface of the lumen.

20. The aneurysm device of clause 2 wherein the distal framework portion comprises two laterally elongated portions of asymmetric length.

21. The aneurysm device of clause 2 wherein the distal framework portion comprises two laterally elongated portions of symmetric length.

22. The aneurysm device of clause 2 further comprising a barrier supported by at least the distal-facing aspect of the distal framework portion.

23. The aneurysm device of clause 22 wherein the distal-facing aspect of the distal framework portion comprises struts that form a polygonal face with a peripheral boundary, and wherein the barrier is a membrane that covers the face substantially to the peripheral boundary.

24. The aneurysm device of clause 22 wherein the distal-facing aspect of the distal framework portion comprises struts that form an inner support within a peripheral support, and wherein the barrier is a membrane that covers only the inner support.

25. The aneurysm device of clause 22 wherein the distal-facing aspect of the distal framework portion comprises struts that form an inner support within a peripheral support, and wherein the barrier is a membrane that covers only a space between the internal and the peripheral supports.

26. The device of clause 22 wherein the distal framework portion comprises two proximally deflected apices, and wherein the barrier is a membrane that forms a proximal-facing wedge that extends along an axis connecting the two longitudinally deflected apices.

27. The aneurysm device of clause 2 wherein the distal framework portion comprises a lateral aspect aligned against a distal portion of the wall of side branch artery lumen and across the aneurysm neck, the lateral aspect not in contact with the proximal wall of the side branch artery lumen.

28. The aneurysm device of clause 2 wherein a profile of the distal framework portion extends beyond the bounds of a cylindrical profile.

29. The aneurysm device of clause 2 wherein the proximal support framework has a central longitudinal axis, and wherein the proximal support framework is sized and configured such that its longitudinal axis can align longitudinally within a lumen of the parent artery.

30. The aneurysm device of clause 1 wherein the closure structure and the supplemental stabilizer comprise struts comprising resilient materials selected from the group comprising metals, polymers, and composite materials.

31. The aneurysm device of clause 2 wherein the aneurysm enclosure framework comprises super elastic shape memory materials.

32. The aneurysm device of clause 31 wherein the super elastic shape memory material comprises Nitinol.

33. The aneurysm device of clause 2 wherein the aneurysm enclosure framework comprises materials selected from the group comprising solid wire, tubular wire, and braided wire.

34. The aneurysm device of clause 1 further comprising radiopaque markers.

35. An aneurysm treatment device, comprising:
a closure having a curved portion configured to extend longitudinally along a first vessel, the curved portion defining an arch about a longitudinal axis of the first vessel, and the curved portion being configured to exert an outward force against the first vessel and extend across at least a portion of a neck of an aneurysm at the first vessel; and
a supplemental stabilizer extending from the closure structure transversely to the longitudinal axis of the first vessel, the supplemental stabilizer being configured to exert an outward force against a second vessel that extends transversely to the first vessel.

36. The device of clause 35 wherein the closure structure comprises a distal framework portion and the supplemental stabilizer comprises a proximal framework portion.

37. The device of clause 36 wherein the distal and proximal framework portions each comprise a plurality of struts.

38. The device of clause 37 wherein the struts comprise a shape memory material, a noble metal, stainless steel and/or a polymeric material.

39. The device of clause 35 wherein the closure structure comprises a distal framework portion having a perimeter support including a first lateral apice and a second lateral apice spaced apart from the first lateral apice along a lateral aspect of the closure structure.

40. The device of clause 39 wherein the closure structure further comprises an inner support spaced apart from the perimeter support and connector struts extending between the inner support and the perimeter support.

41. The device of clause 39 wherein the closure structure further comprises an inner support spaced apart from the perimeter support and two proximal junctions at which the inner support is attached to the perimeter support.

42. The device of clause 41 wherein the proximal junctions of the distal framework portion are the only connection between the inner support and the perimeter support.

43. The device of clause 39 wherein the closure structure further comprises an inner support spaced apart from the perimeter support, and wherein the inner and perimeter supports have struts that curve inwardly toward a longitudinal axis of the aneurysm device.

44. The device of clause 42 wherein the inner and perimeter supports have rhombus-like shapes arranged at least substantially concentric with each other.

45. The device of clause 35 wherein: the closure structure has a perimeter support and an inner support; the inner and perimeter supports have a curved portion that is convex in the distal direction and sides projecting proximally from the curved portion; and the curved portion is configured to bias the sides outwardly.

46. The device of clause 45 wherein the inner and perimeter supports have first lateral apices and second lateral apices at an opposite side along a lateral aspect of the aneurysm device.

47. The device of clause 46 wherein the first and second lateral apices are curved distally.

48. The device of clause 46 wherein the first lateral apices are curved distally and the second lateral apices are curved proximally.

49. The device of clause 46 wherein the first and second lateral apices are curved proximally.

50. The device of clause 45 wherein the inner and perimeter supports are asymmetric such that one lateral side is longer than an opposite lateral side along a lateral aspect of the aneurysm device.

51. The device of clause 45 wherein the closure structure further comprises at least one loop at an apice of the perimeter support, and wherein the loop is configured to expand and contact a circumferential band around the first vessel at a location lateral of the aneurysm.

52. The device of clause 35 wherein the supplemental stabilizer comprises struts projecting proximally from the closure structure.

53. The device of clause 35 wherein the supplemental stabilizer comprises at least a first helical leg projecting proximally from one side of the closure structure.

54. The device of clause 53 further comprises a second helical leg projecting from another side of the closure structure.

55. The device of clause 53 wherein the first and second helical legs are wound in the same direction.

56. The device of clause 53 wherein the first and second helical legs are wound in opposite directions.

57. The device of clause 35 wherein the closure structure comprises struts having a first thickness and the supplemental support comprises struts having a second thickness different than the first thickness.

58. The device of clause 57 wherein the first thickness is less than the second thickness.

59. The device of clause 57 wherein the first thickness is greater than the second thickness.

60. The device of clause 35 wherein the closure structure is connected to the supplemental stabilizer by an articulating joint such that the closure structure can rotate relative to the supplemental stabilizer.

61. The device of clause 35, further comprising a barrier attached to at least a portion of the closure structure.

62. The device of clause 35 wherein:
the closure structure has a perimeter support and an inner support;
the inner and perimeter supports have a curved portion that is convex in the distal direction and sides projecting proximally from the curved portion;
the curved portion is configured to bias the sides outwardly; and
the aneurysm device further comprises a barrier attached to at least the perimeter support.

63. The device of clause 35 wherein:
the closure structure has a perimeter support and an inner support;
the inner and perimeter supports have a curved portion that is convex in the distal direction and sides projecting proximally from the curved portion;
the curved portion is configured to bias the sides outwardly; and
the aneurysm device further comprises a barrier attached to only the inner support.

64. The device of clause 35 wherein:
the closure structure has a support; and
the aneurysm device further includes a barrier attached to the support.

65. The device of clause 64 wherein the barrier comprises a permeable membrane.

66. The device of clause 65 wherein the permeable membrane is porous.

67. The device of clause 64 wherein the barrier comprises an impermeable membrane.

68. The device of clause 64 wherein the barrier comprises a sheet and at least one one-way valve through the sheet.

69. The device of clause wherein the barrier comprises a plurality of flexible, polymeric strands attached to the support.

70. A system for treating an aneurysm, the system comprising:
an aneurysm device according to any of clauses 35-69; and
a delivery device configured to translate the aneurysm device through vasculature of a patient and deploy the aneurysm device at a target site.

71. The system of clause 70 wherein the delivery device further comprises a sheath and a positioning mechanism.

72. The system of clause 71 wherein the positioning mechanism further comprises a plurality of wires including a first wire and a second wire.

73. The system of clause 72 wherein the first and second wires are configured to move proximally/distally relative to the sheath independently of each other, and the first and second wires are attached to different parts of the aneurysm device.

74. The system of clause 73 wherein the first and second wires are attached to the aneurysm device at a proximal portion of the supplemental support.

75. The system of clause 73 wherein the first wire is attached to the aneurysm device at a first point and the second wire is attached to the aneurysm device at a second point proximal of the first point.

76. The system of clause 71 wherein the deliver device comprises a main wire attached to the aneurysm device and a secondary delivery wire coupled to the aneurysm device, and wherein the main wire is configured to translate the aneurysm device relative to the sheath and the secondary delivery wire is configured to be positioned in the vasculature ahead of the aneurysm device.

77. The system of clause 76 wherein the secondary delivery wire is a guidewire configured to be placed in the vasculature beyond a target site and the aneurysm device is configured to slide along the guidewire.

78. The system of clause 76 wherein the main delivery wire is a tube having a lumen, and the secondary delivery wire is positioned coaxially within the lumen of the tube.

79. An aneurysm enclosure framework in a planar configuration prior to assembly into a deliverable configuration, the aneurysm enclosure framework comprising:
a central framework portion and two support framework portions, the support framework portions connected to opposite sides of the central framework portion, the central and support framework portions aligned along a longitudinal axis; and
the central framework portion comprising a set of central struts forming at least one quadrilateral form with first and second longitudinal junctions joining the struts at two longitudinal apices, and two lateral junctions joining the struts at apices of a lateral axis,
each of the two support framework portions, a first portion and a second portion, comprising a pair of struts, a first strut and a second strut, each strut having an internal central and a peripheral end, the struts of the first support framework portion connected together at their internal ends to the first longitudinal junction, the struts of the second support framework portion connected together at their internal ends to the second longitudinal junction, each strut spread outward from its respective longitudinal junction.

80. An aneurysm enclosing strut-based framework endovascularly deliverable to a site proximate an aneurysm near a terminus of a parent artery with bifurcating downstream arteries, the framework, when expanded at the site, the strut-based framework comprising:

a distal framework portion comprising a comprising a set of distal struts forming at least one quadrilateral form with first and second longitudinal junctions joining the struts at two proximal apices, and two lateral junctions joining the struts at apices of a lateral axis, the quadrilateral form comprising a distal-facing aspect configured to enclose the aneurysm and a proximal-facing aspect configured to arch over lumina of the downstream arteries; and a proximal support framework connected to the distal framework portion, the proximal support framework configured to reside in the parent artery, and biased to press outward against a luminal wall thereof, the proximal support framework comprising a first and a second support framework portion, the two support framework portions each comprising a pair of struts, a first strut and a second strut, each strut having an distal and a proximal end, the struts of the first support framework portion connected together at their distal ends to the first longitudinal junction of the distal framework, the struts of the second support framework portion connected together at their distal ends to the second longitudinal junction of the distal framework, the first strut of the first support framework portion and the first strut of the second support framework portion connected together at their proximal ends, and the second strut of the first support framework portion and the second strut of the second support framework portion connected together at their proximal ends.

81. A vascular inflow deflector for an aneurysm, the deflector endovascularly deliverable to a site proximate an aneurysm near a terminus of a parent artery with bifurcating downstream arteries, the deflector, when expanded at the site, comprising:

a distal framework portion comprising a distal-facing aspect configured to enclose the aneurysm, a proximal-facing aspect configured to arch over lumina of the downstream arteries, and two proximally deflected apices aligned on an axis orthogonal to a central axis of the bifurcating arteries;

a wedge comprising a proximal-facing linear aspect of a membrane arranged across at least a portion of the distal framework portion, the wedge extending along an axis connecting the two longitudinally deflected apices, the wedge configured to divert vascular flow away from the aneurysm and into the bifurcating arteries; and a proximal support framework connected to the distal framework portion, the support framework configured to reside in the parent artery and biased to press outward against a luminal wall thereof.

82. An aneurysm cover endovascularly deliverable to a site proximate an aneurysm near a terminus of a parent artery with bifurcating downstream arteries, the aneurysm cover, when expanded at the site, the aneurysm cover comprising:

a distal framework portion comprising a distal-facing aspect configured to enclose the aneurysm and a proximal-facing aspect configured to arch over lumina of the downstream arteries;

a membrane arranged across the distal-facing aspect of the distal portion; and a proximal support framework connected to the distal framework portion, the support framework configured to reside in the parent artery and biased to press outward against a luminal wall thereof 83. The device of clause 82 wherein the membrane comprises pores.

84. The device of clause 83 wherein the pores are distributed range in diameter from about 0.5 microns to about 400 microns.

85. The device of clause 82 wherein the membrane comprises cutout holes distributed in proximity to a periphery of the membrane.

86. An aneurysm enclosure framework endovascularly deliverable to a site proximate an aneurysm near a terminus of a parent artery with bifurcating downstream arteries, the framework, when expanded at the site, the aneurysm enclosure framework comprising:

a distal framework portion comprising a distal-facing aspect configured to enclose the aneurysm and a proximal-facing aspect configured to arch over lumina of the downstream arteries; and a proximal support framework connected to the distal framework portion, the support framework comprising a helical configured to reside in the parent artery and biased to radially expand against the wall thereof.

87. An aneurysm enclosure framework endovascularly deliverable to a site proximate an aneurysm near a terminus of a parent artery with bifurcating downstream arteries, the framework, when expanded at the site, the aneurysm enclosure framework comprising:

a distal framework portion comprising a distal-facing aspect configured to enclose the aneurysm, a proximal-facing aspect configured to arch over lumina of the downstream arteries, and radially expandable rings positioned at lateral apices of the distal framework portion and sized and configured to encircle within lumina of downstream arteries; and a proximal support framework connected to the distal framework portion, the support framework configured to reside in the parent artery, and biased to press outward against a luminal wall thereof.

88. A method of treating an aneurysm located at a site proximate a terminus of a parent artery that bifurcates into downstream arteries, the method comprising:

expanding an axially-compressed framework comprising a distal portion and a proximal portion at a site proximate to the aneurysm;

arching the distal portion of the framework unobtrusively over lumina of the downstream arteries; and applying a force outward against a luminal wall of the parent artery, the force originating from an axial vertex within the distal portion of the framework, the axis of the vertex oriented orthogonal to a longitudinal axis of the proximal framework portion, the force being conveyed by the proximal portion of the framework to the parent artery wall.

89. The method of clause 88, further comprising substantially enclosing the aneurysm with the distal portion of the framework.

90. The method of clause 88 wherein prior to the expanding step, further comprising navigating the device through the parent artery to a site in proximity to the aneurysm within a delivery device.

91. The method of clause 88, further comprising positioning the framework at the site proximate to the aneurysm prior to the expanding step.

92. The method of clause 88, further comprising positioning the framework at the site proximate to the aneurysm during the expanding step.

93. The method of clause 88, further comprising positioning a distal-facing aspect of the distal framework portion proximate to an outer aspect of a neck of the aneurysm.

94. The method of clause 88, further comprising visualizing radiopaque markers on the framework during any of the navigating, positioning, or expanding steps.

95. The method of clause 88 wherein the expanding step comprises a distal-facing aspect of the distal framework portion assuming a form of a complex curve.

96. The method of clause 95 wherein the complex curve form is a hyperbolic paraboloid.

97. The method of clause 88 wherein the distal framework portion comprises struts and expanding step comprises ejecting a distal set of struts from the radial constraint of a delivery device.

98. The method of clause 97 wherein ejecting the set of struts from the radial constraint of a delivery device is completed substantially simultaneously.

99. The method of clause 88 wherein the expanding step comprises the proximal framework portion expanding to contact a luminal surface of the parent artery.

100. The method of clause 88 wherein the distal framework portion has a lateral axis orthogonal to a longitudinal axis of the proximal portion, the method further comprising positioning the lateral axis of the distal framework portion such that the lateral axis is substantially aligned with a common longitudinal axis of the downstream arteries.

101. The method of clause 88, further comprising positioning a distal-facing aspect of the framework from an aneurysm neck into a downstream artery.

102. The method of clause 88, further comprising contacting a distal-facing aspect of the framework against a distal surface of a downstream artery while not contacting a proximal surface of the downstream artery.

103. The method of clause 88, further comprising positioning the proximal framework portion within the parent artery such that a central longitudinal axis of the framework is aligned with a longitudinal axis of the parent artery.

104. The method of clause 88, further comprising contacting luminal walls of the parent artery and the downstream arteries within a footprint defined by the boundaries of device contact with a surface of the device at a ratio of device surface to wall surface of no greater than 5%.

105. The method of clause 88, further comprising contacting luminal walls of the parent artery within a footprint defined by the boundaries of the proximal portion of the device contact with a surface of the device at a ratio of device surface to wall surface of no greater than 1-10% .

106. The method of clause 88, further comprising distally collapsing the framework for insertion into a delivery device.

107. The method of clause 88, further comprising detaching the framework from a delivery device.

108. The method of clause 107 wherein detaching the framework from the delivery device comprises an electrolytically eroding a portion of a delivery wire.

109. The method of clause 88, further comprising ejecting a device from a delivery device and pulling the device back into the delivery device.

110. The method of clause 88, further comprising injecting embolic coils or other coagulative material through the distal framework portion and the aneurysm neck into the target aneurysm.

111. A method of diverting blood flow away from an aneurysm of a patient, the aneurysm at a site proximate a terminus of a parent artery that bifurcates into downstream arteries, the method comprising:

positioning a diverter facing into the vascular flow over the neck of the aneurysm, a distal framework portion comprising a distal-facing aspect configured to enclose the aneurysm, a proximal-facing aspect configured to arch over lumina of the downstream arteries, and two proximally deflected apices aligned on an axis orthogonal to a central axis of the bifurcating arteries; a wedge comprising a proximal-facing linear aspect of a membrane arranged across at least a portion of the distal framework portion, the wedge extending along an axis connecting the two longitudinally deflected apices, the wedge configured to divert vascular flow away from the aneurysm and into the bifurcating arteries; and a proximal support framework connected to the distal framework portion, the support framework configured to reside in the parent artery, and biased to press outward against a luminal wall thereof.

112. A method of treating an aneurysm of a patient, the aneurysm at a site proximate a terminus of a parent artery that bifurcates into downstream arteries, the method comprising:

determining the three dimensional configuration of the patient's aneurysm and the surrounding site;

selecting an aneurysm enclosure framework endovascularly deliverable to the three dimensional configuration of the aneurysm and the surrounding locale, the selected framework, when expanded at the site, sized and configured to conform to the site, the framework comprising a distal framework portion comprising a distal-facing aspect configured to enclose the aneurysm and a proximal-facing aspect configured to arch over lumina of the downstream arteries; and a proximal support framework connected to the distal framework portion, the support framework configured to reside in the parent artery, and biased to press outward against a luminal wall thereof; and delivering the enclosure framework to the site.

113. A method of treating an aneurysm of a patient, the aneurysm at a site proximate a terminus of a parent artery that bifurcates into downstream arteries, the method comprising:

determining the three dimensional configuration of the patient's aneurysm and the surrounding site;

forming an aneurysm enclosure framework endovascularly deliverable to the three dimensional configuration of the patient's aneurysm and the surrounding site, the formed framework, when expanded at the locale, sized and configured to conform to the site, the framework comprising a distal framework portion comprising a distal-facing aspect configured to enclose the aneurysm and a proximal-facing aspect configured to arch over lumina of the downstream arteries; and a proximal support framework connected to the distal framework portion, the support framework configured to reside in the parent artery, and biased to press outward against a luminal wall thereof; and delivering the enclosure framework to the site.

114. A method of making an aneurysm enclosure framework comprising:

providing an enclosure framework in a planar configuration, the framework comprising:

a central framework portion and two support framework portions, a first and a second support framework portion, the support framework portions connected to opposite sides of the central framework portion, the central and support framework portions aligned along a longitudinal axis, the central framework portion comprising a set of central struts forming at least one quadrilateral form with first and second longitudinal junctions joining the struts at two longitudinal apices, and two lateral junctions joining the struts at apices of a lateral axis, the two support framework portions each comprising a pair of struts, a first strut and a second strut, each strut having an internal and a peripheral end, the struts of the first support framework portion connected together at their internal ends to the first longitudinal junction, the struts of the second support framework portion connected together at their internal ends to the second longitudinal junction, each support strut spread outward from its respective longitudinal junction;

joining together the peripheral ends of the first strut of the first support framework portion and the first strut of the second support framework portion; and joining together the peripheral ends of the second strut of the first support framework portion and the second strut of the second support framework portion.

What is claimed is:

1. An aneurysm treatment device, comprising:
a closure structure having a curved portion configured to extend longitudinally along a first vessel, the curved portion defining an arch about a longitudinal axis of the first vessel, and the curved portion being configured to exert an outward force against the first vessel and extend across at least a portion of a neck of an aneurysm at the first vessel; and
a supplemental stabilizer extending from the closure structure transversely to the longitudinal axis of the first vessel, the supplemental stabilizer being configured to exert an outward force against a second vessel that extends transversely to the first vessel;
wherein the closure structure comprises a distal framework portion having a perimeter support including a first lateral apice and a second lateral apice spaced apart from the first lateral apice along a lateral aspect of the closure structure, and
wherein:
the closure structure has an inner support;
the inner and perimeter supports have a curved portion that is convex in a distal direction and sides projecting proximally from the curved portion; and
the curved portion is configured to bias the sides outwardly.

2. The device of claim 1, wherein the closure structure further comprises connector struts extending between the inner support and the perimeter support.

3. The device of claim 1, wherein the closure structure further comprises two proximal junctions at which the inner support is attached to the perimeter support.

4. The device of claim 3, wherein the proximal junctions of the distal framework portion are the only connection between the inner support and the perimeter support, and wherein the inner and perimeter supports have rhombus-like shapes arranged at least substantially concentric with each other.

5. The device of claim 1, wherein the inner and perimeter supports have struts that curve inwardly toward a longitudinal axis of the aneurysm treatment device.

6. The device of claim 1, wherein the inner and perimeter supports are asymmetric such that one lateral side is longer than an opposite lateral side along a lateral aspect of the aneurysm treatment device.

7. The device of claim 1, wherein the closure structure further comprises at least one loop at an apice of the first and second lateral apices of the perimeter support, and wherein the at least one loop is configured to expand and contact a circumferential band around the first vessel at a location lateral of the aneurysm.

8. The device of claim 1, wherein the inner and perimeter supports have a plurality of the first lateral apices and a plurality of the second lateral apices.

9. The device of claim 8, wherein the plurality of the first lateral apices are curved distally and the plurality of the second lateral apices are curved proximally.

10. The device of claim 1, wherein the supplemental stabilizer comprises struts projecting proximally from the closure structure.

11. The device of claim 1, wherein the supplemental stabilizer comprises at least a first helical leg projecting proximally from one side of the closure structure.

12. The device of claim 11, further comprises a second helical leg projecting from another side of the closure structure.

13. The device of claim 1, wherein the closure structure comprises struts having a first thickness and the supplemental support comprises struts having a second thickness different than the first thickness.

14. The device of claim 13, wherein the first thickness is less than the second thickness.

15. The device of claim 1, wherein the closure structure is connected to the supplemental stabilizer by an articulating joint such that the closure structure can rotate relative to the supplemental stabilizer.

16. The device of claim 1, further comprising a barrier attached to at least a portion of the closure structure.

17. The device of claim 1, wherein:
the aneurysm treatment device further comprises a barrier attached to at least the perimeter support.

18. An aneurysm enclosure framework in a planar configuration prior to assembly into a deliverable configuration, the aneurysm enclosure framework comprising:
a central framework portion and two support framework portions, the support framework portions connected to opposite sides of the central framework portion, the central and support framework portions aligned along a longitudinal axis; and
the central framework portion comprising a set of central struts forming at least one quadrilateral form with first and second longitudinal junctions joining the struts at two longitudinal apices, and two lateral junctions joining the struts at apices of a lateral axis,
each of the two support framework portions, a first portion and a second portion, comprising a pair of struts, a first strut and a second strut, each strut having an internal central and a peripheral end, the struts of the first support framework portion connected together at their internal ends to the first longitudinal junction, the struts of the second support framework portion connected together at their internal ends to the second longitudinal junction, each strut spread outward from its respective longitudinal junction.

19. An aneurysm enclosure framework endovascularly deliverable to a site proximate an aneurysm near a terminus of a parent artery with bifurcating downstream arteries, the framework, when expanded at the site, the aneurysm enclosure framework comprising:
a distal framework portion comprising a distal-facing aspect configured to enclose the aneurysm, a proximal-facing aspect configured to arch over lumina of the downstream arteries, and radially expandable rings positioned at lateral apices of the distal framework portion and sized and configured to expand within lumina of downstream arteries; and a proximal support framework connected to the distal framework portion, the support framework configured to reside in the parent artery, and biased to press outward against a luminal wall thereof, wherein:

the distal-facing aspect has a perimeter support and an inner support;

the inner and perimeter supports have a curved portion that is convex in a distal direction and sides projecting proximally from the curved portion; and the curved portion is configured to bias the sides outwardly.

* * * * *